(12) United States Patent
Leblanc

(10) Patent No.: US 11,160,788 B2
(45) Date of Patent: Nov. 2, 2021

(54) CASPASE-1 INHIBITION AND USES THEREOF FOR PREVENTION AND TREATMENT OF NEUROLOGICAL CONDITIONS

(71) Applicant: Andrea Leblanc, Grand-Barachois (CA)

(72) Inventor: Andrea Leblanc, Grand-Barachois (CA)

(73) Assignee: Andrea LeBlanc

( * ) Notice: Subject to any disclaimer, the term of this patent is extended or adjusted under 35 U.S.C. 154(b) by 0 days.

(21) Appl. No.: 16/471,047

(22) PCT Filed: Dec. 20, 2017

(86) PCT No.: PCT/CA2017/051548
§ 371 (c)(1),
(2) Date: Jun. 19, 2019

(87) PCT Pub. No.: WO2018/112626
PCT Pub. Date: Jun. 28, 2018

(65) Prior Publication Data
US 2019/0328709 A1    Oct. 31, 2019

Related U.S. Application Data

(60) Provisional application No. 62/438,529, filed on Dec. 23, 2016, provisional application No. 62/579,936, filed on Nov. 1, 2017.

(51) Int. Cl.
*A61K 31/4025* (2006.01)
*A61P 25/28* (2006.01)

(52) U.S. Cl.
CPC .......... *A61K 31/4025* (2013.01); *A61P 25/28* (2018.01)

(58) Field of Classification Search
CPC ...... A61P 25/28; A61K 31/445; A61K 31/365
See application file for complete search history.

(56) References Cited

U.S. PATENT DOCUMENTS

| | | | |
|---|---|---|---|
| 7,109,357 B2 | 9/2006 | Wannamaker et al. |
| 7,381,827 B2 | 6/2008 | Tanoury et al. |
| 7,417,029 B2 | 8/2008 | Wannamaker et al. |
| 7,531,570 B2 | 5/2009 | Randle |
| 7,834,200 B2 | 11/2010 | Tanoury et al. |
| 8,022,041 B2 | 9/2011 | Wannamaker et al. |
| 8,293,929 B2 | 10/2012 | Tanoury et al. |
| 8,329,662 B2 | 12/2012 | Wannamaker et al. |
| 8,497,369 B2 | 7/2013 | Himmelsbach et al. |
| 8,691,848 B2 | 4/2014 | Wannamaker et al. |
| 8,772,298 B2 | 7/2014 | Himmelsbach et al. |
| 9,116,157 B2 | 8/2015 | Ringe et al. |
| 9,156,880 B2 | 10/2015 | Wannamaker et al. |
| 9,352,010 B2 | 5/2016 | Greene et al. |
| 9,453,226 B2 | 9/2016 | Ambati et al. |
| 9,487,555 B2 | 11/2016 | Wannamaker et al. |
| 9,956,260 B1 | 5/2018 | Greene et al. |
| 9,994,613 B2 | 6/2018 | Wannamaker et al. |
| 2006/0148766 A1 | 7/2006 | Suh |

OTHER PUBLICATIONS

Pachalska et al., Med Sci Monit, 2015;21:3483-3489 (Year: 2015).*
Gemma et al., European Journal of Neuroscience, vol. 26, pp. 2795-2803, 2007 (Year: 2007).*
Gemma et al., European Journal of Neuroscience, vol. 22, pp. 1751-1756, 2005 (Year: 2005).*
Gemma, C. et al., "Improvement of memory for context by inhibition of caspase-1 in aged rats", European Journal of Neuroscience, 22(7):1751-1756, Oct. 1, 2005.
Gemma, C. et al., "Interleukin-1beta and caspase-1: players in the regulation of age-related cognitive dysfunction", Reviews in the Neurosciences, 18(2):137-148, Jan. 1, 2007.
Extended European Search Report, including the Supplementary European Search Report and European Search Opinion, in respect of European Application No. 17883876.9 (Leblanc, Andrea), dated Aug. 6, 2020.
Albrecht, S., et al., "Activation of caspase-6 in aging and mild cognitive impairment", American Journal of Pathology 170:4, 1200-1209 (2007).
Albrecht, S., et al., "Caspase-6 activation in familial Alzheimer disease brains carrying amyloid precursor protein or presenilin I or presenilin II mutations", Journal of Neuropathology and Experimental Neurology 68:12, 1282-1293 (2009).
Bassil, F., et al., "Reducing C-terminal truncation mitigates synucleinopathy and neurodegeneration in a transgenic model of multiple system atrophy", PNAS 113:34, 9593-9598 (2016).
Cotman, C.W., et al., "A Potential Role for Apoptosis in Neurodegeneration and Alzheimer's Disease", Molecular Neurology 10:19-45 (1995).
Dudchenko, P.A., et al., "Animal models of working memory: a review of tasks that might be used in screening drug treatments for the memory impairments found in schizophrenia", Neuroscience and biobehavioral reviews 37: 2111-2124 (2013).
Gagliardini, V., et al., "Prevention of vertebrate neuronal death by the crmA gene", Science 263: 826-828 (1994).
Gamblin, C.T., et al., "Caspase cleavage of tau: Linking amyloid and neurofibrillary tangles in Alzheimer's disease", PNAS 100:17, 10032-10037 (2003).

(Continued)

*Primary Examiner* — San Ming R Hui
(74) *Attorney, Agent, or Firm* — Lavery, De Billy, LLP; Sarkis Shahinian

(57) ABSTRACT

Described herein are methods for preventing, delaying the onset or reducing the severity of, preventing or reversing the progression of, or treating a neurological condition (e.g., a neurodegenerative disease (e.g., Alzheimer's disease)) in a subject, based on caspase-1 inhibition. Also described herein are methods for preventing, delaying the onset or reducing the severity of, preventing or reversing the progression of, or treating cognitive impairment in a subject, based on caspase-1 inhibition. Corresponding uses and kits are also described. In an embodiment, the caspase-1 inhibitor is VX-765 or a pharmaceutically acceptable salt thereof.

13 Claims, 42 Drawing Sheets

(56) References Cited

OTHER PUBLICATIONS

Grayson, B., et al., "Assessment of disease-related cognitive impairments using the novel object recognition (NOR) task in rodents", Behavioural Brain Research 285: 176-193 (2015).

Halle, A., et al., "The NALP3 inflammasome is involved in the innate immune response to amyloid-β", Nature Immunology 9: 857-865 (2008).

Howley, B., et al., "Caspases as therapeutic targets", Journal of Cellular and Molecular Medecine 12:5A, 1502-1516 (2008).

International Search Report (ISR) and Written Opinion in respect of PCT/CA2017/051548.

Kaushal, V., et al., "Neuronal NLRP1 inflammasome activation of Caspase-1 coordinately regulates inflammatory interleukin-1-beta production and axonal degeneration-associated Caspase-6 activation", Cell Death and Differentiation 22: 1676-1686 (2015).

Keller, M., et al., "Active caspase-1 is a regulator of unconventional protein secretion", Cell 132: 818-831 (2008).

LeBlanc, A.C., "The Role of Apoptotic Pathways in Alzheimer's Disease Neurodegeneration and Cell Death", Current Al-heimer Research 2: 1-14 (2005).

Maroso, T., et al., "Interleukin-1β Biosynthesis Inhibition Reduces Acute Seizures and Drug Resistant Chronic Epileptic Activity in Mice", Neurotherapeutics: The Journal of the American Society for Experimental NeuroTherapeutics 8:2, 304-311 (2011).

Miura, M., et al., "Induction of apoptosis in fibroblasts by IL-1 beta-converting enzyme, a mammalian homolog of the C. elegans cell death gene ced-3", Cell 75: 653-660 (1993).

Nett-Fiordalisi, M., et al., "Macrophage apoptosis in the absence of active interleukin-1 beta-converting enzyme", Journal of Leukocyte Biology 58: 717-24 (1995).

Paylor, R., et al., "The use of behavioral test batteries, II: effect of test interval", Physiology & Behavior 87: 95-102 (2006).

Pompl, P.N., et al., "Caspase gene expression in the brain as a function of the clinical progression of Alzheimer disease", Archives of Neurology 60: 369-376 (2003).

Rohn, T.T., et al., "Caspases as Therapeutic Targets in Alzheimer's Disease: Is It Time to "Cut" to the Chase?", International Journal of Clinical and Experimental Pathology 2: 108-118 (2009).

Troy, C.M., et al., "Caspases: Therapeutic Targets in Neurologic Disease", Neurotherapeutics 12:42-48 (2015).

Vigano, E., et al., "Human caspase-4 and caspase-5 regulate the one-step non-canonical inflammasome activation in monocytes", Nature Communications 6, Article No. 8761, 1-13 (2005).

Wannamaker, W., et al., "(S)-1-((S)-2-{[1-(4-amino-3-chloro-phenyl)-methanoyl]-amino}-3,3-dimethyl-butanoy I)-pyrrolidine-2-carboxylic acid ((2R,3S)-2-ethoxy-5-oxo-tetrahydro-furan-3-yl)-amide (VX-765), an orally available selective interleukin (IL)-converting enzyme/caspase-1 inhibitor, exhibits potent anti-inflammatory activities by inhibiting the release of IL-1beta and IL-18.", The Journal of Pharmacology and Experimental Therapeutics 321:2, 509-516 (2007).

Yuan, J. et al., "The C. elegans cell death gene ced-3 encodes a protein similar to mammalian interleukin-1 beta-converting enzyme", Cell 75: 641-652 (1993).

International Preliminary Report on Patentability (IPRP) in respect of PCT/CA2017/051548.

Coeshott, C., et al. (1999). Converting enzyme-independent release of tumor necrosis factor alpha and IL-1beta from a stimulated human monocytic cell line in the presence of activated neutrophils or purified proteinase 3. Proceedings of the National Academy of Sciences of the United States of America, vol. 96, pp. 6261-6266.

Heneka, M. T., et al. (2013). NLRP3 is activated in Alzheimer's disease and contributes to pathology in APP/PS1 mice. Nature, vol. 493, pp. 674-678.

LaSarge, C. L., et al. (2007). Deficits across multiple cognitive domains in a subset of aged Fischer 344 rats. Neurobiology of aging, vol. 28, pp. 928-936.

Rozman-Pungercar, J., et al. (2003). Inhibition of papain-like cysteine proteases and legumain by caspase-specific inhibitors: when reaction mechanism is more important than specificity. Cell death and differentiation, vol. 10, pp. 881-888.

Sugawara, S., et al. (2001). Neutrophil proteinase 3-mediated induction of bioactive IL-18 secretion by human oral epithelial cells. Journal of immunology, vol. 167, pp. 6568-6575.

Crawley J.N. (2007) What's Wrong With My Mouse? Behavioral Phenotyping of Transgenic and Knockout Mice, Second edition, 2007, John Wiley & Sons, Inc., pp. 126-131.

* cited by examiner

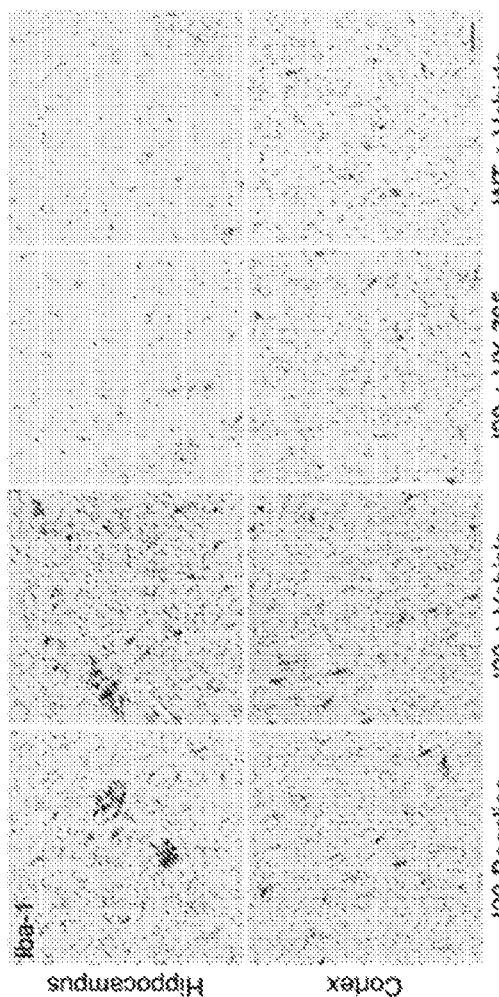
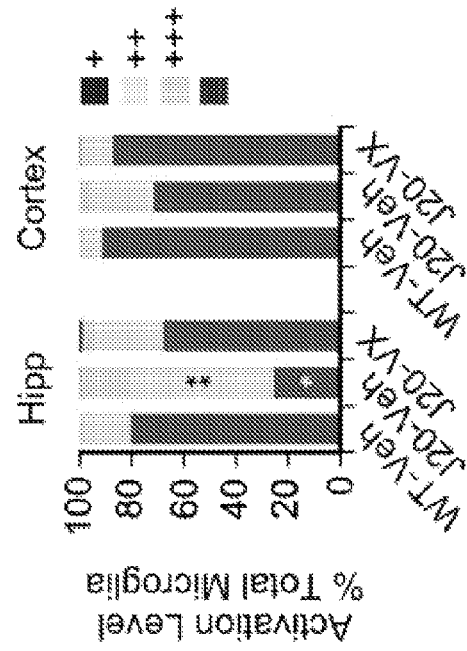
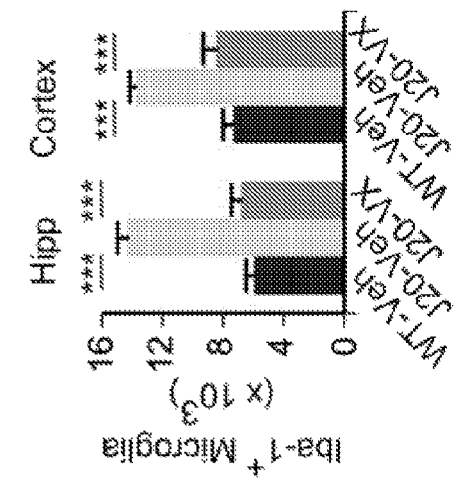
FIG. 10a
FIG. 10b
FIG. 10c

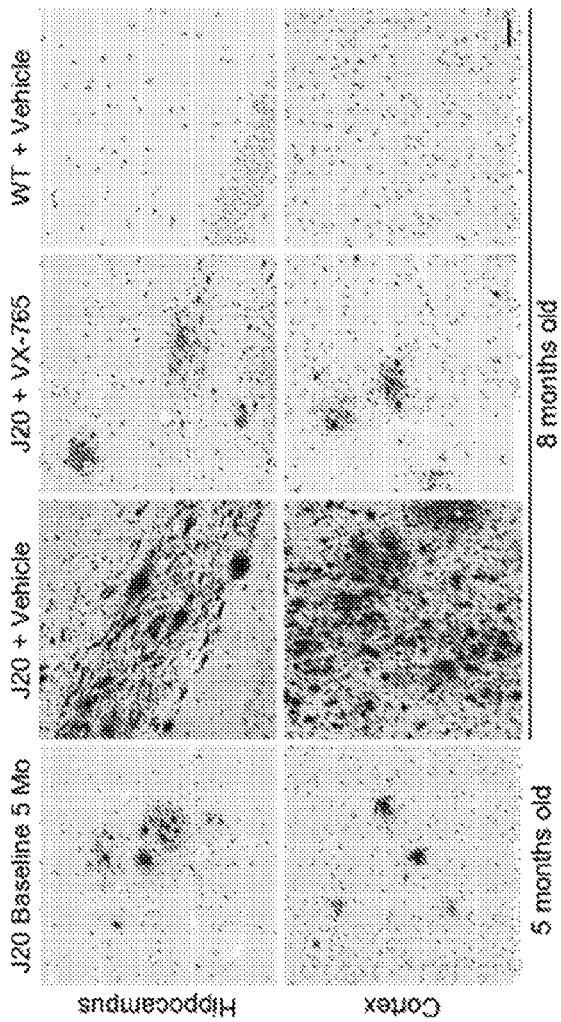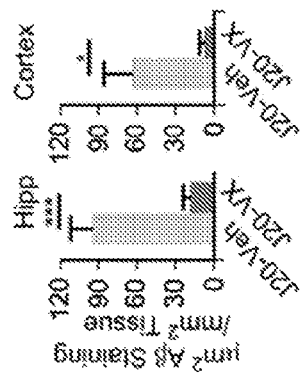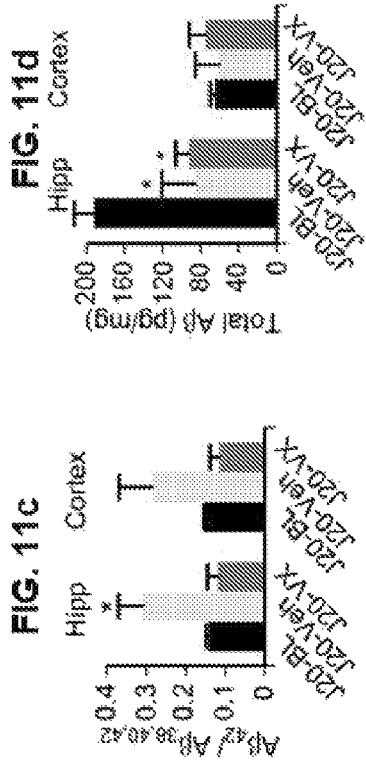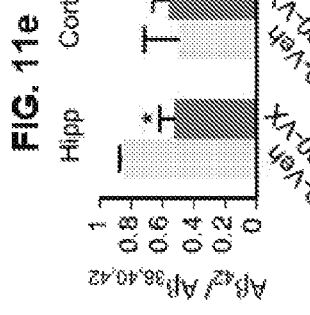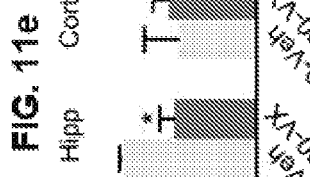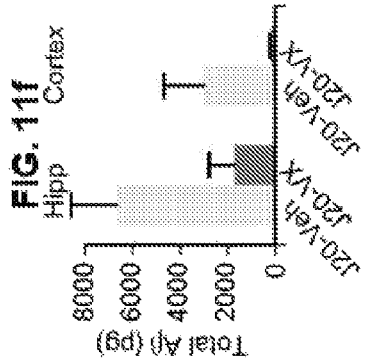

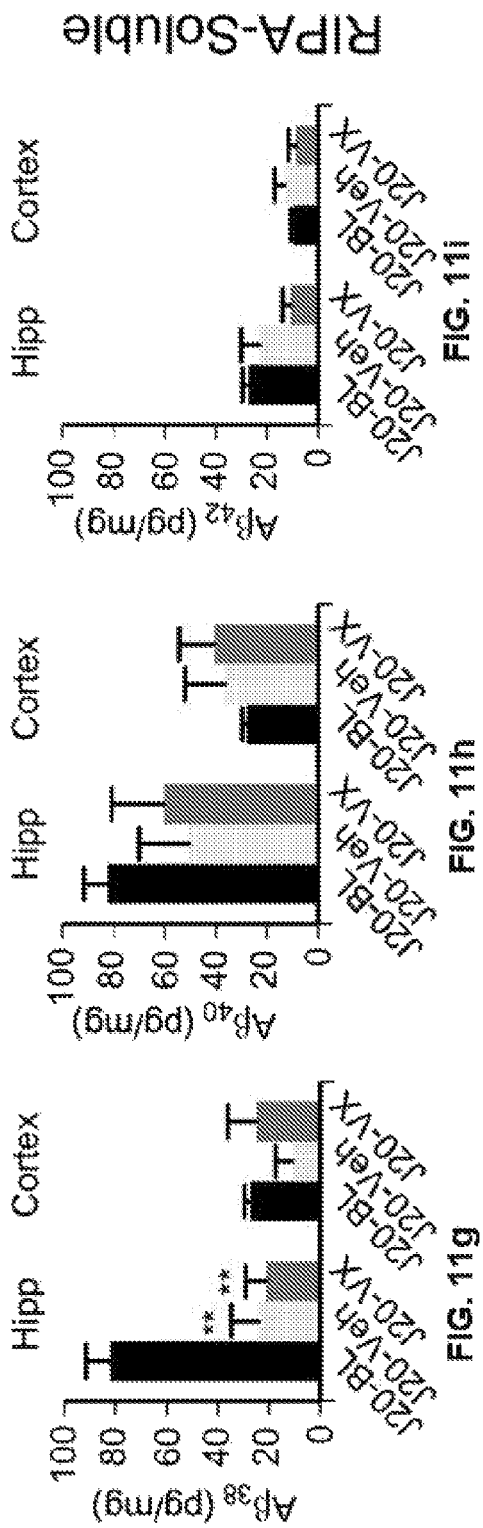

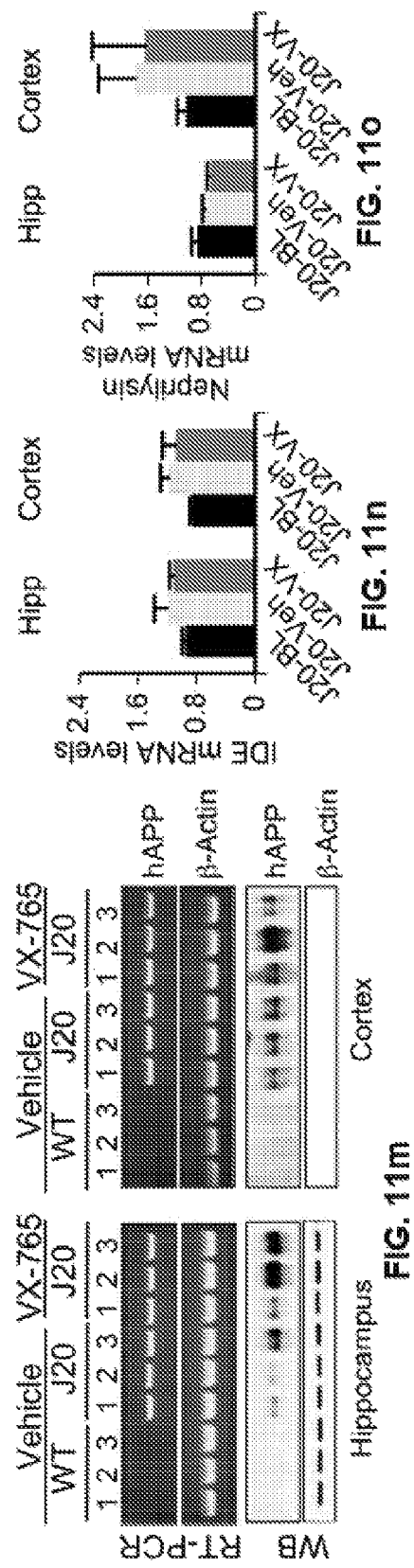

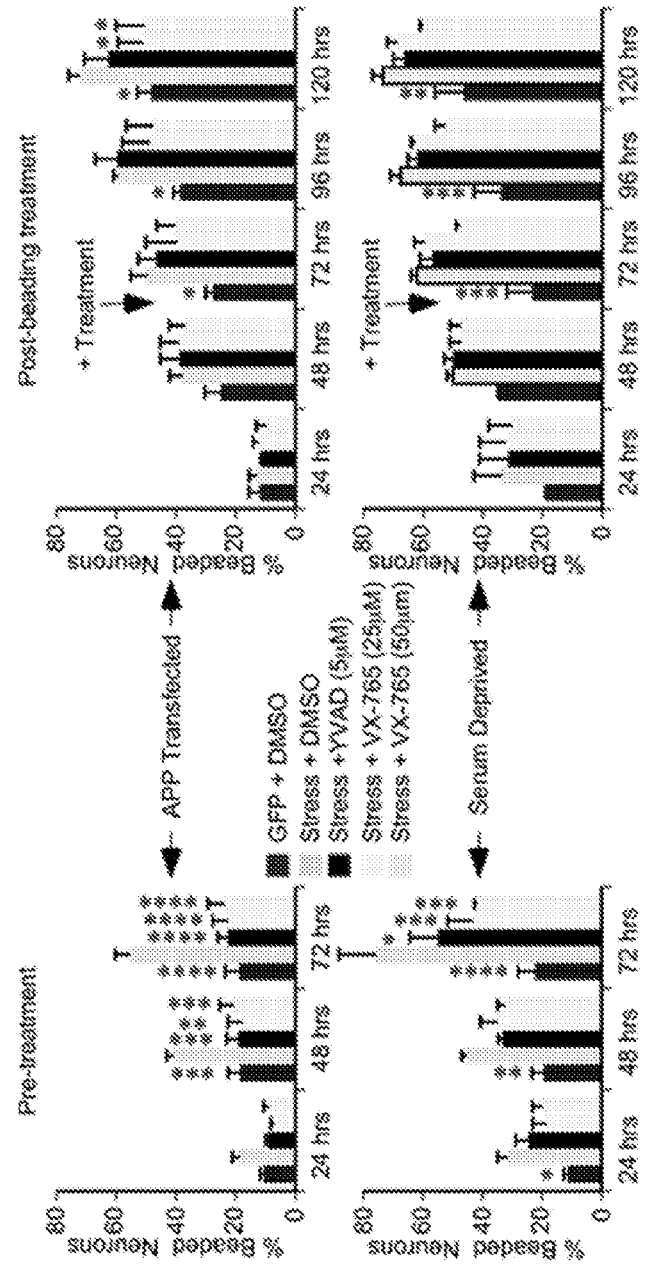
FIG. 13a
FIG. 13b
FIG. 13c

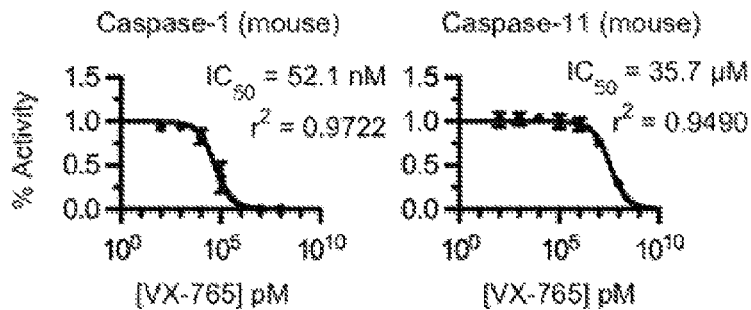
FIG. 14c
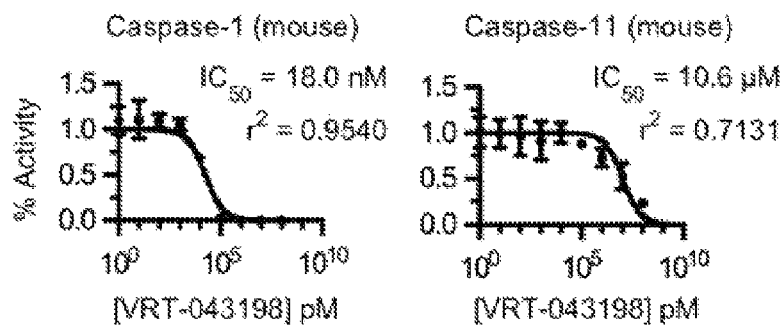
FIG. 14d
| VX-765 | Brain Cortex µM | Brain Hippo µM | Plasma (µM) | Ratio (Cortex) | Ratio (Hippo) |
|---|---|---|---|---|---|
| WT Mice | 4.626 | 0.877 | 26.932 | 0.172 | 0.033 |
|  | 0.378 | 0.654 | 14.762 | 0.026 | 0.044 |
|  | 0.431 | 11.500 | 10.839 | 0.040 | 1.061 |
| J20 Mice | 1.345 | 0.709 | 6.688 | 0.201 | 0.106 |
|  | 0.648 | 0.913 | 8.173 | 0.079 | 0.112 |
|  | 0.647 | 1.109 | 8.790 | 0.074 | 0.126 |
|  | 0.403 | 5.700 | 6.710 | 0.060 | 0.849 |
| VRT-043189 | Brain Cortex µM | Brain Hippo µM | Plasma (uM) | Ratio (Cortex) | Ratio (Hippo) |
|---|---|---|---|---|---|
| WT Mice | 7.336 | 2.482 | 953.900 | 0.008 | 0.003 |
|  | 1.462 | 3.373 | 1202.700 | 0.001 | 0.003 |
|  | 1.980 | 20.164 | 1250.600 | 0.002 | 0.016 |
| J20 Mice | 4.041 | 3.342 | 720.550 | 0.006 | 0.005 |
|  | 3.037 | 3.524 | 885.060 | 0.003 | 0.004 |
|  | 2.191 | 2.564 | 1199.600 | 0.002 | 0.002 |
|  | 1.069 | 10.437 | 874.660 | 0.001 | 0.012 |
FIG. 14e

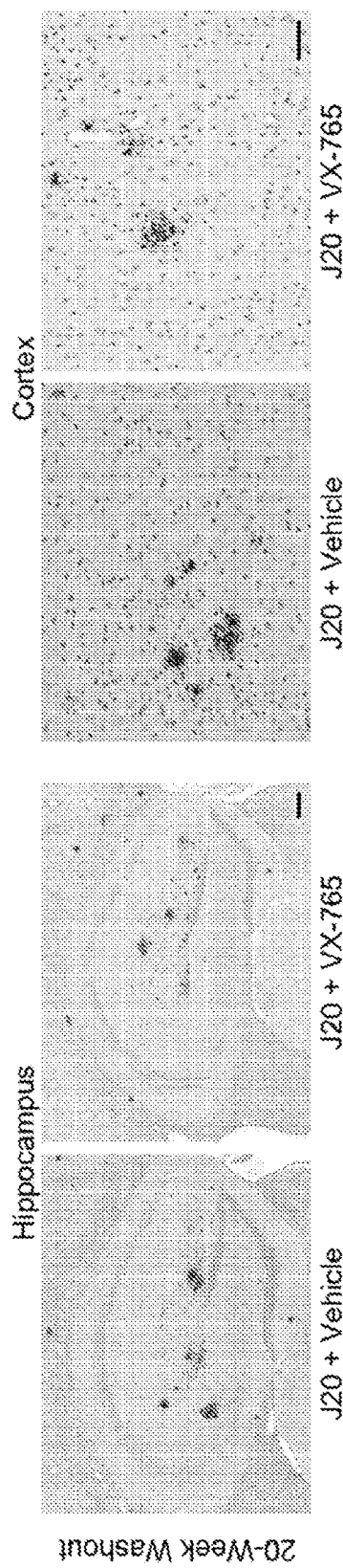
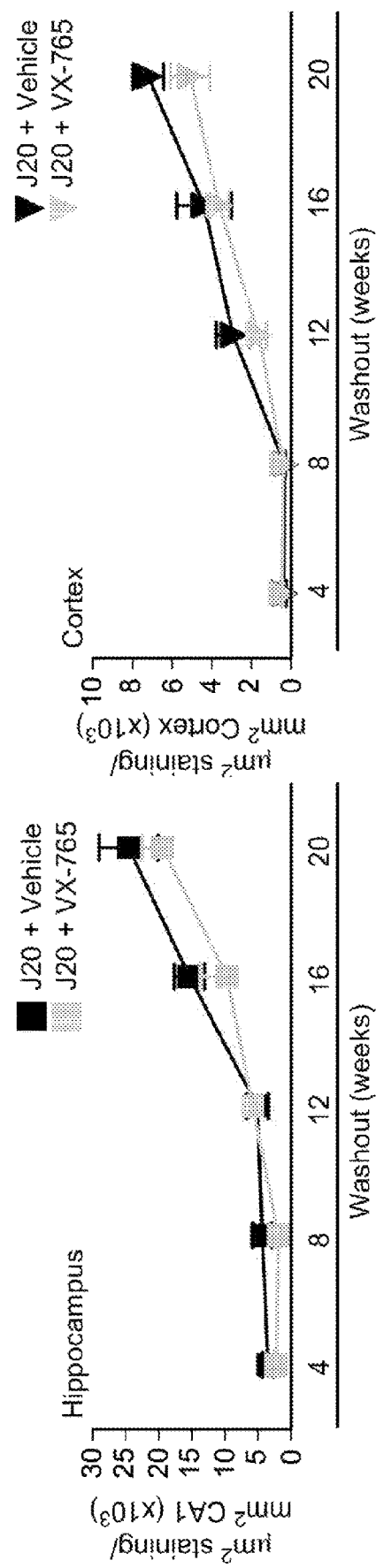
FIG. 24a
FIG. 24b

CASPASE-1 INHIBITION AND USES THEREOF FOR PREVENTION AND TREATMENT OF NEUROLOGICAL CONDITIONS

CROSS REFERENCE TO RELATED APPLICATIONS

This application claims priority is a National Stage Application of PCT Application No. PCT/CA2017/051548 filed on Dec. 20, 2017 and published in English under PCT Article 21(2), which claims the benefit of U.S. provisional application Ser. No. 62/438,529 filed on Dec. 23, 2016 and U.S. provisional application Ser. No. 62/579,936 filed on Nov. 1, 2017. All documents above are incorporated herein by reference in their entirety.

TECHNICAL FIELD

The present invention generally relates to prevention and treatment of neurological conditions, such as neurodegenerative disease or cognitive impairment, and more particularly relates to such prevention and treatment based on caspase-1 inhibition.

BACKGROUND ART

Neurodegenerative diseases affect millions worldwide, becoming more and more prominent with an increasingly aging population. Alzheimer's disease (AD) in particular is very common amongst elderly subjects, and is characterized by a progressive decline in memory loss and other cognitive functions. Neuropathologies of the disease include the accumulation of neurofibrillary tangles, β-amyloid-containing plaques, dystrophic neurites, and loss of synapses and neurons (Selkoe, D. et al., 1999, Alzheimer's Disease, $2^{nd}$ Ed., Terry R. et al., eds. pg. 293-310. Philadelphia: Lippincott, Williams and Wilkins).

Dementia, of which Alzheimer Disease is the principal cause, affects 47.5 million individuals worldwide and an additional 7.7 million cases is diagnosed each year, according to the World Health Organisation. Only a limited number of pharmacological agents have been identified for treating symptoms of AD. The most prominent of these today are galantamine, rivastigmine, and donepezil hydrochloride, which are cholinesterase inhibitors active in the brain, and memantine, which targets the N-methyl-D-aspartate glutamate receptor. These drugs have modest effects in slowing the progression of the disease Furthermore, no compound has been established as effective in blocking the development or progression of AD.

Cognitive impairment affects more than 16 million people in the US alone. A person suffering from cognitive impairment will have trouble remembering, learning new things, concentrating, or making everyday decisions. Cognitive impairment is not caused by any one disease condition, is not limited to a particular age group. Severity ranges from low levels, in which people may begin to notice changes in cognitive functions but still be able to do their everyday activities, to severe levels, which can lead to losing the ability to understand the meaning or importance of something and the ability to talk or write, resulting in the inability to live independently.

There is thus a need for novel compositions and methods for the treatment of neurological conditions, such as neurodegenerative disease or cognitive impairment.

The present description refers to a number of documents, the content of which is herein incorporated by reference in their entirety.

SUMMARY OF THE INVENTION

The present invention generally relates to prevention and treatment of neurological conditions, such as neurodegenerative disease or cognitive impairment, and more particularly relates to such prevention and treatment based on caspase-1 inhibition.

In an aspect, the present invention relates to a method of preventing, delaying the onset or reducing the severity of, preventing or reversing the progression of, or treating a neurological condition (e.g., a neurodegenerative disease) in a subject, said method comprising administering a caspase-1 inhibitor to the subject.

The present invention also relates to a use of a caspase-1 inhibitor for preventing, delaying the onset or reducing the severity of, preventing or reversing the progression of, or treating a neurological condition (e.g., a neurodegenerative disease) in a subject.

The present invention also relates to a use of a caspase-1 inhibitor for the preparation of a medicament for preventing, delaying the onset or reducing the severity of, preventing or reversing the progression of, or treating a neurological condition (e.g., a neurodegenerative disease) in a subject.

The present invention also relates to a caspase-1 inhibitor for use in preventing, delaying the onset or reducing the severity of, preventing or reversing the progression of, or treating a neurological condition (e.g., a neurodegenerative disease) in a subject.

The present invention also relates to a kit comprising a caspase-1 inhibitor, or a composition comprising the caspase-1 inhibitor and a pharmaceutically acceptable carrier, for use in preventing, delaying the onset or reducing the severity of, preventing or reversing the progression of, or treating a neurological condition (e.g., a neurodegenerative disease) in a subject.

In a further aspect, the present invention also relates to a method of preventing, delaying the onset or reducing the severity of, preventing or reversing the progression of, or treating cognitive impairment in a subject, said method comprising administering a caspase-1 inhibitor to the subject.

The present invention also relates to a use of a caspase-1 inhibitor for preventing, delaying the onset or reducing the severity of, preventing or reversing the progression of, or treating cognitive impairment in a subject.

The present invention also relates to a use of a caspase-1 inhibitor for the preparation of a medicament for preventing, delaying the onset or reducing the severity of, preventing or reversing the progression of, or treating cognitive impairment in a subject.

The present invention also relates to a caspase-1 inhibitor for use in preventing, delaying the onset or reducing the severity of, preventing or reversing the progression of, or treating cognitive impairment in a subject.

The present invention also relates to a kit comprising a caspase-1 inhibitor, or a composition comprising the caspase-1 inhibitor and a pharmaceutically acceptable carrier, for use in preventing, delaying the onset or reducing the severity of, preventing or reversing the progression of, or treating cognitive impairment in a subject.

In an embodiment, the caspase-1 inhibitor is a compound having Formula I:

wherein $R^1$ is

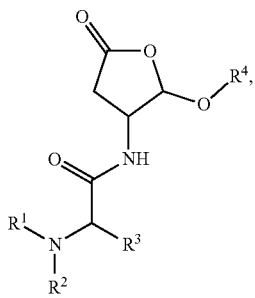

$R^2$ and $R^3$ taken together form a ring, wherein said ring is:

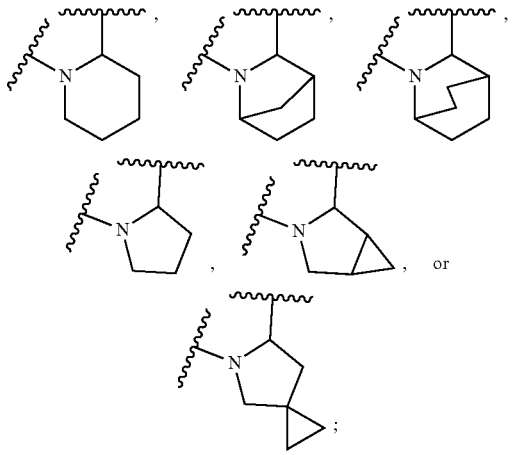

wherein, in each ring, any hydrogen atom is optionally and independently replaced by $R^7$ and any set of two hydrogen atoms bound to the same atom is optionally and independently replaced by carbonyl;

when the ring formed by $R^2$ and $R^3$ is

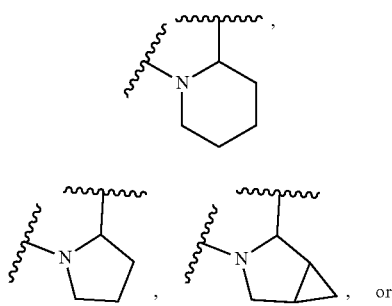

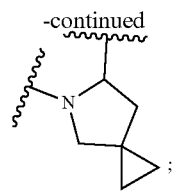

then
$R^5$ is $R^8C(O)$—, and
$R^8$ is phenyl, thiophene, or pyridine, wherein each ring is optionally substituted with up to 5 groups independently selected from $R^9$, and wherein at least one position on the phenyl, thiophene, or pyridine is substituted by $R^{10}$;
when the ring formed by $R^2$ and $R^3$ is

then
$R^5$ is $R^8C(O)$—, HC(O), $R^8SO_2$—, $R^8OC(O)$, $(R^8)_2NC(O)$, $(R^8)(H)NC(O)$, $R^8C(O)C(O)$—, $R^8$—, $(R^8)_2NC(O)C(O)$, $(R^8)(H)NC(O)C(O)$, or $R^8OC(O)C(O)$—; and
$R^8$ is $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic)-$(C_{1-12}$aliphatic)-, $(C_{6-10}$aryl)-$(C_{1-12}$aliphatic)-, (5-10 membered heterocyclyl)-$(C_{1-12}$aliphatic)-, or (5-10 membered heteroaryl)-$(C_{1-12}$aliphatic)-; or two $R^8$ groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, $NR^{11}$, S, SO, and $SO_2$, wherein $R^8$ is substituted with up to 6 substituents independently selected from $R^{12}$;
$R^4$ is H, $C_{1-12}$aliphatic, $C_{3-10}$cycloaliphatic, $C_{6-10}$aryl, 5-10 membered heterocyclyl, 5-10 membered heteroaryl, $(C_{3-10}$cycloalkyl)-$(C_{1-12}$aliphatic)-, cycloalkenyl-$(C_{1-12}$aliphatic)-, $(C_{6-10}$aryl)-$(C_{1-12}$aliphatic)-, (5-10 membered heterocyclyl)-$(C_{1-12}$aliphatic)-, or (5-10 membered heteroaryl)-$(C_{1-12}$aliphatic)-, wherein any hydrogen atom is optionally and independently replaced by $R^{12}$ and any set of two hydrogen atoms bound to the same atom is optionally and independently replaced by carbonyl;
$R^6$ is —$C(R^{13})(R^{14})(R^{15})$, $C_{6-10}$aryl, 5-10 membered heteroaryl, or $C_{3-7}$cycloalkyl;
$R^7$ is halogen, —$OR^{11}$, —$NO_2$—CN—$CF_3$, —$OCF_1$, —$R^{11}$, 1,2-methylenedioxy, 1,2-ethylenedioxy, —$N(R^{11})_2$, —$SR^{11}$, —$SOR^{11}$, —$SO_2R^{11}$—$SO_2N(R^{11})_2$, —$SO_3R^{11}$, —$C(O)R^{11}$, —$C(O)C(O)R^{11}$, —$C(O)C(O)OR^{11}$, —$C(O)C(O)N(R^{11})_2$, —$C(O)CH_2C(O)R^{11}$, —$C(S)R^{11}$, —$C(S)OR^{11}$, —$C(O)OR^{11}$, —$OC(O)R^{11}$, —$C(O)N(R^{11})_2$, —$OC(O)N(R^{11})_2$, —$C(S)N(R^{11})_2$, —$(CH_2)_{0-2}NHC(O)R^{11}$, —$N(R^{11})N(R^{11})COR^{11}$, —$N(R^{11})N(R^{11})C(O)OR^{11}$, —$N(R^{11})N(R^{11})CON(R^{11})_2$, —$N(R^{11})SO_2R^{11}$, —$N(R^{11})SO_2N(R^{11})_2$, —$N(R^{11})C(O)OR^{11}$, —$N(R^{11})C(O)R^{11}$, —$N(R^{11})C(S)R^{11}$, —$N(R^{11})C(O)N(R^{11})_2$, —$N(R^{11})C(S)N(R^{11})_2$—$N(R^{11})COR^{11}$, —$N(OR^{11})R^{11}$, —$C(=NH)N(R^{11})_2$, —$C(O)N(OR^{11})R^{11}$, —$C(=NOR^{11})R^{11}$, —$OP(O)(OR^{11})_2$, —$P(O)(R^{11})_2$, —$P(O)(OR^{11})_2$, or —$P(O)(H)(OR^{11})$;

$R^9$ and $R^{12}$ are each independently halogen, —$OR^{11}$, —$NO_2$, —CN, —$CF_3$, —$OCF_3$, —$R^{11}$, 1,2-methylenedioxy, 1,2-ethylenedioxy, —$N(R^{11})_2$, —$SR^{11}$, —$SOR^{11}$, —$SO_2R^{11}$, —$SO_2N(R^{11})_2$—$SO_3R^{11}$, —$C(O)R^{11}$, —$C(O)C(O)R^{11}$, —$C(O)C(O)OR^{11}$, —$C(O)C(O)N(R^{11})_2$, —$C(O)CH_2C(O)R^{11}$, —$C(S)R^{11}$, —$C(S)OR^{11}$, —$C(O)OR^{11}$, —$OC(O)R^{11}$, —$C(O)N(R^{11})_2$, —$OC(O)N(R^{11})_2$, —$C(S)N(R^{11})_2$, —$(CH_2)_{0-2}NHC(O)R^{11}$, —$N(R^{11})N(R^{11})COR^{11}$, —$N(R^{11})N(R^{11})C(O)OR^{11}$, —$N(R^{11})N(R^{11})CON(R^{11})_2$, —$N(R^{11})SO_2R^{11}$, —$N(R^{11})SO_2N(R^{11})_2$, —$N(R^{11})C(O)OR^{11}$, —$N(R^{11})C(O)R^{11}$, —$N(R^{11})C(S)R^{11}$, —$N(R^{11})C(O)N(R^{11})_2$, —$N(R^{11})C(S)N(R^{11})_2$, —$N(COR^{11})COR^{11}$, —$N(OR^{11})R^{11}$, —$C(=NH)N(R^{11})_2$, —$C(O)N(OR^{11})R^{11}$, —$C(=NOR^{11})R^{11}$, —$OP(O)(OR^{11})_2$, —$P(O)(R^{11})_2$, —$P(O)(OR^{11})_2$, or —$P(O)(H)(OR^{11})$;

$R^{10}$ is halogen, —$OR^{17}$, —$NO_2$—CN—$CF_3$—$OCF_3$, —$R^{17}$, or —$SR^{11}$, wherein $R^{10}$ has no more than 5 straight-chained atoms;

$R^{11}$ is hydrogen, $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic)-, ($C_{6-10}$aryl)-($C_{1-12}$aliphatic)-, (5-10 membered heterocyclyl)-($C_{1-12}$aliphatic)-, or heteroaryl-($C_{1-12}$aliphatic)-; wherein any hydrogen atom is optionally and independently replaced by $R^{18}$ and any set of two hydrogen atoms bound to the same atom is optionally and independently replaced by carbonyl;

$R^{13}$ is H or a $C_{1-6}$ straight-chained or branched alkyl;

$R^{14}$ is H or a $C_{1-6}$ straight-chained or branched alkyl;

$R^{15}$ is —$CF_3$, —$C_{3-7}$cycloalkyl, $C_{6-10}$aryl, 5-10 membered heteroaryl, heterocycle, or a $C_{1-6}$ straight-chained or branched alkyl, wherein each carbon atom of the alkyl is optionally and independently substituted with $R^{16}$;

or $R^{13}$ and $R^{15}$ taken together with the carbon atom to which they are attached form a 3-10 membered cycloaliphatic;

$R^{16}$ is halogen, —$OR^{17}$, —$NO_2$, —CN, —$CF_3$—$OCF_3$, —$R^{17}$, or —$SR^{17}$; wherein $R^{17}$ is $C_{1-4}$-aliphatic-;

$R^{17}$ is $C_{1-4}$-aliphatic-; and $R^{18}$ is —$OR^{17}$, —$NO_2$, —CN, —$CF_3$, —$OCF_3$, —$R^{17}$, 1,2-methylenedioxy, 1,2-ethylenedioxy, —$N(R^{17})_2$,—$SR^{17}$, —$SOR^{17}$, —$SO_7R^{17}$—$SO_2N(R^{17})_2$—$SO_3R^{17}$, —$C(O)R^{17}$, —$C(O)C(O)R^{17}$, —$C(O)C(O)OR^{17}$, —$C(O)C(O)N(R^{17})_2$, —$C(O)CH_2C(O)R^{17}$—$C(S)R^{17}$, —$C(S)OR^{17}$, —$C(O)OR^{17}$, —$OC(O)R^{17}$, —$C(O)N(R^{17})_2$, —$OC(O)N(R^{17})_2$, —$C(S)N(R^{17})_2$, —$(CH_2)_{0-2}NHC(O)R^{17}$, —$N(R^{17})N(R^{17})COR^{17}$, —$N(R^{17})N(R^{17})C(O)OR^{17}$, —$N(R^{17})N(R^{17})CON(R^{17})_2$, —$N(R^{17})SO_2R^{17}$, —$N(R^{17})SO_2N(R^{17})_2$, —$N(R^{17})C(O)OR^{17}$, —$N(R^{17})C(O)R^{17}$, —$N(R^{17})C(S)R^{17}$, —$N(R^{17})C(O)N(R^{17})_2$, —$N(R^{17})C(S)N(R^{17})_2$, —$N(COR^{17})COR^{17}$, —$N(OR^7)R^{17}$, —$C(=NH)N(R^{17})_2$, —$C(O)N(OR^7)R^{17}$, —$C(=NOR^{17})R^{17}$, —$OP(O)(OR^{17})_2$, —$P(O)(R^{17})_2$, —$P(O)(OR^{17})_2$, or —$P(O)(H)(OR^{17})$; $R^{17}$ is hydrogen, $C_{1-12}$aliphatic, $C_{3-10}$cycloaliphatic, $C_{6-10}$aryl, 5-10 membered heterocyclyl, 5-10 membered heteroaryl, ($C_{3-10}$cycloaliphatic)-($C_{1-12}$aliphatic), ($C_{6-10}$aryl)-($C_{1-12}$aliphatic)-, (5-10 membered heterocyclyl)-($C_{1-12}$aliphatic)-, or heteroaryl-($C_{1-12}$aliphatic)-;

or single stereoisomers, mixtures of stereoisomers, or pharmaceutically acceptable salts thereof.

In an embodiment, the caspase-1 inhibitor is a compound of Formula II:

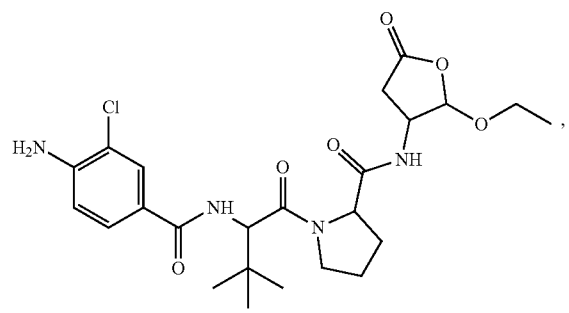

II or single stereoisomers, mixtures of stereoisomers, or pharmaceutically acceptable salts thereof.

In an embodiment, the caspase-1 inhibitor is VX-765 or a pharmaceutically acceptable salt thereof.

In an embodiment, the neurodegenerative disease is Alzheimer's Disease (AD).

In embodiments, the methods, uses and kits are for the reversal or prevention of cognitive deficits, such as a memory deficit, associated with the neurological condition (e.g., a neurodegenerative disease (e.g., AD)).

In embodiments, the methods, uses and kits are for the prevention, reversal, and/or decrease of production, formation, aggregation and/or deposition of Aβ (e.g. Aβ$_{42}$), associated with the neurological condition (e.g., a neurodegenerative disease (e.g., AD)). In an embodiment, such prevention, reversal, and/or decrease of production, formation, aggregation and/or deposition of Aβ (e.g. Aβ$_{42}$) occurs without decreasing APP levels.

In embodiments, the methods, uses and kits are for the reversal or prevention of the progression of cognitive deficits, such as a memory deficit, associated with the neurological condition (e.g., a neurodegenerative disease (e.g., AD)), i.e. to reverse or prevent the progression of such cognitive deficits to worse cognitive deficit.

In an embodiment, the subject is pre-symptomatic for the neurological condition (e.g., a neurodegenerative disease). In an embodiment, the subject suffers from subjective cognitive impairment. In an embodiment, the subject suffers from mild cognitive impairment. In an embodiment, the subject has:

(a) increased amyloid and tau pathology in the brain;
(b) atrophied hippocampus;
(c) amyloid, Tau and/or inflammatory biomarker profiles indicative of progression to the neurodegenerative disease;
(d) a neuropsychological profile indicative of age-dependent cognitive impairment or Alzheimer disease;
(e) other neuroimaging or biochemical (blood, CSF) biomarkers indicative of age-dependent cognitive impairment or Alzheimer disease; or
(f) any combination of (a)-(e).

In an embodiment, the subject suffers from neuroinflammation in the brain associated with cognitive impairment.

In an embodiment, the subject has a genetic mutation associated with familial Alzheimer Disease.

In an embodiment, the cognitive impairment is mild cognitive impairment.

In an embodiment, the cognitive impairment is subjective cognitive impairment.

In an embodiment, the cognitive impairment is age-dependent cognitive impairment.

In an embodiment, the cognitive impairment comprises one or more of a memory deficit, an inability to recognize faces or places, repetitive questioning, trouble with learning, trouble with exercising judgment, change in mood or behaviour, vision problems, and difficulty in carrying out daily living tasks.

In an embodiment, the subject has a neuropsychological profile indicative of age-dependent cognitive impairment.

In an embodiment, the subject suffers from neuroinflammation in the brain associated with cognitive impairment.

In an embodiment, the subject is a mammal, in a further embodiment, a human.

In an embodiment, the caspase-1 inhibitor is comprised in a composition comprising the caspase-1 inhibitor and a pharmaceutically acceptable carrier.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

FIG. 11: VX-765 prevents the progression of A$\beta$ in J20 mice. (a) A$\beta$ immunohistographs of the stratum lacunosum molecular layer of the hippocampus and S1 cortex of pre-treated 5-month old J20 (baseline) and 8-month old vehicle- or VX-765-treated WT or J20 mice with anti-F2576 antiserum (Scale bar=50 μm). (b) Quantitative analysis comparing Aβ immunostaining density between J20+Vehicle (n=5) and J20+VX-765 (n=4) mice in the hippocampus from the pyramidal cell layer to the stratum lacunosum molecular layer (p=0.0029) and cortex (p=0.0314, unpaired t test). (c) Quantitative analysis comparing RIPA-soluble A$β_{42}$ over total Aβ (A$β_{38}$+A$β_{40}$+A$β_{42}$) levels in pre-treated 5-month old J20, 8-month old vehicle- or VX-765 treated J20 mice hippocampus (F(2,9)=6.614, p=0.0171, ANOVA, Tukey's post-hoc, * p<0.05). No ELISA signal was obtained from WT mice brains. (d) RIPA-soluble total Aβ measured by ELISA in pg/mg brain tissue. (e,f) Formic acid soluble A$β_{42}$ over total Aβ (A$β_{38}$+A$β_{40}$+A$β_{42}$) (e) and total Aβ (f) levels measured by ELISA in pg/mg brain tissue. Student t-test used to assess difference between J20+vehicle and J20+VX-765. (g,h,i) RIPA-soluble and (j,k,l) formic acid soluble A$β_{38}$, A$β_{40}$, and A$β_{42}$ measured by ELISA in pg/mg brain tissue. (m) APP mRNA and protein levels and (n) insulin degrading enzyme (IDE) and neprilysin mRNA levels (o) in hippocampus and cortex.

DISCLOSURE OF INVENTION

Figure 1:
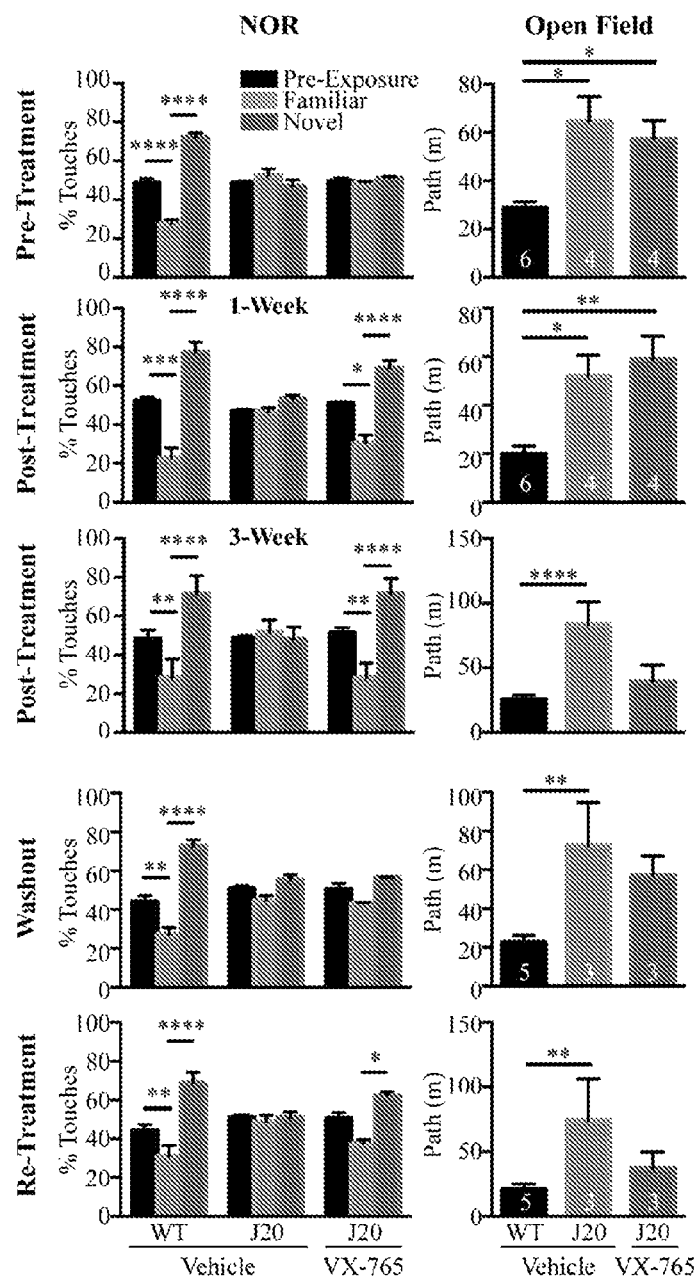
FIG. 1: Novel object recognition tests on littermate wild type (WT) and J20 mice treated with vehicle or 50 mg/Kg VX-765 by intraperitoneal (IP) injections as indicated (TREATMENT GROUPS). Pre-exposure: Pre-exposure to NOR box with 2 familiar object, Familiar: Number of touches of the familiar object during test with one familiar and one novel object, Novel: number of touches of the novel object. The number of mice used is indicated in the bars. One mouse per group was sacrificed before the washout to verify efficiency of drug. *$p<0.05$,  $p<0.01$, *$p<0.001$, ****$p<0.0001$

The present invention relates to preventing, delaying the onset or reducing the severity of, preventing or reversing the progression of, or treating a neurological condition (e.g., a neurodegenerative disease, such as Alzheimer's disease (AD)), based on caspase-1 inhibition. The present invention also relates to preventing, delaying the onset or reducing the severity of, preventing or reversing the progression of, or treating cognitive impairment, based on caspase-1 inhibition. In embodiments, the methods, uses and kits described herein are to delay onset, reduce severity or reverse cognitive impairment, such as a memory deficit, which in some cases may be associated with the neurological condition (e.g., a neurodegenerative disease (e.g., AD)).

Caspase-1 (Casp1, also known as interleukin-1 converting enzyme or ICE; EC 3.4.22.36; for a review, see Caspase-1: the inflammasome and beyond. Sollberger G. et al. *Innate Immun.* 20(2):115-25 (2014)) is a protease involved in the proteolytic activation of IL-1β and IL-18 (cleaving their precursors to yield the mature peptides), which are cytokines having a significant role in immune function. Caspase-1 exists as a zymogen which is cleaved to produce 2 subunits, p20 and p10, the active enzyme being a heterotetramer of 2 heterodimers, each containing a p20 and a p10 subunit. Further, various caspase-1 isoforms exist (see e.g. Uniprot-P29466).

Caspase-1 Inhibitors

As used herein, "caspase-1 inhibitor" refers to any compound or composition that directly or indirectly inhibits caspase-1 expression and/or activity. Without being so limited, candidate compounds modulating caspase-1 expression and/or activity are tested using a variety of methods and assays. It includes molecules such as, without being so limited, siRNA, antisense molecule, protein, peptide, small molecule, antibody, etc.

As used herein, "inhibition" or "decrease" of caspase-1 expression and/or activity refers to a reduction in caspase-1 expression level or activity level of at least 5% as compared to reference caspase-1 expression and/or activity (e.g., a measurement of caspase-1 expression and/or activity in a cell or tissue of the subject before treatment with a caspase-1 inhibitor). In an embodiment, the reduction in caspase-1 expression level or activity level is of at least 10% lower, in a further embodiment, at least 15% lower, in a further embodiment, at least 20% lower, in a further embodiment of at least 30% lower, in a further embodiment of at least 40% lower, in a further embodiment of at least 50% lower, in a further embodiment of at least 60% lower, in a further embodiment of at least 70% lower, in a further embodiment of at least 80% lower, in a further embodiment of at least 90% lower, in a further embodiment of 100% lower (complete inhibition).

Preferably, a caspase-1 inhibitor is a compound having a low level of cellular toxicity.

In an embodiment, the caspase-1 inhibitor is for administration in the form of a prodrug, which is converted to its active metabolite.

Various inhibitors of caspase-1 are known (see for example U.S. Pat. Nos. 9,352,010 and 7,417,029) and are commercially available for research but none are currently used clinically.

For examples, Caspase-1 inhibitors include Pralnacasan (VX-740), IDN-6556 and VX-765.

Peptide-based Caspase-1 inhibitors include Ac-YVAD-cmk (Ac-Tyr-Val-Ala-Asp-chloromethylketone), Ac-WEHD-CHO (N-Acetyl-Trp-Glu-His-Asp-al), and Z-VAD-FMK (Z-Val-Ala-Asp fluoromethyl ketone).

In an embodiment, the caspase-1 inhibitor is a compound having Formula I:

wherein $R^1$ is

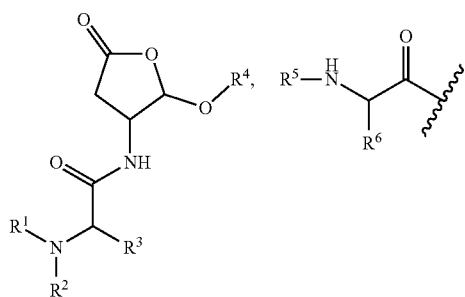

I $R^2$ and $R^3$ taken together form a ring, wherein said ring is:

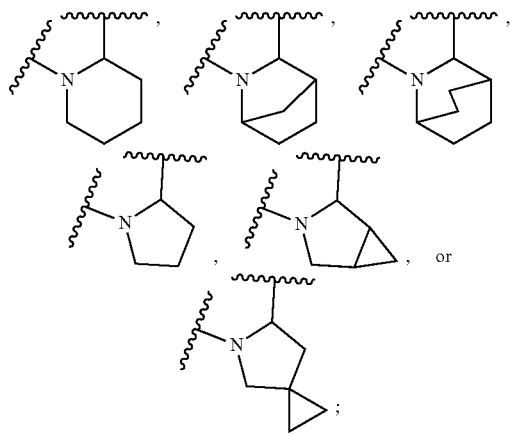

wherein, in each ring, any hydrogen atom is optionally and independently replaced by $R^7$ and any set of two hydrogen atoms bound to the same atom is optionally and independently replaced by carbonyl;

when the ring formed by $R^2$ and $R^3$ is

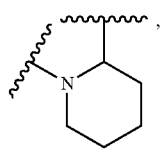

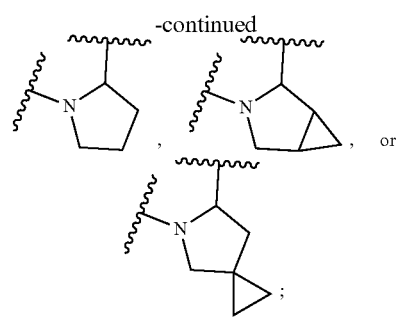

then
$R^5$ is $R^8C(O)$—, and
$R^8$ is phenyl, thiophene, or pyridine, wherein each ring is optionally substituted with up to 5 groups independently selected from $R^9$, and wherein at least one position on the phenyl, thiophene, or pyridine is substituted by $R^{10}$;

when the ring formed by $R^2$ and $R^3$ is

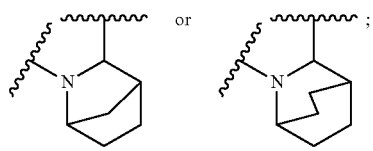 [SMILES: *C1C2CCC(C2)N1* ; *C1C2CCC(CC2)N1*]

then
$R^5$ is $R^8C(O)$—, HC(O), $R^8SO_2$—, $R^8OC(O)$, $(R^8)_2NC(O)$, $(R^8)(H)NC(O)$, $R^8C(O)C(O)$—, $R^8$—, $(R^8)_2NC(O)C(O)$, $(R^8)(H)NC(O)C(O)$, or $R^8OC(O)C(O)$—; and $R^8$ is $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic)-$(C_{1-12}$aliphatic)-, $(C_{6-10}$aryl)-$(C_{1-12}$aliphatic)-, (5-10 membered heterocyclyl)-$(C_{1-12}$aliphatic)-, or (5-10 membered heteroaryl)-$(C_{1-12}$aliphatic)-; or two $R^8$ groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, $NR^{11}$, S, SO, and $SO_2$, wherein $R^8$ is substituted with up to 6 substituents independently selected from $R^{12}$;

$R^4$ is H, $C_{1-12}$aliphatic, $C_{3-10}$cycloaliphatic, $C_{6-10}$aryl, 5-10 membered heterocyclyl, 5-10 membered heteroaryl, $(C_{3-10}$cycloalkyl)-$(C_{1-12}$aliphatic)-, cycloalkenyl-$(C_{1-12}$aliphatic)-, $(C_{6-10}$aryl)-$(C_{1-12}$aliphatic)-, (5-10 membered heterocyclyl)-$(C_{1-12}$aliphatic)-, or (5-10 membered heteroaryl)-$(C_{1-12}$aliphatic)-, wherein any hydrogen atom is optionally and independently replaced by $R^{12}$ and any set of two hydrogen atoms bound to the same atom is optionally and independently replaced by carbonyl;

$R^6$ is —$C(R^{13})(R^{14})(R^{15})$, $C_{6-10}$aryl, 5-10 membered heteroaryl, or $C_{3-7}$cycloalkyl;

$R^7$ is halogen, —$OR^{11}$, —$NO_2$—CN—$CF_3$, —$OCF_1$, —$R^{11}$, 1,2-methylenedioxy, 1,2-ethylenedioxy, —$N(R^{11})_2$, —$SR^{11}$, —$SOR^{11}$, —$SO_2R^{11}$—$SO_2N(R^{11})_2$, —$SO_3R^{11}$, —$C(O)R^{11}$, —$C(O)C(O)R^{11}$, —$C(O)C(O)OR^{11}$, —$C(O)C(O)N(R^{11})_2$, —$C(O)CH_2C(O)R^{11}$, —$C(S)R^{11}$, —$C(S)OR^{11}$, —$C(O)OR^{11}$, —$OC(O)R^{11}$, —$C(O)N(R^{11})_2$, —$OC(O)N(R^{11})_2$, —$C(S)N(R^{11})_2$, —$(CH_2)_{0-2}NHC(O)R^{11}$, —$N(R^{11})N(R^{11})COR^{11}$, —$N(R^{11})N(R^{11})C(O)OR^{11}$, —$N(R^{11})N(R^{11})CON(R^{11})_2$, —$N(R^{11})SO_2R^{11}$, —$N(R^{11})SO_2N(R^{11})_2$, —N(R$^{11}$)C(O)OR$^{11}$, —N(R$^{11}$)C(O)R$^{11}$, —N(R$^{11}$)C(S)R$^{11}$, —N(R$^{11}$)C(O)N(R$^{11}$)$_2$, —N(R$^{11}$)C(S)N(R$^{11}$)$_2$—N(COR$^{11}$) COR$^{11}$, —N(OR$^{11}$)R$^{11}$, —C(=NH)N(R$^{11}$)$_2$, —C(O)N (OR$^{11}$)R$^{11}$, —C(=NOR$^{11}$)R$^{11}$, —OP(O)(OR$^{11}$)$_2$, —P(O) (R$^{11}$)$_2$, —P(O)(OR$^{11}$)$_2$, or —P(O)(H)(OR$^{11}$);

R$^9$ and R$^{12}$ are each independently halogen, —OR$^{11}$, —NO$_2$, —CN, —CF$_3$, —OCF$_3$, —R$^{11}$, 1,2-methylenedioxy, 1,2-ethylenedioxy, —N(R$^{11}$)$_2$, —SR$^{11}$, —SOR$^{11}$, —SO$_2$R$^{11}$, —SO$_2$N(R$^{11}$)$_2$—SO$_3$R$^{11}$, —C(O)R$^{11}$, —C(O)C (O)R$^{11}$, —C(O)C(O)OR$^1$, —C(O)C(O)N(R$^{11}$)$_2$, —C(O) CH$_2$C(O)R$^{11}$, —C(S)R$^{11}$, —C(S)OR$^{11}$, —C(O)OR$^{11}$, —OC (O)R$^{11}$, —C(O)N(R$^{11}$)$_2$, —OC(O)N(R$^{11}$)$_2$, —C(S)N(R$^{11}$)$_2$, —(CH$_2$)$_{0-2}$NHC(O)R$^{11}$, —N(R$^{11}$)N(R$^{11}$)COR$^{11}$, —N(R$^{11}$)N(R$^{11}$)C(O)OR$^{11}$, —N(R$^{11}$)N(R$^{11}$)CON(R$^{11}$)$_2$, —N(R$^{11}$)SO$_2$R$^{11}$, —N(R$^{11}$)SO$_2$N(R$^{11}$)$_2$, —N(R$^{11}$)C(O)OR$^{11}$, —N(R$^{11}$)C(O)R$^{11}$, —N(R$^{11}$)C(S)R$^{11}$, —N(R$^{11}$)C(O) N(R$^{11}$)$_2$, —N(R$^{11}$)C(S)N(R$^{11}$)$_2$, —N(COR$^{11}$)COR$^{11}$, —N(OR$^{11}$)R$^{11}$, —C(=NH)N(R$^{11}$)$_2$, —C(O)N(OR$^{11}$)R$^{11}$, —C(=NOR$^{11}$)R$^{11}$, —OP(O)(OR$^{11}$)$_2$, —P(O)(R$^{11}$)$_2$, —P(O)(OR$^{11}$)$_2$, or —P(O)(H)(OR$^{11}$);

R$^{10}$ is halogen, —OR$^{17}$, —NO$_2$—CN—CF$_3$—OCF$_3$, —R$^{17}$, or —SR$^{11}$, wherein R$^{10}$ has no more than 5 straight-chained atoms;

R$^{11}$ is hydrogen, C$_{1-12}$aliphatic, C$_{3-10}$cycloaliphatic, C$_{6-10}$aryl, 5-10 membered heterocyclyl, 5-10 membered heteroaryl, (C$_{3-10}$cycloaliphatic)-(C$_{1-12}$aliphatic)-, (C$_{1-10}$aryl)-(C$_{1-12}$aliphatic)-, (5-10 membered heterocyclyl)-(C$_{1-12}$aliphatic)-, or heteroaryl-(C$_{1-12}$aliphatic)-; wherein any hydrogen atom is optionally and independently replaced by R$^{18}$ and any set of two hydrogen atoms bound to the same atom is optionally and independently replaced by carbonyl;

R$^{13}$ is H or a C$_{1-6}$ straight-chained or branched alkyl;

R$^{14}$ is H or a C$_{1-6}$ straight-chained or branched alkyl;

R$^{15}$ is —CF$_3$, —C$_{3-7}$cycloalkyl, C$_{6-10}$aryl, 5-10 membered heteroaryl, heterocycle, or a C$_{1-6}$ straight-chained or branched alkyl, wherein each carbon atom of the alkyl is optionally and independently substituted with R$^{16}$;

or R$^{13}$ and R$^{15}$ taken together with the carbon atom to which they are attached form a 3-10 membered cycloaliphatic;

R$^{16}$ is halogen, —OR$^{17}$, —NO$_2$, —CN, —CF$_3$—OCF$_3$, —R$^{17}$, or —SR$^{17}$; wherein R$^{17}$ is C$_{1-4}$-aliphatic-;

R$^{17}$ is C$_{1-4}$-aliphatic-; and

R$^{18}$ is —OR$^{17}$, —NO$_2$, —CN, —CF$_3$, —OCF$_3$, —R$^{17}$, 1,2-methylenedioxy, 1,2-ethylenedioxy, —N(R$^{17}$)$_2$, —SR$^{17}$, —SOR$^{17}$, —SO$_7$R$^{17}$—SO$_2$N(R$^{17}$)$_2$—SO$_3$R$^{17}$, —C(O)R$^{17}$, —C(O)C(O)R$^{17}$, —C(O)C(O)OR$^{17}$, —C(O)C(O)N(R$^{17}$)$_2$, —C(O)CH$_2$C(O)R$^{17}$—C(S)R$^{17}$, —C(S)OR$^{17}$, —C(O) OR$^{17}$, —OC(O)R$^{17}$, —C(O)N(R$^{17}$)$_2$, —OC(O)N(R$^{17}$)$_2$, —C(S)N(R$^{17}$)$_2$, —(CH$_2$)$_{0-2}$NHC(O)R$^{17}$, —N(R$^{17}$)N(R$^{17}$) COR$^{17}$, —N(R$^{17}$)N(R$^{17}$)C(O)OR$^{17}$, —N(R$^{17}$)N(R$^{17}$)CON (R$^{17}$)$_2$, —N(R$^{17}$)SO$_2$R$^{17}$, —N(R$^{17}$)SO$_2$N(R$^{17}$)$_2$, —N(R$^{17}$) C(O)OR$^{17}$, —N(R$^{17}$)C(O)R$^{17}$, —N(R$^{17}$)C(S)R$^{17}$, —N(R$^{17}$) C(O)N(R$^{17}$)$_2$, —N(R$^{17}$)C(S)N(R$^{17}$)$_2$, —N(COR$^{17}$)COR$^{17}$, —N(OR$^{17}$)R$^{17}$, —C(=NH)N(R$^{17}$)$_2$, —C(O)N(OR$^{17}$)R$^{17}$, —C(=NOR$^{17}$)R$^{17}$, —OP(O)(OR$^{17}$)$_2$, —P(O)(R$^{17}$)$_2$, —P(O)(OR$^{17}$)$_2$, or —P(O)(H)(OR$^{17}$); R$^{17}$ is hydrogen, C$_{1-12}$aliphatic, C$_{3-10}$cycloaliphatic, C$_{6-10}$aryl, 5-10 membered heterocyclyl, 5-10 membered heteroaryl, (C$_{3-10}$cycloaliphatic)-(C$_{1-12}$aliphatic), (C$_{6-10}$aryl)-(C$_{1-12}$aliphatic)-, (5-10 membered heterocyclyl)-(C$_{1-12}$aliphatic)-, or heteroaryl-(C$_{1-12}$aliphatic)-;

or single stereoisomers, mixtures of stereoisomers, or pharmaceutically acceptable salts thereof.

In an embodiment, the caspase-1 inhibitor is a compound of Formula II:

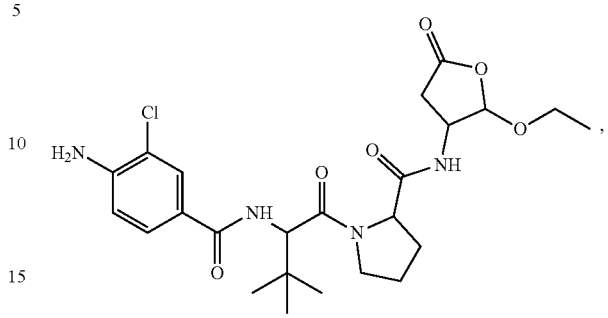

II or single stereoisomers, mixtures of stereoisomers, or pharmaceutically acceptable salts thereof.

In an embodiment, the caspase-1 inhibitor is VX-765 or a pharmaceutically acceptable salt thereof. VX-765 (see for example Reference 1 and WO 2011/094426), or (S)-1-((S)-2-{[1-(4-amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide, has the following structure:

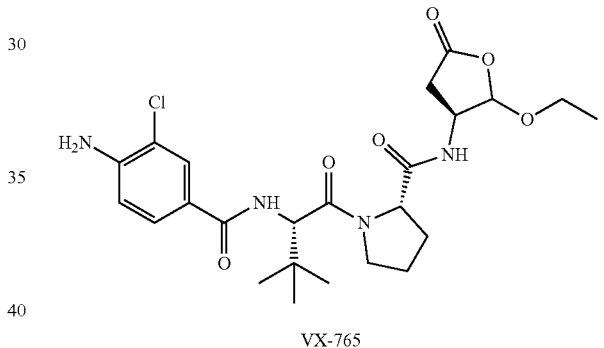

VX-765

VX-765 is a prodrug which is converted to its active metabolite VRT-043198 via esterase cleavage of the 5-ethoxydihydrofuran-2(3H)-one moiety. There are two tautomers of VRT-043198, the ring-closed form and the ring-open form, which interconvert.

The ring-closed form of VRT-043198, or (2S)-1-((S)-2-(4-amino-3-chlorobenzamido)-3,3-dimethylbutanoyl)-N-((3S)-2-hydroxy-5-oxotetrahydrofuran-3-yl)pyrrolidine-2-carboxamide, has the following structure:

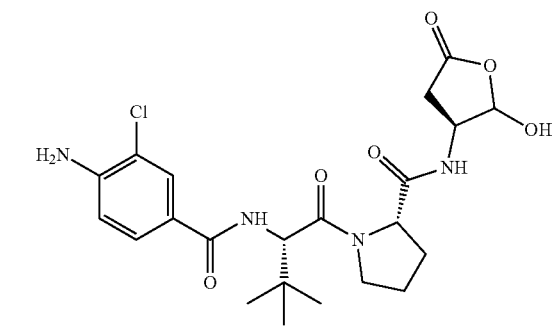

The ring-open form of VRT-043198, or (S)-3-((S)-1-((S)-2-(4-amino-3-chlorobenzamido)-3,3-dimethylbutanoyl)pyrrolidine-2-carboxamido)-4-oxobutanoic acid, has the following structure:

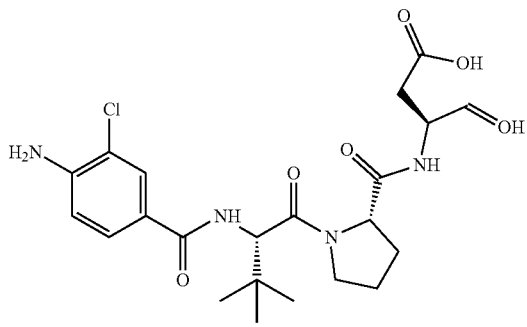 [SMILES: CC(C)(C)[C@H](NC(=O)c1ccc(N)c(Cl)c1)C(=O)N1CCC[C@H]1C(=O)N[C@H](C=O)CC(=O)O]

As used herein, "alkyl" or the prefix "alk" refers to an optionally substituted straight or branched chain saturated hydrocarbon group. Examples of straight or branched chain alkyl groups include, but are not limited to, methyl, trifluoromethyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3, 3-dimethyl-1-butyl, 2-ethyl-1-butyl, 1-heptyl, and 1-octyl. A substituted alkyl can be substituted with one or more (e.g., 2, 3, 4, 5, 6, or 7) substituent groups such as -halogen, —NH$_2$, —NH(C$_1$-C$_{12}$ alkyl), —N(C$_1$-C$_{12}$ alkyl)$_2$, —OH, —O—(C$_1$-C$_{12}$ alkyl), or C$_6$-C$_{10}$ aryl groups, such as phenyl or naphthyl groups, or any other substituent group described herein. In an embodiment, the alkyl group contains 1-12 carbons, in further embodiments 1-8, 1-6 or 1-3 carbons.

As used herein, "aryl" refers to an optionally substituted monocyclic or polycyclic structure wherein all rings are aromatic, either fused together (e.g. naphthalene) or linked together (e.g. biphenyl) and formed by carbon atoms. Exemplary aryl groups include phenyl, naphthyl, and biphenyl. Where an aryl group is substituted, substituents can include any substituent groups described herein. In an embodiment, the aryl comprises from 6 to 15 carbons (C$_6$-C$_{15}$ aryl), in a further embodiment, 6 to 10 carbons (C$_6$-C$_{10}$ aryl).

As used herein, "heteroaryl" or "heteroaromatic" refers to an aryl where one or more carbon atom has been replaced by an heteroatom, such as N, O, or S. In an embodiment, the heteroaryl is 5-10 membered.

As used herein, "cycloalkyl" refers to an optionally substituted, aliphatic, saturated or unsaturated monocyclic or polycyclic (e.g., bicyclic or tricyclic) hydrocarbon ring system.

Polycyclic cycloalkyls may be linear, fused, bridged, or spirocyclic. In an embodiment, the cycloalkyl contains 3-12 carbon atoms (C$_3$-C$_{12}$ cycloalkyl), in a further embodiment, 3-10 carbon atoms (C$_3$-C$_{10}$ cycloalkyl), in a further embodiment, 3-7 carbon atoms (C$_3$-C$_7$ cycloalkyl).

As used herein, "alkenyl" refers to an optionally substituted unsaturated, straight or branched chain hydrocarbon group containing at least one carbon-carbon double bond. In an embodiment, the alkenyl comprises from 2 to 8 carbon atoms "C$_2$-C$_8$ alkenyl", in a further embodiment from 2 to 6 or 2 to 4 carbon atoms.

As used herein, "alkynyl" refers to an optionally substituted unsaturated, straight or branched chain hydrocarbon group containing at least one carbon-carbon triple bond. In an embodiment, the alkynyl comprises from 2 to 8 carbon atoms "C$_2$-C$_8$ alkynyl", in a further embodiment from 2 to 6, or 2 to 4 carbon atoms.

As used herein, "halogen" refers to —F, —Cl, —Br, or —I.

As used herein, a "heterocycle" or "heterocyclyl" is an optionally substituted aromatic or aliphatic monocyclic or bicyclic ring system that includes one or more carbon atoms and heteroatoms (e.g., 1, 2, 3, or 4 heteroatoms), such as oxygen, nitrogen, and sulfur. Aliphatic heterocycles may have one or more double bonds. Examples of double bonds include carbon-carbon double bonds (C=C), carbon-nitrogen double bonds (C=N), and nitrogen-nitrogen double bonds (N=N). Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, diazinanyl, piperidinyl, tetrahydropyridinyl, piperazinyl, morpholinyl, azepinyl or any partially or fully saturated derivatives thereof, diazepinyl or any partially or fully saturated derivatives thereof, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl, and indazolyl. Where an heterocycle is substituted, substituents can include any substituent group described herein. In embodiments, the heterocycle is a 3- to 10-membered, 5- to 10-membered or 3- to 9-membered heterocycle.

As used herein, "aromatic" refers to a cyclic ring system having (4n +2) π electrons in conjugation, where n is 1, 2, or 3.

Any group described herein may be substituted or unsubstituted. When substituted, they may be with any desired substituent or substituents that do not adversely affect the desired activity of the compound. Examples of preferred substituents are those found in the exemplary compounds and embodiments disclosed herein, as well as substituents such as: halogen (chloro, iodo, bromo, or fluoro); C$_{1-12}$ alkyl; C$_{1-6}$ alkyl; C$_{2-6}$ alkenyl; C$_{2-6}$ alkynyl; hydroxyl; C$_{1-6}$ alkoxyl; amino (primary, secondary, or tertiary); nitro; thiol; thioether; imine; cyano; amido; carbamoyl; phosphonato; phosphine; a phosphorus (V) containing group; carboxyl; thiocarbonyl; sulfonyl; sulfonamide; ketone; aldehyde; ester; oxo; haloalkyl (e.g., trifluoromethyl); cycloalkyl, which may be monocyclic or fused or non-fused polycyclic (e.g., cyclopropyl, cyclobutyl, cyclopentyl, or cyclohexyl), or aliphatic heterocyclic, which may be monocyclic or fused or non-fused polycyclic (e.g., pyrrolidinyl, piperidinyl, piperazinyl, morpholinyl, or thiazinyl); and aromatic carbocyclic or heterocyclic, monocyclic or fused or non-fused polycyclic (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl). Specific substituent groups include benzyloxy; —N(CH$_3$)$_2$; O-alkyl (O—CH$_3$); O-aryl; aryl; aryl-lower alkyl; —CO$_2$CH$_3$; —OCH$_2$CH$_3$; methoxy; —CONH$_2$; —OCH$_2$CONH$_2$; —SO$_2$NH$_2$; —OCHF$_2$; —CF$_3$; and —OCF$_3$. A substituted group may have 1, 2, 3, 4, 5, 6, 7, or 8 substituent groups. These substituent groups may optionally be further substituted with a substituent listed herein. Substituents may also be optionally substituted by a fused-ring structure or bridge, for example —OCH$_2$O—. In other embodiments, these substituents are not further substituted.

In an embodiment, the neurodegenerative disease is Alzheimer's Disease. Alzheimer's Disease (AD) is a neurological disease thought to be caused by an accumulation of abnormal deposit of proteins in the brain, known as amyloid (Aβ) plaques, which are composed primarily of Aβ fibrils. An increase in the production and accumulation of beta-amyloid peptide in plaques leads to nerve cell death, which contributes to the development and progression of AD. The proteins principally responsible for the creation of plaques include amyloid precursor protein (APP), beta and Gamma-secretases. The presenilin I is part of the gamma secretase complex. Sequential cleavage of APP by the enzymes β and γ secretase leads to the release of a 38 to 42 (e.g., 38, 40 or 42) amino acid Aβ peptide, which has a propensity of aggregating in plaques. The Aβ$_{42}$ peptide in particular has a high propensity of such aggregation, and is therefore believed to be central to the initiation of plaque formation in AD.

Other pathologies that define AD include neurofibrillary tangles (intraneuronal—made of hyperphosphorylated Tau protein), neuropil threads (degenerating neurites also containing hyperphosphorylated Tau), and synaptic degeneration or loss. Recently, atrophy of the hippocampus and cortex was added as an early event in AD pathology and is identified by MRI.

In an embodiment, the cognitive impairment is mild cognitive impairment. In a further embodiment, the cognitive impairment is subjective cognitive impairment. In a further embodiment, the cognitive impairment is age-dependent cognitive impairment. In a further embodiment, the cognitive impairment comprises a memory deficit. In a further embodiment, the subject has a neuropsychological profile indicative of age-dependent cognitive impairment. In a further embodiment, the subject suffers from neuroinflammation in the brain associated with cognitive impairment.

The present invention also relates to a kit comprising a caspase-1 inhibitor, or a composition comprising the caspase-1 inhibitor and a pharmaceutically acceptable carrier, for use in preventing, delaying the onset or reducing the severity of, preventing or reversing the progression of, or treating a neurological condition (e.g., a neurodegenerative disease (e.g., AD)) in a subject. The present invention also relates to a kit comprising a caspase-1 inhibitor, or a composition comprising the caspase-1 inhibitor and a pharmaceutically acceptable carrier, for use in preventing, delaying the onset or reducing the severity of, preventing or reversing the progression of, or treating cognitive impairment in a subject. The arrangement and construction of such kits is conventionally known to one of skill in the art. Such kits may include, for example, container(s) (e.g., a syringe and/or vial and/or ampoule) for containing the agent or combination of agents or compositions, other apparatus for administering the therapeutic agent(s) and/or composition(s) and/or diluent(s). The kit may optionally further include instructions. The instructions may describe how the agent(s) and the diluent should be mixed to form a pharmaceutical formulation. The instructions may also describe how to administer the resulting pharmaceutical formulation to a subject. In an embodiment, the above-mentioned kit comprises instructions for preventing, delaying the onset or reducing the severity of, preventing or reversing the progression of, or treating a neurological condition (e.g., a neurodegenerative disease (e.g., AD)), or for preventing, delaying the onset or reducing the severity of, preventing or reversing the progression of, or treating cognitive impairment, in a subject.

"Progression" as used herein refers to an advancement or worsening of a disease or condition (e.g. neurological condition (e.g., a neurodegenerative disease (e.g., AD), cognitive impairment, etc.) over time.

In an embodiment, the subject is pre-symptomatic for the neurological condition (e.g., a neurodegenerative disease (e.g. AD)). "Pre-symptomatic" as used herein refers to a subject that is suffering from a noticeable and measurable decline in neural function (e.g., cognitive abilities such as memory), but does not show the more pronounced or severe symptoms characteristic of the neurological condition (e.g., a neurodegenerative disease (e.g., AD)). For example, such subjects exhibit poorer cognitive abilities than would be normally expected for their age, but do not otherwise show clear symptoms definitive of a diagnosis of the neurological condition (e.g., a neurodegenerative disease (e.g., AD)). Lower cognitive performance includes but is not limited to episodic memory, semantic memory, spatial memory, and working memory. In the case of AD, pre-symptomatic or asymptomatic also define the presence of AD pathologies in the brain in the absence of noticeable cognitive impairments. This can occur in both the sporadic and the familial forms of AD. In embodiments, the subject has (a) increased amyloid and tau pathology in the brain; (b) atrophied hippocampus, and/or (c) amyloid, Tau and/or inflammatory biomarker profiles indicative of progression to the neurological condition (e.g., a neurodegenerative disease (e.g., AD)). Amyloid can be detected for example by PET imaging or by lower levels in the CSF, Tau may be detected by PET or increased levels of phosphorylated Tau compared to total Tau in CSF, increased total Tau in CSF is also associated with disease [see Jack C R Jr., et al., An unbiased descriptive classification scheme for Alzheimer disease biomarkers. Neurology 87(5): 539-47 (2016)]. Atrophy can be recognized by magnetic resonance imaging. Abnormal levels of cytokine, chemokine, or complement factors in CSF or peripheral blood mononuclear cells are also considered biomarkers; Milan Fiala and Robert Veerhuis, Biomarkers of inflammation and amyloid-β phagocytosis in patients at risk of Alzheimer disease, *Experimental Gerontology* 45(1): 57-63 (2010).

Mild cognitive impairment (MCI) is a general term most commonly defined as a slight but noticeable and measurable decline in cognitive abilities, such as memory and thinking skills. A person with MCI experiences such a decline in cognitive abilities greater than normally expected with aging (i.e., worse than normal for their age), but does not show other, more severe symptoms of neurological conditions such as AD, such as dementia. MCI is considered as an increased risk factor for AD.

Subjective cognitive impairment is a general term most commonly defined as a slight but noticeable decline in cognitive abilities, such as memory and thinking skills, which is not a sufficient decline for a diagnosis of MCI. A person with subjective cognitive impairment notices a difference in their cognitive abilities, but is otherwise able to function normally in daily activities.

Age-dependent cognitive impairment is a decline in cognitive abilities that advances with aging.

In addition to memory deficit/loss, other symptoms of cognitive impairment include the inability to recognize faces or places, repetitive questioning, trouble with learning, trouble with exercising judgment, change in mood or behaviour, vision problems, difficulty in carrying out daily living tasks (e.g., paying bills, following a recipe, grocery shopping).

In an embodiment, the subject has a genetic mutation associated with familial AD, such as early-onset familial Alzheimer's disease (EOFAD). Three genes have been associated with a predisposition to EOFAD: presenilin 1 (PS1), presenilin 2 (PS2), and the amyloid precursor protein gene (APP). All of these genes affect the processing of the amyloid precursor protein and increase the generation of toxic beta-amyloid ($A\beta_{42}$), which creates the plaques in AD. All three of these genes are inherited as autosomal dominant genes.

The invention further provides a (pharmaceutical) composition comprising a caspase-1 inhibitor. Such a composition may be used in the methods and uses described herein, e.g. for preventing, delaying the onset or reducing the severity of, preventing or reversing the progression of, or treating a neurodegenerative disease, or for preventing, delaying the onset or reducing the severity of, preventing or reversing the progression of, or treating cognitive impairment.

In addition to the active ingredients (e.g., a caspase-1 inhibitor, such as a compound having Formula I or II, or a single stereoisomer, mixture of stereoisomers, or a pharmaceutically acceptable salt thereof, for example VX-765, or a pharmaceutically acceptable salt thereof), pharmaceutical compositions may contain suitable pharmaceutically-acceptable carriers or excipients. As used herein "pharmaceutically acceptable carrier" or "excipient" includes any and all solvents, dispersion media, coatings, antibacterial and antifungal agents, isotonic and absorption delaying agents, and the like that are physiologically compatible, and which can be used pharmaceutically. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders (see Remington: The Science and Practice of Pharmacy by Alfonso R. Gennaro, 2003, $21^{th}$ edition, Mack Publishing Company). In embodiments, the carrier may be suitable for intra-neural, parenteral, intravenous, intraperitoneal, intramuscular, subcutaneous, sublingual or oral administration.

Some examples of suitable excipients include lactose, dextrose, sucrose, sorbitol, mannitol, starches, lecithin, phosphatidylcholine, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick sustained or delayed release of the active ingredient after administration to the patient by employing procedures known in the art.

Pharmaceutical compositions suitable for use in the invention include compositions wherein the active ingredients are contained in an effective amount to achieve the intended purpose (e.g., preventing and/or ameliorating and/or inhibiting a disease). The determination of an effective dose is well within the capability of those skilled in the art. For any compounds, the therapeutically effective dose can be estimated initially either in cell culture assays (e.g., cell lines) or in animal models, usually mice, rabbits, dogs or pigs. The animal model may also be used to determine the appropriate concentration range and route of administration. Such information can then be used to determine useful doses and routes for administration in humans. An effective dose or amount refers to that amount of one or more active ingredient(s), for example a caspase-1 inhibitor, which is sufficient for treating a specific disease or condition (e.g., a neurodegenerative disease (e.g., AD)). Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Guidance as to particular dosages and methods of delivery is provided in the literature and generally available to practitioners in the art. In embodiments, dosages of an active ingredient (e.g., a caspase-1 inhibitor, such as a compound having Formula I or II, or a single stereoisomer, mixture of stereoisomers, or a pharmaceutically acceptable salt thereof, for example VX-765, or a pharmaceutically acceptable salt thereof) of between about 0.01 and about 100 mg/kg body weight (in an embodiment, per day) may be used. In further embodiments, dosages of between about 0.5 and about 75 mg/kg body weight may be used. In further embodiments, dosages of between about 1 and about 50 mg/kg body weight may be used. In further embodiments, dosages of between about 10 and about 50 mg/kg body weight in further embodiments about 10, about 25 or about 50 mg/kg body weight, may be used.

In an embodiment, an active ingredient (e.g., a caspase-1 inhibitor, such as a compound having Formula I or II, or a single stereoisomer, mixture of stereoisomers, or a pharmaceutically acceptable salt thereof, for example VX-765, or a pharmaceutically acceptable salt thereof) described herein is administered or is for administration such that it comes into contact with a CNS tissue or a CNS neuron. As used herein, the "central nervous system" or CNS is the portion of the nervous system comprising the brain and the spinal cord. By contrast, the "peripheral nervous system" or PNS is the portion of the nervous system other than the brain and the spinal cord. In an embodiment, the CNS tissue is the cerebral cortex, in a further embodiment, the hippocampus. As such, in embodiments an active ingredient (e.g., a caspase-1 inhibitor, such as a compound having Formula I or II, or a single stereoisomer, mixture of stereoisomers, or a pharmaceutically acceptable salt thereof, for example VX-765, or a pharmaceutically acceptable salt thereof) described herein can be administered to treat CNS cells in vivo via direct intracranial or intrathecal injection or injection into the cerebrospinal fluid. Alternatively, an active ingredient (e.g., a caspase-1 inhibitor, such as a compound having Formula I or II, or a single stereoisomer, mixture of stereoisomers, or a pharmaceutically acceptable salt thereof, for example VX-765, or a pharmaceutically acceptable salt thereof) described herein can be administered systemically (e.g. intravenously, intraperitoneally, or orally) in a form (or converted in vivo to a form) capable of crossing the blood brain barrier and entering the CNS.

A "therapeutically effective amount" refers to an amount effective, at dosages and for periods of time necessary, to achieve the desired therapeutic result. A "prophylactically effective amount" refers to an amount effective, at dosages and for periods of time necessary, to achieve the desired prophylactic result, such as preventing or inhibiting the rate of onset or progression of the above-noted conditions. A prophylactically effective amount can be determined as described above for the therapeutically effective amount.

As used herein, the terms "subject" or "patient" are used interchangeably and are used to mean any animal, such as a mammal, including humans and non-human primates. In an embodiment, the above-mentioned subject is a mammal. In a further embodiment, the above-mentioned subject is a human.

MODE(S) FOR CARRYING OUT THE INVENTION

The present invention is illustrated in further details by the following non-limiting examples.

Example 1: Study Drug

The compound used in the studies described herein is (S)-1-((S)-2-{[1-(4-amino-3-chloro-phenyl)-methanoyl]-amino}-3,3-dimethyl-butanoyl)-pyrrolidine-2-carboxylic acid ((2R,3S)-2-ethoxy-5-oxo-tetrahydro-furan-3-yl)-amide, also referred to as VX-765. VX-765 has the following structure:

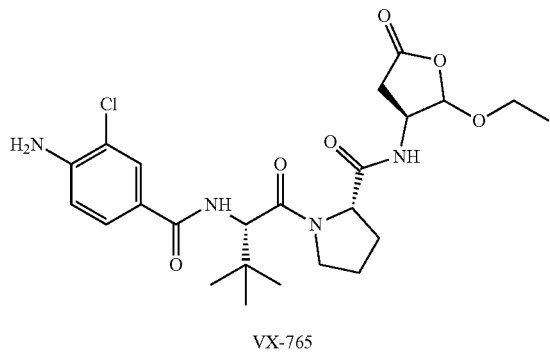

VX-765

Example 2: Materials and Methods

Experimental Design: Treatment of Symptomatic Mice of 5 Months of Age.

Studies were started on 20 (full onset of symptoms) week old J20 and littermate WT controls injected with 50 mg/Kg VX-765 or vehicle. The 20-week-old mice were treated per the paradigm in section. VX-765 reverses episodic memory deficits in the J20 mouse.

Experimental Design: Prevention of Pre-Symptomatic Mice of 2 Months of Age.

Studies are done on 8 (pre-symptomatic) week old J20 and littermate WT controls injected with 50 mg/Kg VX-765 or vehicle. The 8 week old mice are injected for 4 weeks (3 injections per week) and monitored for memory deficits at 16 weeks of age and every 4 weeks thereafter until the mice reach 8 months of age. VX-765 delays the onset of cognitive deficits by at least 5 months in the J20 mouse.

Effect of VX-765 on Mouse Behaviour.

Anxiety and hyperactivity are monitored in an open-field paradigm, episodic memory with the NOR, spatial memory with the Barnes maze, and short or long term working memory with the Y maze before and after treatments. Repeated measures are acceptable for the NOR, Barnes and Y maze[2-4].

To assess AD-like pathology, immunohistochemical analyses were performed to detect amyloid deposition (anti-AβF25276)[5,6], microglial (Iba1) activation[7], astrogliosis (GFAP), synaptophysin protein levels on coronal brain sections. Multiplex MSD ELISA was used to assess Aβ levels and 38,40, and 42 subtypes, and II-1β brain levels. RT-PCR was used to assess levels of human APP$^{Sw/Ind}$.

Example 3: VX-765 Reverses Episodic Memory Deficits in the J20 Mouse

J20 and littermate WT mice (20 wks) were first tested for episodic memory deficits with Novel Object Recognition (NOR) and anxiety and hyperactivity in an open-field paradigm. Before treatments (pre-treatment), the WT mice (n=6) performed normally while the J20 (n=8) showed a deficit in the NOR test, as expected (FIG. 1: Pre-treatment). Mice were submitted to three injections with the pre-determined dose of 50 mg/Kg (0.01 µl/g mice) VX-765 in 25% Cremophore prepared in water[1], or vehicle only, every 48 hours and re-tested 48 hrs after the last injection. Vehicle-injected WT mice retained normal NOR behavior while vehicle-injected J20 remained impaired and VX-765-injected J20 mice reverted to normal. The injections were continued for 2 weeks at 3 injections/week (48 hr intervals between injections and 3 day interval between weeks) and mice retested. WT and VX-765-injected J20 mice continued to perform normally while the vehicle-injected J20 retained the NOR deficit. We then removed the drug for a 4-week washout period and the NOR deficits reappeared in the previously VX-765-injected J20 mice, and remained abnormal in vehicle-injected J20 mice. We then re-injected the mice with 3 injections every 48 hours and the VX-765-injections attenuated NOR deficits while vehicle-injected J20 mice retained NOR deficits. J20 mice show hyperactivity in the open-field paradigm, which was attenuated only after 3 weeks of treatment. None of the mice showed anxiety by thigmotaxis (not shown).

Figure 2:
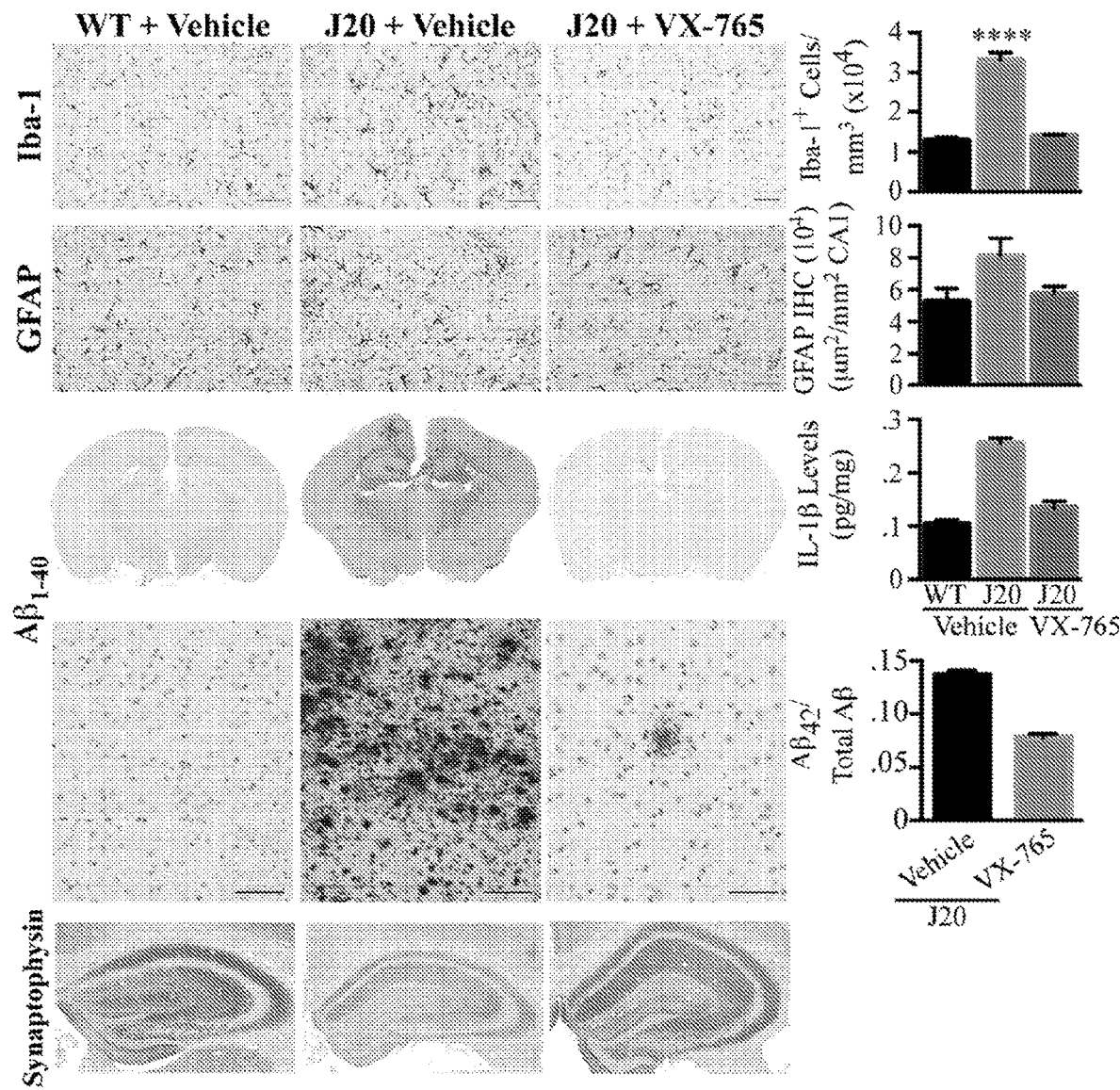
FIG. 2: Immunohistochemistry with microglial Iba1, astroglial GFAP, synaptophysin, and anti-A$\beta_{40}$ antibodies (n=8 WT, n=4 J20+VX-765, n=5 J20+Veh) in the TREATMENT groups. Iba1 was quantitated using the fractionator/dissector method, GFAP by densitometry because single neurons cannot be counted, and II-1$\beta$ and A$\beta_{38,40,42}$ by MSD ELISA. ANOVA and Dunnett's evaluation shows statistical difference from WT for Iba1. MSD ELISA for Il-1$\beta$ and A $\beta$ (n=1+variance) shown in pg/mL. Synaptophysin level quantitation is in progress.

Example 4: VX-765 Intraperitoneal Injections Prevent Brain Microglial Activation, II-1β Loss of Synaptophysin, and Aβ$_{42}$ Production After the last behavioral analyses, the mice were sacrificed and brains were subjected to histological examinations. Compared to WT mice, brain CA1 from J20 vehicle-injected mice showed increased Iba1-positive microglia, which were normalized in the VX-765-injected J20 mice (FIG. 2). GFAP was increased in vehicle-treated J20 and reduced in VX-765-treated J20 cortex, but the data did not reach statistical significance. Immunohistochemistry with anti-F25276 anti-amyloid (1-40) antibody showed a high level of amyloid deposits in the J20 brains, and none in the WT mice control brains. In the J20+VX-765 treated mice, the brains only retained rare amyloid deposits that are similar to amyloid plaques. ELISA of RIPA-extracted brain proteins confirmed that increased Il-1β and Aβ$_{42}$ levels in J20 cortex was reduced by VX-765. These results show that reversal of cognitive deficits in VX-765-treated J20 mice is associated with reduced Il-1β and Aβ$_{42}$ levels and with increased synaptophysin levels. Therefore, the J20 brains are rapidly renormalized with respect to inflammation, amyloid accumulation, and synaptic dysfunction, after 12 injections of VX-765.

Figure 3:
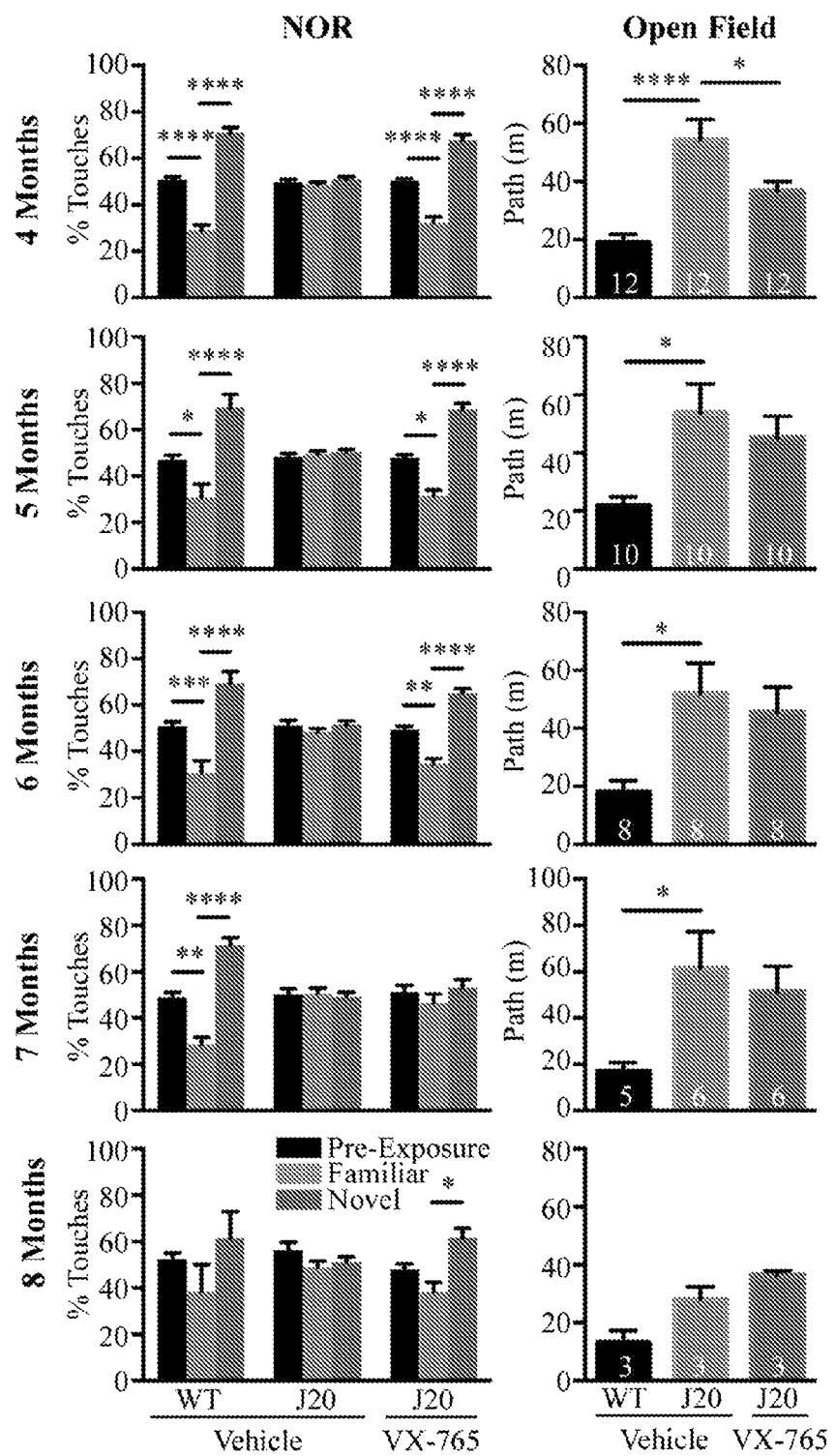
FIG. 3: NOR and open-field from treated pre-symptomatic J20 mice (PREVENTION Groups). NOR: 2-Way ANOVA (Tukey Multiple Comparison, OF: 1-Way ANOVA Dunnett's Multiple Comparison (with J20+Vehicle).

Example 5: Pre-Symptomatic Treatment with VX-765 Delays J20 NOR Deficits and Hyperactivity To determine if VX-765 can delay the appearance of AD-like cognitive deficits and pathology in the J20 mice, J20 mice were injected 3 times per week for 4 weeks starting at 2 months of age. We started NOR tests at 4 months of age, after 1 month without drug, and retested every month thereafter until 8 months of age (FIG. 3). The results show that vehicle-injected WT and VX-765-injected J20 mice perform normally on NOR, whereas vehicle injected J20 show NOR deficits at 4, 5, and 6 months of age (1, 2, and 3 month washout, respectively). At 7 months of age (4 month washout), 3 out of 6 VX-765-injected mice developed NOR deficits and on average, this group showed NOR deficits. At 8 months of age, only 1 of 3 mice have NOR deficit resulting in an averaged normal behavior. Since we sacrificed 2 mice per group at 4, 5, and 6 months and 3 mice per group at 7 and 8 months, note that the results of the older groups need more experimental data for solid conclusions. In the open-field, mice showed normal behavior at 4 months of age but the hyperactivity returned by 5 months of age.

Figure 4:
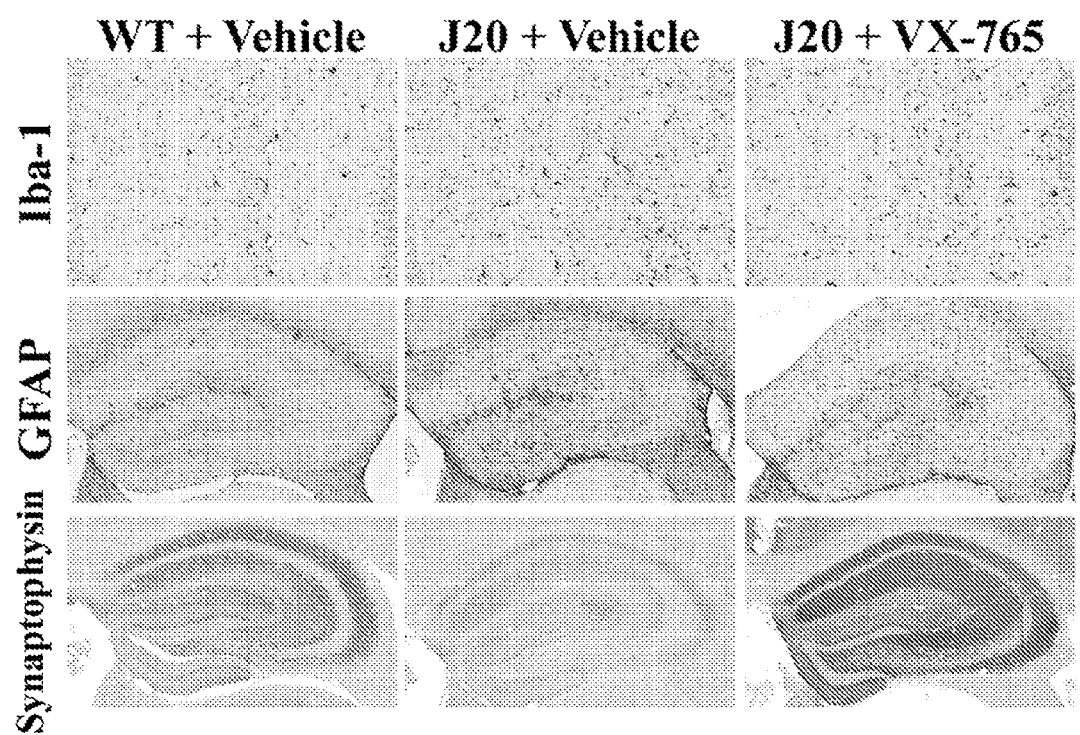
FIG. 4: Immunostainings of mice hippocampus at 4 months of age (PREVENTION GROUP) with microglial Iba-1, astrocyte GFAP, and synaptic synaptophysin antibodies.

Example 6: Pre-Symptomatic Treatment with VX-765 Delays Inflammation and Loss of Synaptophysin in the 4 Month Old J20 Mice Brains Pre-treatment of J20 mice with VX-765 reduced microglial Iba1 positive inflammation and possibly GFAP astrogliosis (FIG. 4). There was an impressive preservation of synaptophysin levels in VX-765-treated J20 mice brains compared to vehicle treatment. The levels of Aβ were undetectable at 4 months of age.

Example 7: APP Protein Levels are Maintained with VX-765 Treatment

Figure 5:
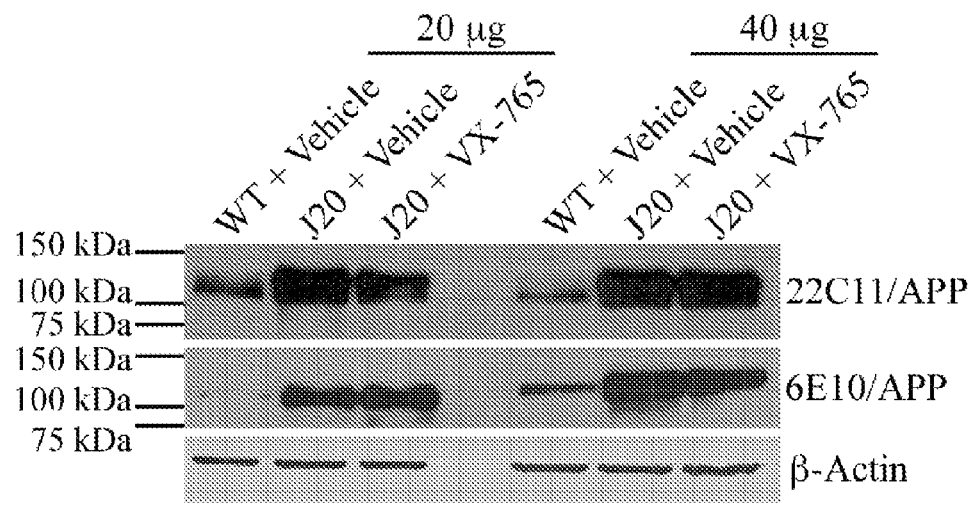
FIG. 5: Western blot against the C-terminus (C11) and A$\beta$ (6E10) regions of APP in TREATMENT mice groups before washout.

Western blots confirmed that the transgenic APP$^{Sw/Ind}$ was still overexpressed in both the vehicle-injected and VX-765-injected J20 mouse pre-frontal cortex, thereby excluding a potential inhibition of APP gene expression with treatments as a reason for decreased amyloid levels in the J20+VX-765 mice (FIG. 5).

Figure 6:
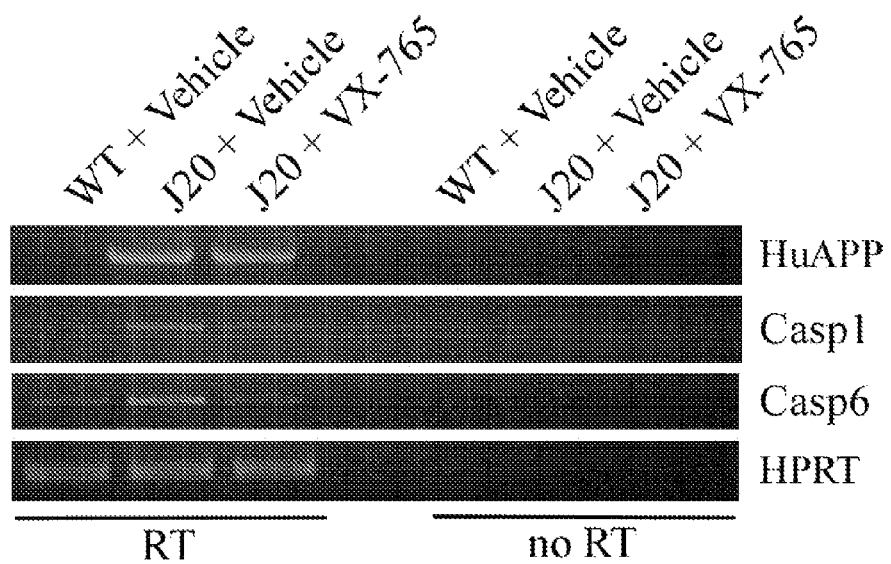
FIG. 6: Agarose stained gel shows amplicons from RT-PCR of APP, Casp6, Casp1 and Hprt1 as control (TREATMENT GROUP).

We have evidence that Nlrp1 activates Casp1, which activates Casp6 in human and mouse brains. Furthermore, our preliminary evidence shows an increase in Casp1 and Casp6 mRNA in J20 brains and a reduction of these in J20+VX-765 (FIG. 6). Therefore, without being bound to a particular theory, this raises the possibility that the Casp1-Casp6 neurodegenerative pathway that we found associated with human age-dependent cognitive impairment and Alzheimer disease contributes to the memory deficits and/or pathologies in the J20 mice.

Example 8: Neuron Beading Studies

Methods

EGFP-labeled human primary neurons were either APP$^{WT}$ transfected or serum deprived. Two treatment strategies were employed to determine VX-765's effects on neuronal degeneration: our Pre-Treatment strategy looked at whether VX-765 could block neuronal degeneration when administered 1 hr prior to APP$^{WT}$ transfection or serum deprivation, while our Reversal Treatment strategy looked at whether VX-765 could reverse degenerative effects when administered 48 hrs after APP$^{WT}$ transfection or serum deprivation. Neurons displaying beaded morphology were counted with live imaging and measured as a percentage of the total number of eGFP+ neurons from 24-72 hrs after treatment. The irreversible caspase-1 inhibitor YVAD-fmk was used as positive control in our experiments. Results were obtained from averaging counts for at least 100 eGFP+ neurons per experiment in three independent neuron preparations. Results are shown in FIG. 7.

Results

Figure 7:
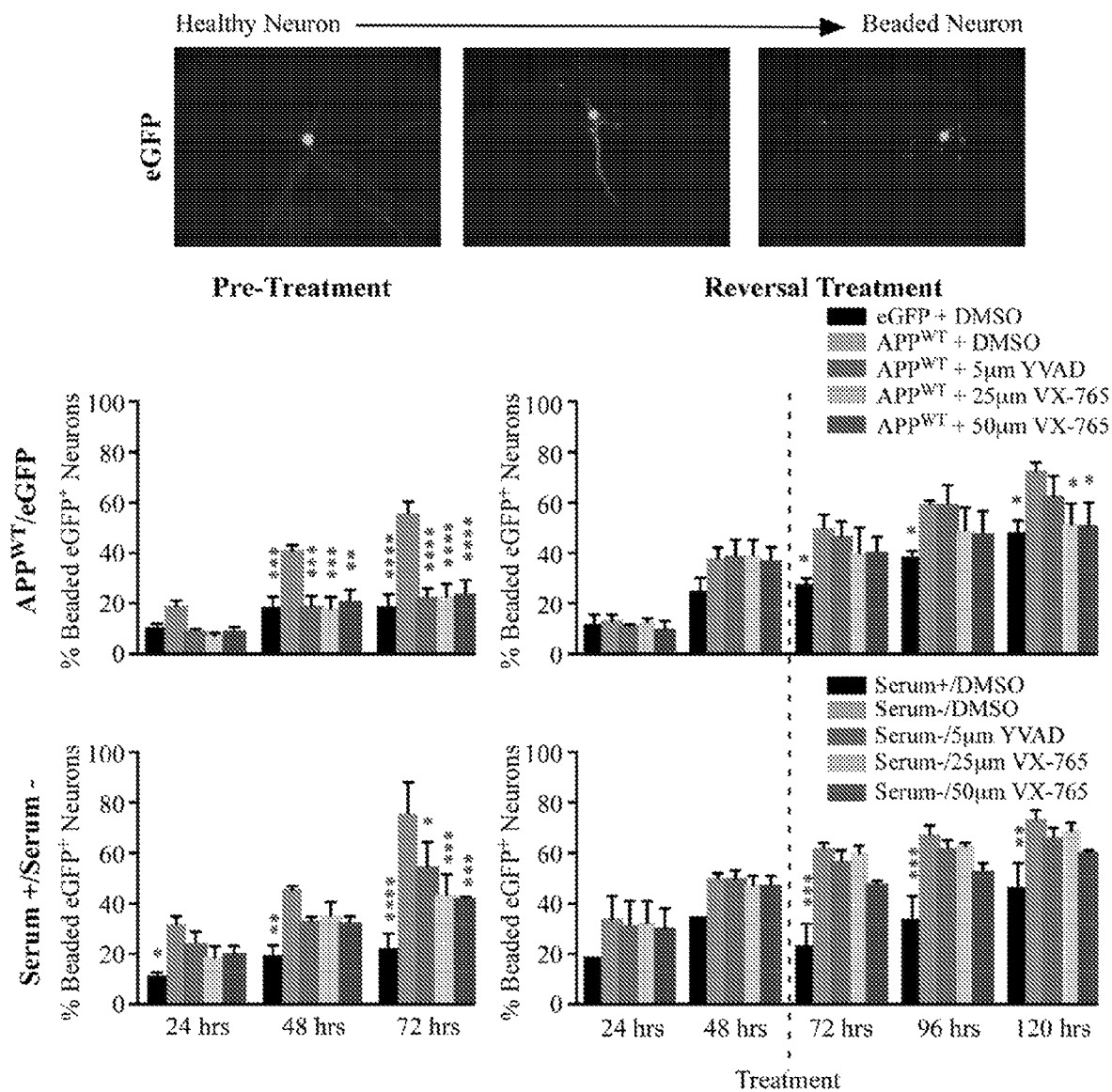
FIG. 7: VX-765 prevents human CNS neuronal degeneration (see Example 8).

The top inserts of FIG. 7 are examples of eGFP-transfected neurons. In a healthy neuron, eGFP was homogeneously distributed within the cell body extending into its neurites. The introduction of a stressor (APP$^{WT}$ transfection or serum deprivation) resulted in the re-distribution of eGFP, gradually appearing as beads-on-a-string within the neurites (beaded neuron).

VX-765 Pre-Treatment (N=3)

VX-765 pre-treatment resulted in a 40% reduction in neuritic beading in APP$^{WT}$-transfected neurons 48 hrs and 72 hrs post transfection, compared to DMSO-treated APP$^{WT}$-transfected neurons (FIG. 7, top left panel). The VX-765-induced reduction was comparable to both our eGFP and YVAD caspase-1 peptide inhibitor control groups. Serum deprivation showed a more protracted response. EGFP+ DMSO showed significantly reduced neuritic beading compared to the APP$^{WT}$+DMSO group across all time points; however, VX-765 treatment was particularly effective in reducing neuritic beading at 72 hrs (FIG. 7, bottom left panel).

VX-765 Reversal Treatment (N=3)

Our reversal treatment strategy where we administered VX-765 48 hrs after the stressor (APP$^{WT}$ or serum deprivation), resulted in an overall larger percentage of beaded neurons across all our treatment groups. APP$^{WT}$ transfection resulted in 40-80% beading and was significantly increased compared to our eGFP+DMSO group from 72-120 hrs (FIG. 7, top right panel). VX-765 treatment was able to decrease beading at 120 hrs (or 72 hrs after treatment). The caspase-1 peptide inhibitor YVAD was not able to reverse neuritic beading at any time-point. Serum deprivation (Bottom right figure) resulted in a significant increase in neuritic beading compared to our Serum+control group from 72-120 hours. However, neither YVAD nor VX-765 were able to reverse neuritic beading.

Example 9: VX-765 Rescues Cognitive Deficits and Hyperactivity in Symptomatic APP$^{Sw/Ind}$ J20 Mice VX-765 potently and specifically inhibited recombinant human Casp1 (IC$_{50}$ 3.68 nM) relative to human Casp2 to 10

Figure 14A:
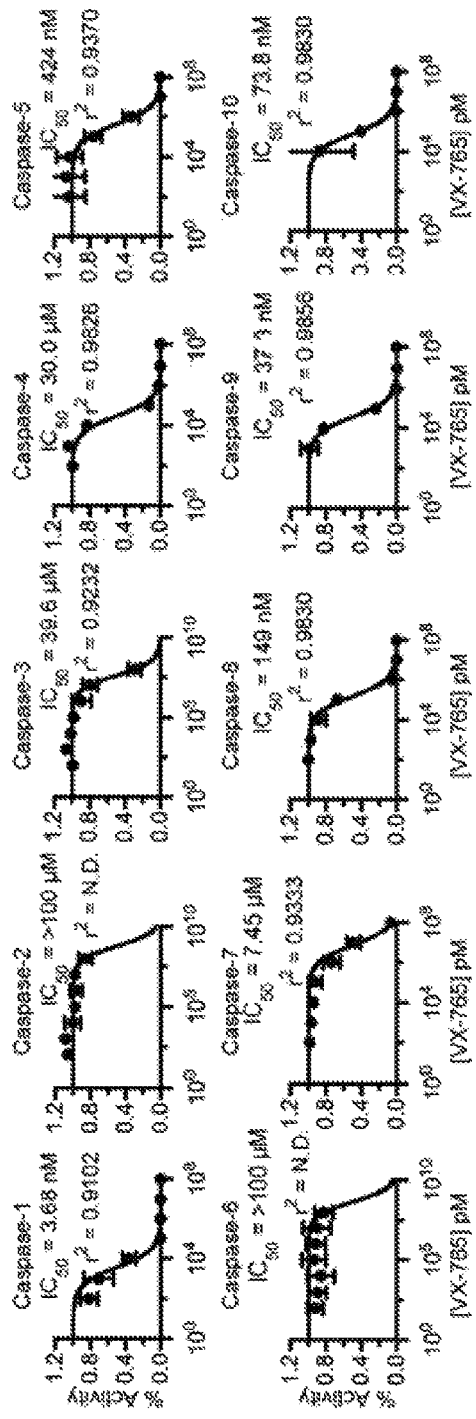
FIG. 14: Selectivity and blood brain permeability of VX-765 and VRT-043198. (a-b) IC$_{50}$ of VX-765 (a) and VRT-043198 (b) against human Casp1-10. (c-d) IC$_{50}$ of VX-765 (c) and VRT-043198 (d) against mouse Casp1 and Casp11. (e) Blood brain barrier permeability and presence of VX-765 and VRT-043198 in 3 wild type and 4 J20 mice brain cortex and hippocampus and in plasma. Ratios of brain levels to plasma levels are calculated.
Figure 14B:
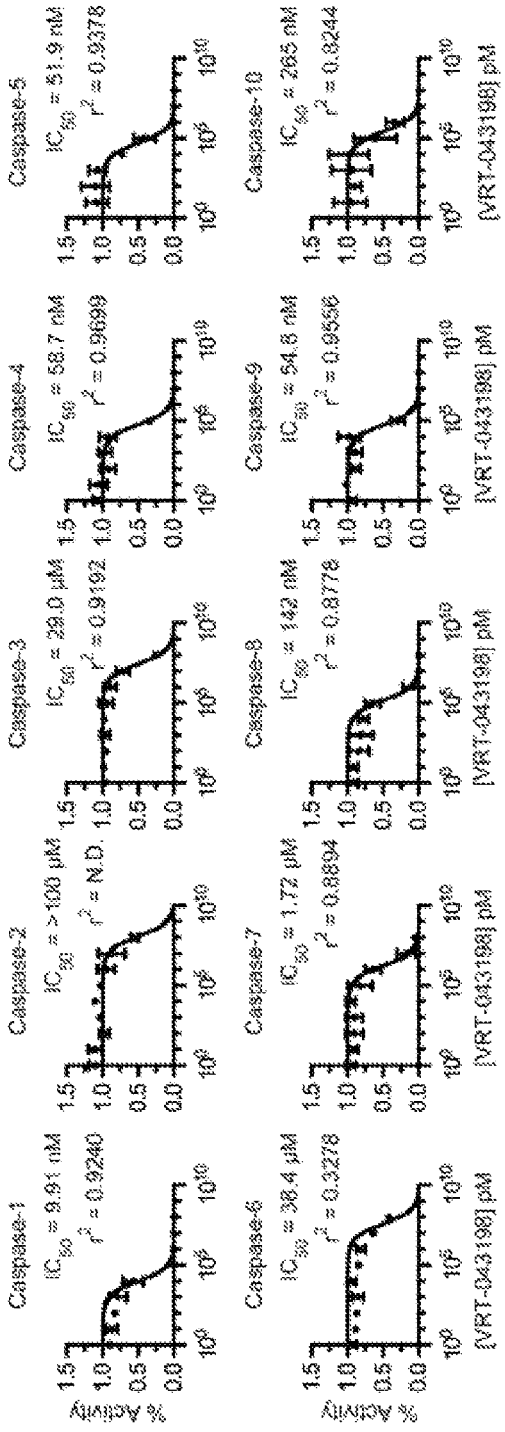

(FIG. 14a). Similarly, mouse recombinant Casp1 ($IC_{50}$ 52.1 nM) was strongly inhibited compared to inflammatory mouse Casp11 (FIG. 14c). VRT-043198, the metabolized VX-765 pro-drug, had an $IC_{50}$ of 9.91 nM against human Casp1 and 18 nM against mouse Casp1 (FIG. 14b & d). VX-765 crossed the blood brain barrier of WT and J20 mice, was metabolized into VRT-043198, and reached physiologically active concentrations in both the hippocampus and cortex (FIG. 14e).

Figure 8A:
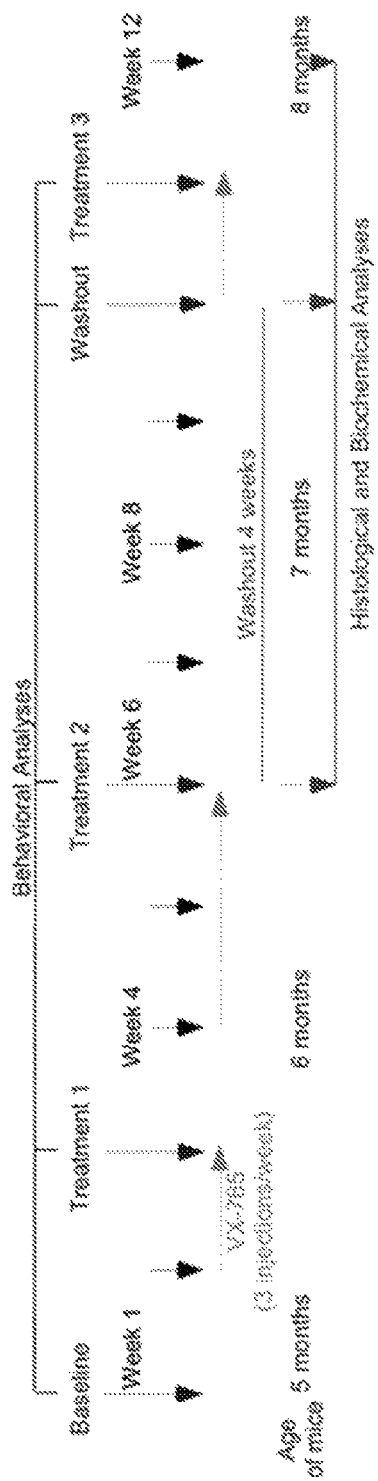
FIG. 8: VX-765 treatment restores cognitive function in J20 mice. (a) Experimental paradigm. Intraperitoneal vehicle-injected wild type (WT+Vehicle; n=13) and J20 mice (J20+Vehicle: n=9), and VX-765-injected J20 mice (J20+VX-765: n=9) mice were behaviourally assessed at 5 different time-points: baseline before treatment (baseline untreated J20 were grouped together; n=18), after 3 IP injections/wk of VX-765 or vehicle (Treatment 1), after 6 additional injections over 2 weeks (Treatment 2), after 4-week Washout period, and after an additional 3 injections in one week (Treatment 3). Mice were sacrificed at 8 months of age after Treatment 3 (b) NOR Discrimination index (Treatment main effect, $F(2,20)=85.8$, $p<0.0001$; Time main effect, $F(4,80)=4.188$, $p=0.0039$; Treatment×Time interaction, $F(8,80)=3.599$, $p=0013$, two-way repeated-measures ANOVA, Dunnett's post-hoc compared to J20+Vehicle). (c) Distance traveled during Open Field task. Data analyzed by repeated measures two-way ANOVA (Treatment main effect, $F(2,19)=11.47$, $p=0.0005$; Treatment×Time interaction, $F(8,76)=5.69$, $p<0.0001$, two-way repeated-measures ANOVA, Dunnett's post-hoc compared to J20+Vehicle). (d-i) Barnes maze analysis. Learning acquisition (d,g), probe test primary latency and errors (e,h), and target hole preference (f,i); # of pokes of each hole labelled +1 to +9 to the right or −1 to −9 to the left of the target hole during the probe) after Treatment 2 (d-f) and Washout (g-i). Probe tests were analyzed (Treatment 2 primary latency, $F(2,52)=5.879$, $p=0.0050$; Treatment 2 primary errors, $F(2,52)=9.998$, $p=0.0002$; Washout primary latency, $F(2,22)=4.076$, $p=0.0312$; Washout primary errors, $F(2,22)=10.84$, $p=0.0005$, ANOVA, Tukey's post-hoc). * $p<0.05$, *$p<0.001$, **$p<0.0001$.
Figure 8B:
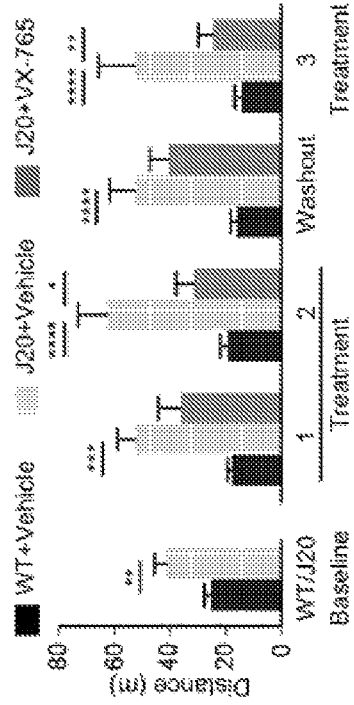
Figure 8C:
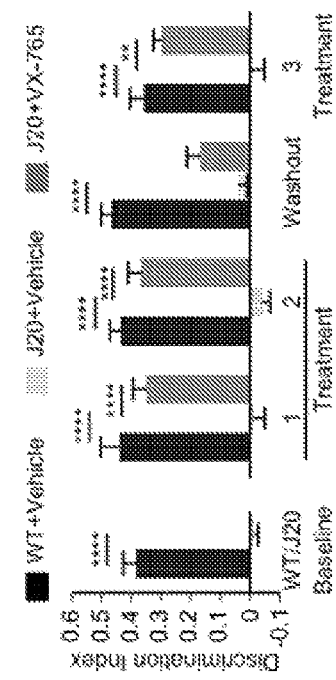
Figure 8D:
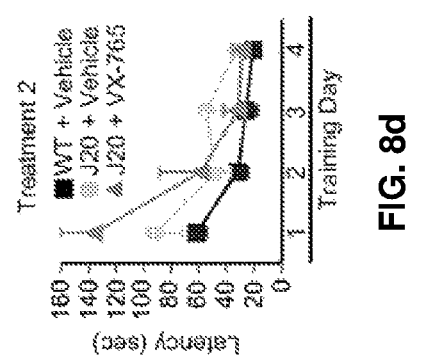
Figure 8E:
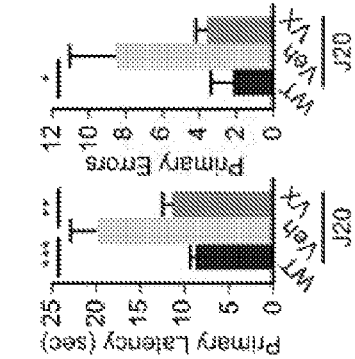
Figure 8F:
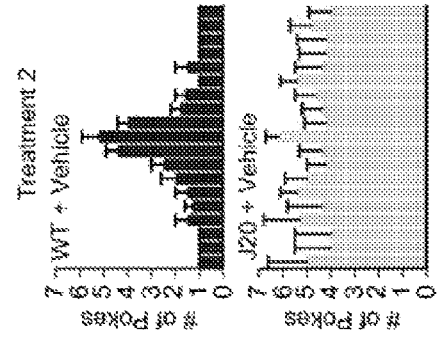
Figure 8G:
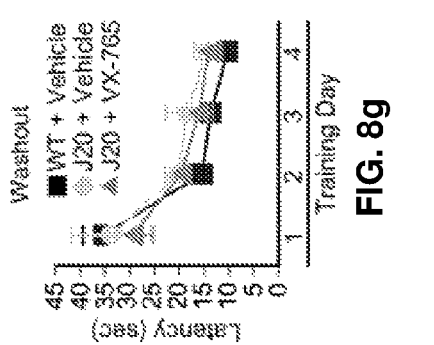
Figure 8H:
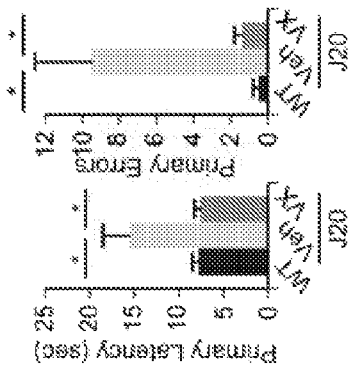
Figure 8I:
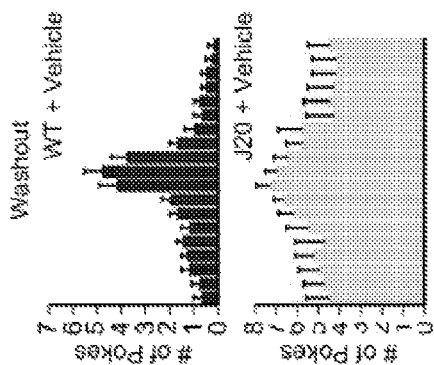
Figure 15A:
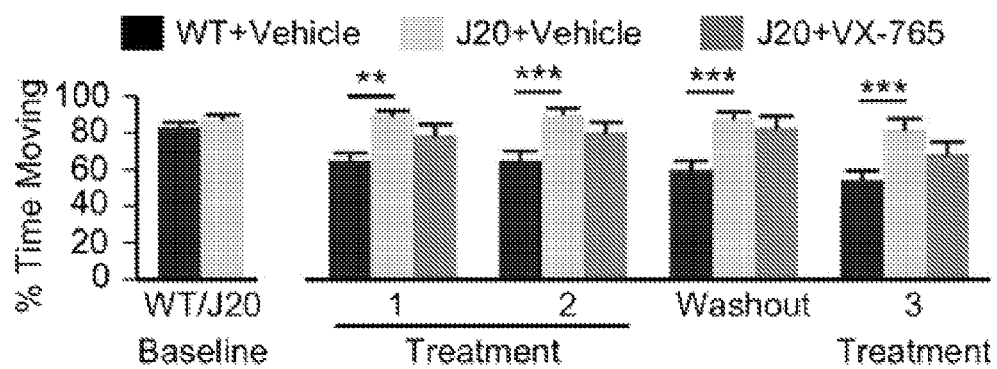
FIG. 15: Behavioural assessment of vehicle-treated WT and J20 mice and 50 mg/kg VX-765-treated J20 mice. (a) % time moving (Treatment main effect, F(2,28)=10.89, p=0.0003; Time main effect, F(3,84)=6.644, p=0.0004, two-way repeated-measures ANOVA, Dunnett's post-hoc compared to J20+Vehicle, p<0.01, *p<0.001) and % time in periphery (b) before treatment (Baseline), treatment 1, 2, washout, and treatment 3 as described in FIG. 1a. (c) # of touches of familiar or novel objects for each individual mouse at each test session showed consistent behaviour in all mice groups. Pre-exposure indicates mice performance with two identical objects, familiar and novel indicates # of touches of the familiar object and the novel object, respectively, during the test (d) Hyperactivity demonstrated by distance travelled in the open field task of individual vehicle-treated WT and J20 mice and VX-765-treated mice. (e) % alternation in Y maze apparatus shows a difference between groups only after treatment 1 and washout (two-way repeated measures ANOVA, Dunnett's post-hoc compared to J20+Vehicle, *p<0.05, **p<0.01).
Figure 15B:
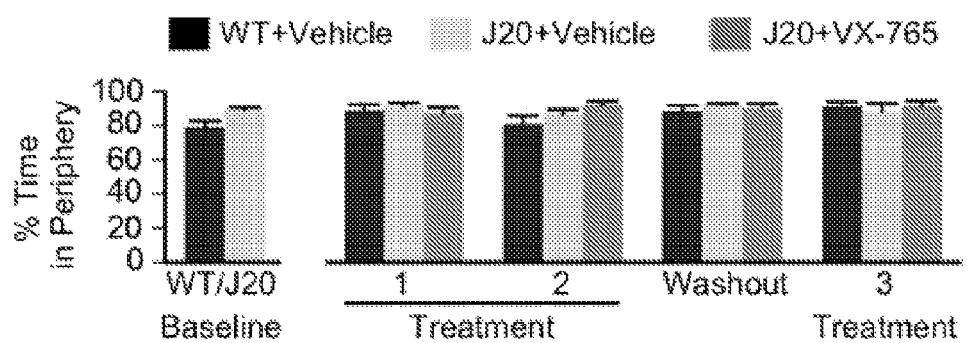
Figure 15C:
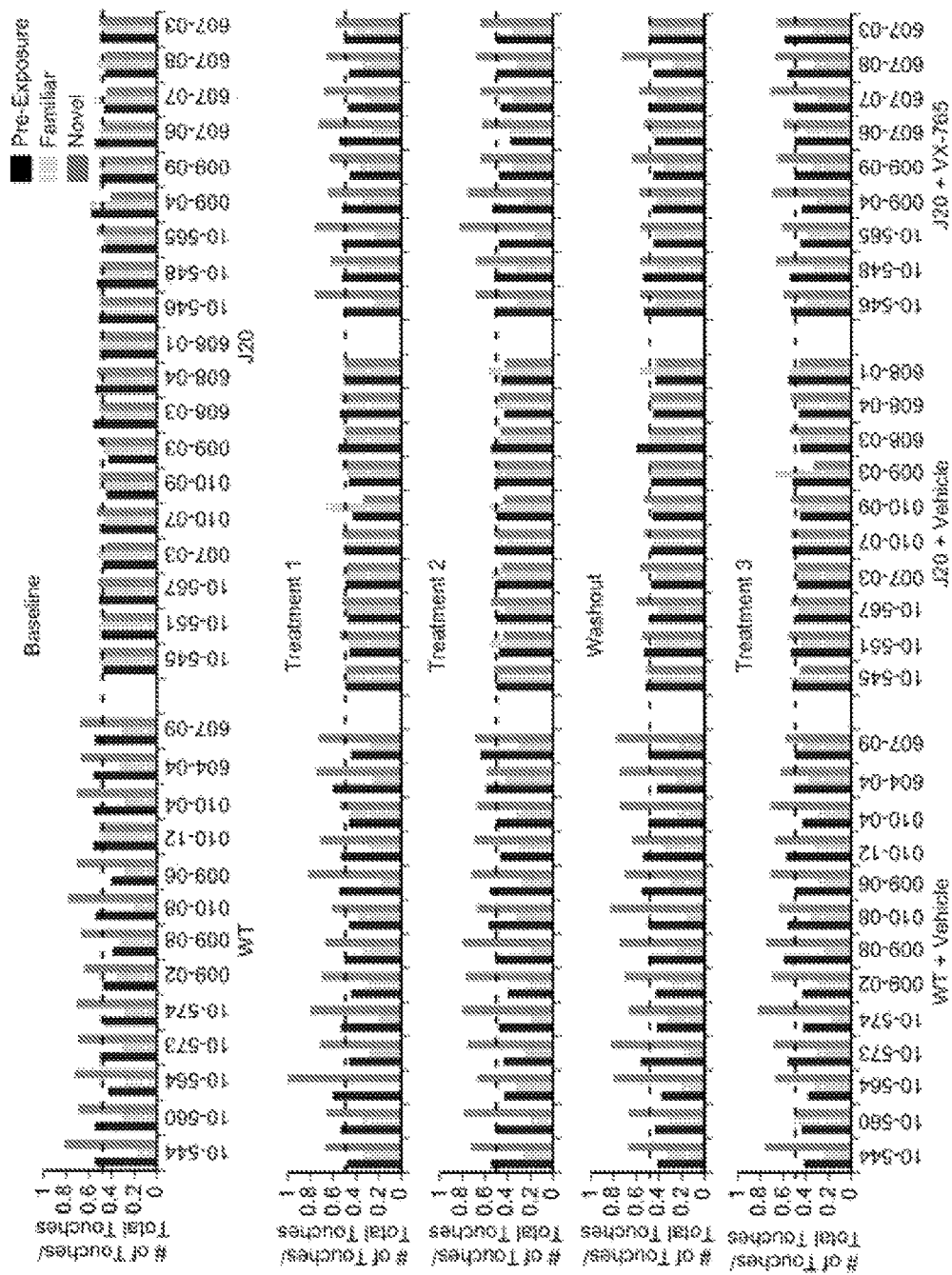
Figure 15D:
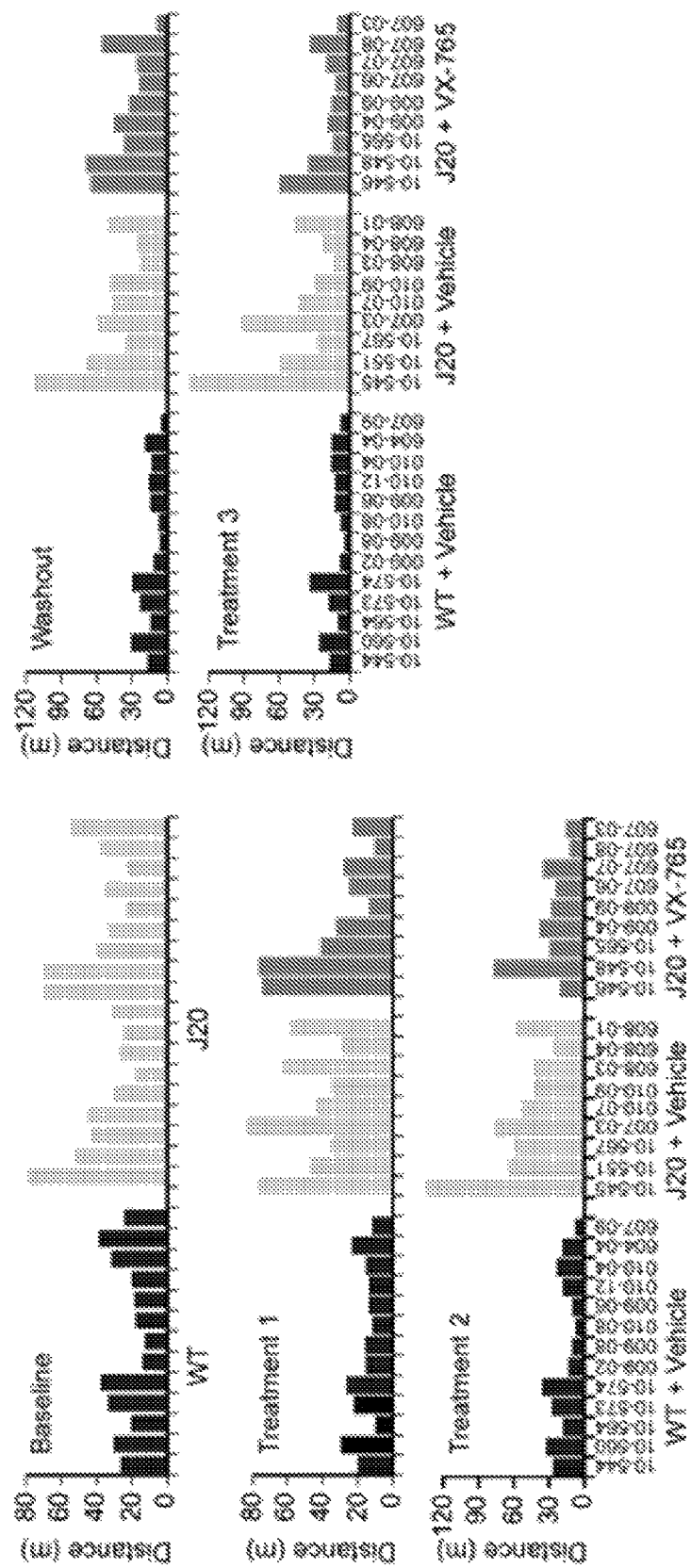
Figure 15E:
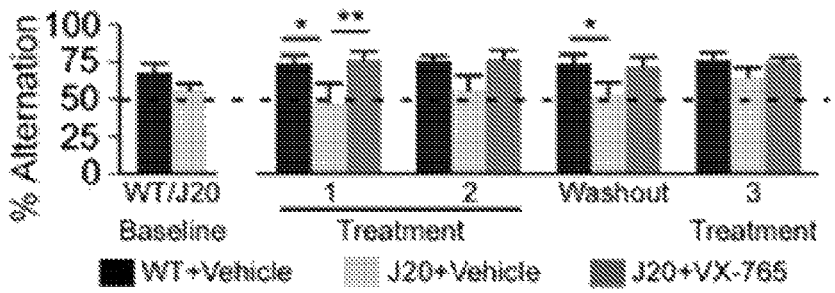

Five month old mice were behaviorally and longitudinally assessed before treatment (baseline), after 3 injections/week of 50 mg/kg VX-765 (Treatment 1; T1), after an additional 2 weeks of injections (Treatment 2; T2), after 4 weeks without treatment (Washout; WO), and after 3 more injections/week (Treatment 3; T3) before sacrificing the mice at 8 months of age as illustrated in FIG. 8a. At baseline, J20 and littermate WT mice showed normal motivation behavior (FIG. 15a) and did not exhibit thigmotaxis indicative of anxiety (FIG. 15b), but showed a strong deficit in the novel object recognition (NOR) episodic (retention) memory test (FIG. 8b). J20 NOR deficits were reversed and reached near-normal levels after VX-765 T1 and T2. J20 NOR deficits reappeared after the WO period and disappeared again after T3. Results were consistent across individual mice (FIG. 15c). J20 mice hyperactivity, measured by the distance travelled in the open-field task, was attenuated by VX-765 only after T2, reappeared after WO, and again was significantly reduced after T3 (FIGS. 8c & 15d). No significant learning deficits were observed in the Barnes maze spatial memory test at T2 amongst the three groups during the 4 day training period (FIG. 8d). However, during the probe test, the primary latency, primary errors (FIG. 8e) and the ability to find the target (T) escape hatch (FIG. 8f) were clearly impaired in vehicle-injected J20 compared to WT littermates. VX-765 eliminated these spatial memory deficits in J20 mice. After WO, all mice performed well during the training phase of the Barnes maze (FIG. 8g). VX-765-injected, but not vehicle-injected, J20 mice appeared normal in primary latency and errors, suggesting spatial memory retention even after a 1 month period without drug (FIG. 8h). The VX-765-injected mice also performed better than vehicle-injected J20 mice in their ability to find the target hatch (FIG. 8i). J20 mice performance in the Y maze working memory task was consistently low but not always statistically different from WT or treated J20 mice (FIG. 15e).

Figure 9:
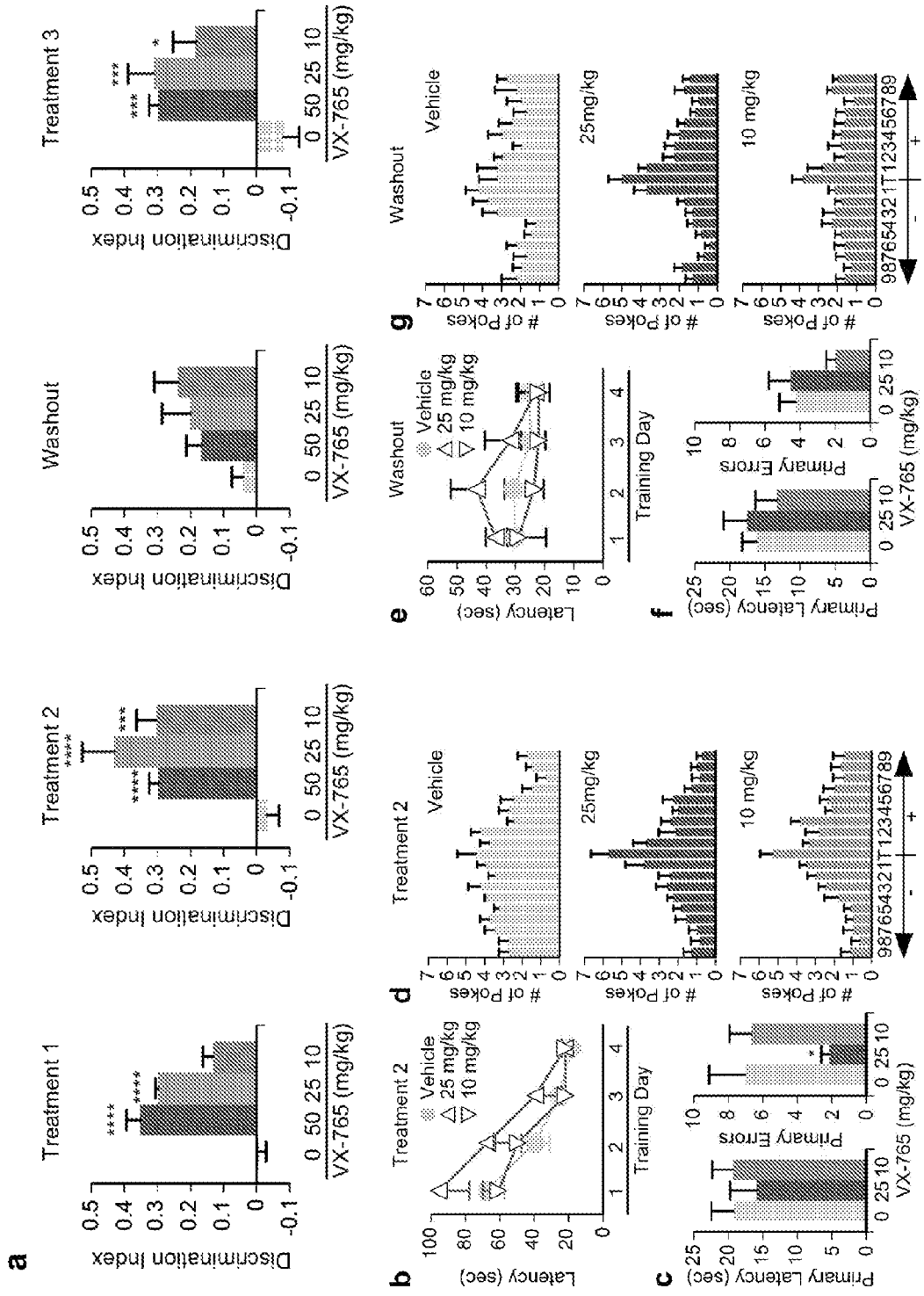
FIG. 9: VX-765 dose-dependently restores cognitive function in J20 mice. (a) NOR discrimination index after VX-765 dose response at Treatment 1 ($F(3,24)=20.42$, $p<0.0001$, ANOVA, Dunnett's post-hoc compared to J20 0 mg/kg), Treatment 2 ($F(3,23)=12.83$, $p<0.0001$, ANOVA, Dunnett's post-hoc compared to J20 0 mg/kg), Washout, and Treatment 3 ($F(3,23)=8.828$, $p=0.0004$, ANOVA, Dunnett's post-hoc compared to J20 0 mg/kg). Note that the 50 mg/kg dose was not performed at the same time and is placed here for comparison purposes only. Nevertheless, the discrimination index was stable between experiments (b-g) Barnes maze Treatment 2 (b-d) and Washout (e-g) learning acquisition (b,e), probe test (c,f), and target hole preference (d,g). For T2 primary errors, $F(2,14)=5.69$, $p=0.0155$, ANOVA, Dunnett's post-hoc compared to J20+Vehicle. * $p<0.05$, *$p<0.001$, **$p<0.0001$.
Figure 16A:
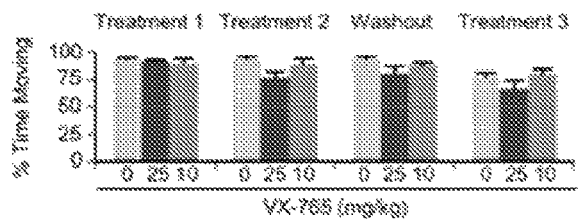
FIG. 16: Behavioural assessment of vehicle-, or 25 or 10 mg/kg VX-765-treated J20 mice. (a) % time moving and (b) % time in periphery of vehicle- (0), 25 or 10 mg/kg VX-765-treated mice. (c) NOR # of touches of familiar and novel object for each individual mouse before (baseline) and after Treatment 1, Treatment 2, Washout, and Treatment 3 after vehicle- (0), 25 or 10 mg/kg VX-765 treatment. Two mice (J20+Vehicle, J20+VX-765 10 mg/kg) did not respond during the behavioural test and was removed from the analysis. (d-e) Hyperactivity measured by distance travelled in the Open Field task (d) in vehicle- (0), 25 or 10 mg/kg VX-765-treated mice at Treatment 1, Treatment 2 (F(2,14)=4.106, p=0.0395, ANOVA, Dunnett's post-hoc compared to J20+Vehicle), Washout, and Treatment 3. (e) Hyperactivity of each individual mice in the Open Field task. Two mice (J20+Vehicle, J20+10 mg/kg VX-765) did not respond after Treatment 2 and were removed from the analysis.
Figure 16B:
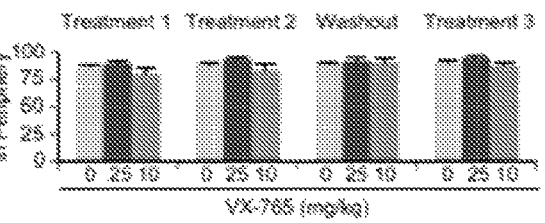
Figure 16C:
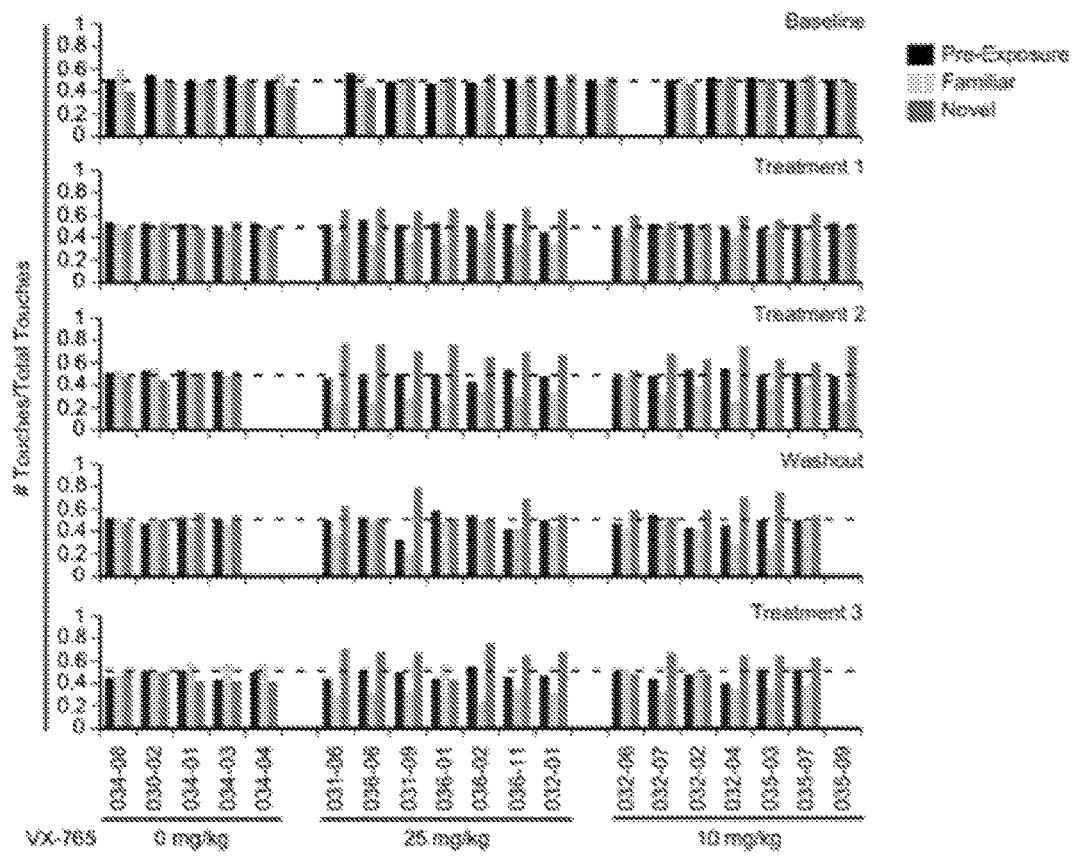
Figure 16D:
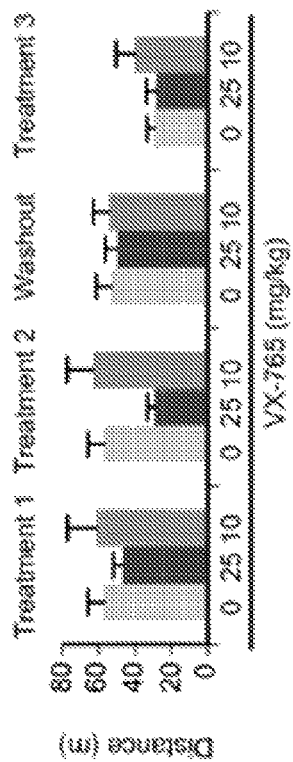
Figure 16E:
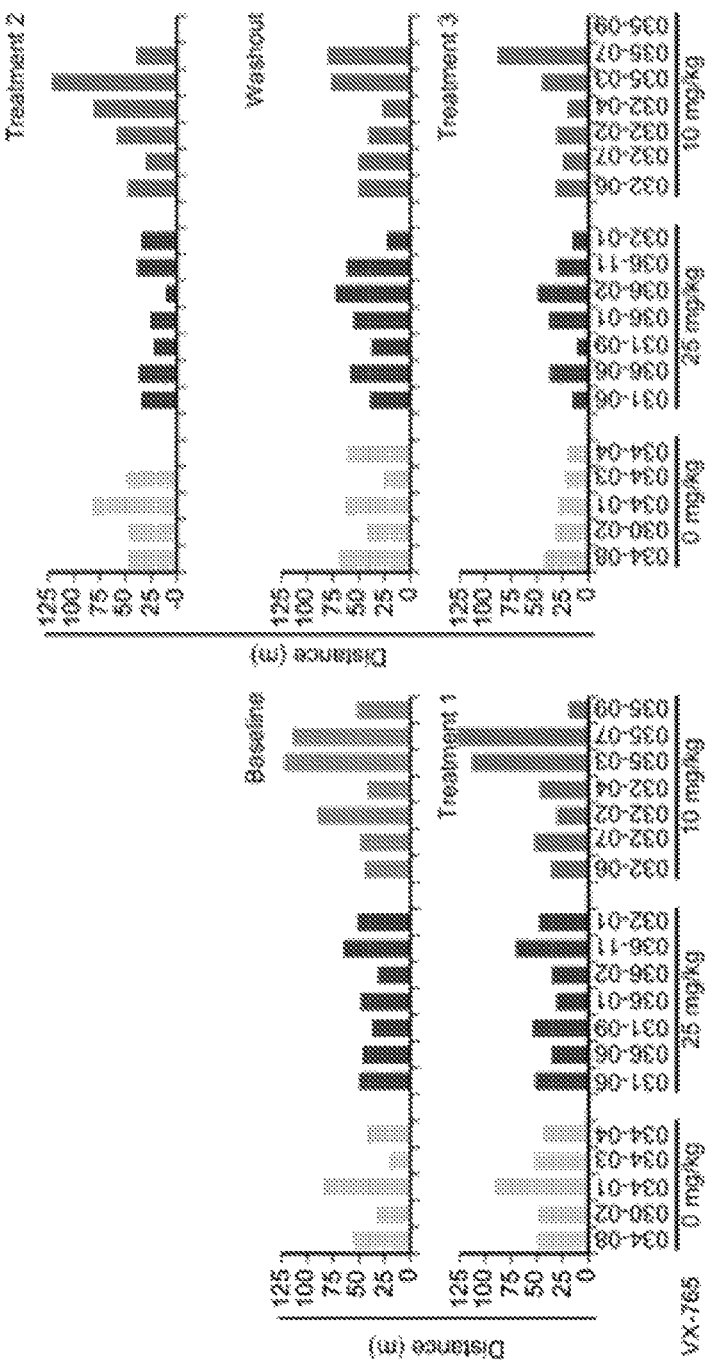

VX-765 was administered at 25 and 10 mg/kg to assess the dose-response of J20 to VX-765 (FIG. 9). All groups of mice showed normal motivation (FIG. 16a) and thigmotaxic (FIG. 16b) behaviour. NOR discrimination index was normalized with 25 mg/kg dose at T1 and T2, deficits reappeared after WO, and returned to normal at T3, similar to the results with the 50 mg/Kg dose (FIGS. 9a & 16c). Mice treated with 10 mg/kg showed normalized NOR behavior only after T2, and the effect was washed out and reappeared after T3. J20 hyperactivity showed a non-significant improvement at T2 with 25, but not 10, mg/kg (FIG. 16d & e). In the Barnes maze assessed after T2, no significant difference was observed in training (FIG. 9b), and the J20 remained impaired in primary latency at both the 25 and 10 mg/kg dose (FIG. 9c). However, primary errors were decreased with 25 mg/kg and both doses showed the mice improved in their ability to recognize the escape hatch during the probe test (FIG. 9d). After the washout period, mice latency to find the escape hatch was more rapid initially and similar in time to that of the naïve mice tested after T2 (FIG. 9e). No significant difference was observed in primary latency and errors, with or without drug during the probe test (FIG. 9f). Furthermore, mice treated with 25 mg/kg, but not 10 mg/kg, retained the ability to recognize the position of the escape hatch (FIG. 9g). Together, these results demonstrate a VX-765 dose-response effect in reversing J20 episodic and spatial memory deficits.

Figure 17:
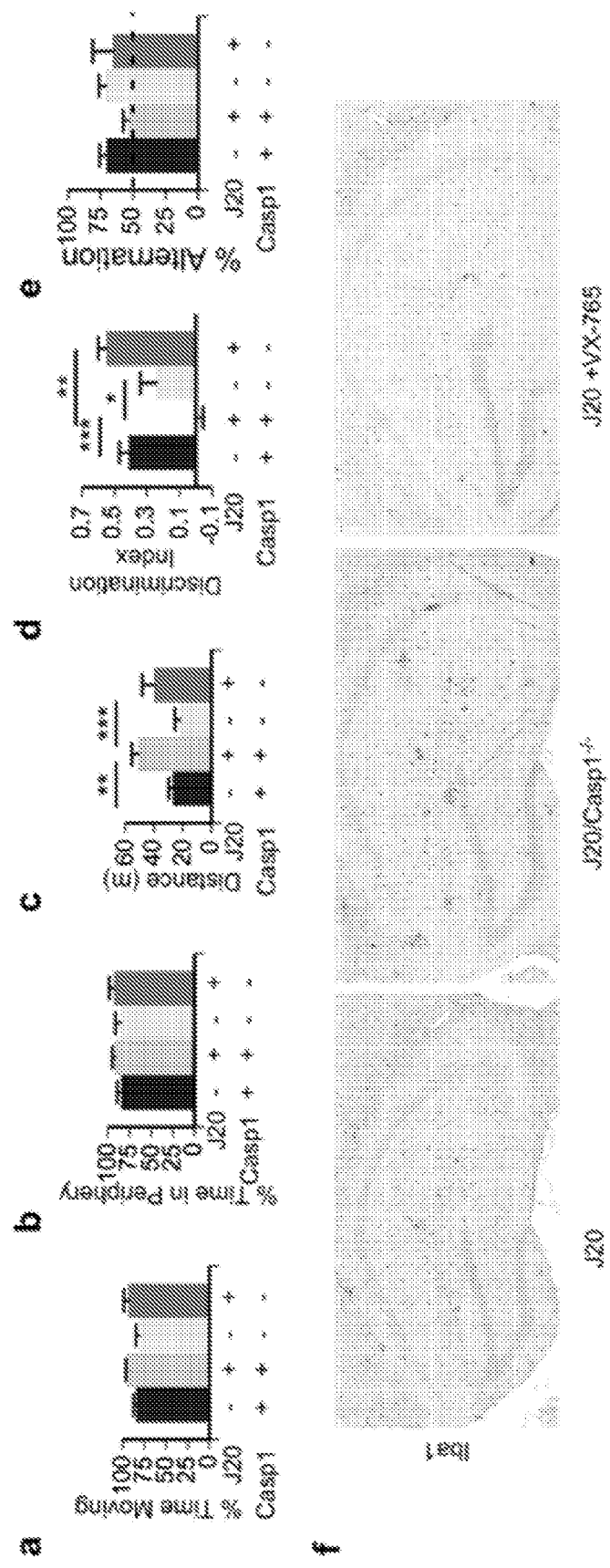
FIG. 17: Behavioural assessment of J20 mice on a Casp1 null background. (a) % time moving, (b) % time in periphery, (c) distance travelled (F(3,17)=10.86, p=0.0003, ANOVA, Dunnett's post-hoc compared to J20, p<0.01, *p<0.001, (d) NOR discrimination index (F(3,17)=10.02, p=0.0005, ANOVA, Dunnett's post-hoc compared to J20, *p<0.05, p<0.01, *p<0.001), and (e) % alternation in Y maze of WT/WT (J20−) or J20/WT (J20+) mice with (Casp1+) and without (Casp1−) the Casp1 gene. (f) Iba1 immunopositive staining in 8 month old vehicle-treated J20, J20/Casp1$^{−/−}$, and VX-765-treated (T3) mice hippocampi.

To confirm that the VX-765 effect on re-establishing normal cognition in J20 mice is due to Casp1 inhibition, J20 mice were generated with a Casp1 null background (J20/Casp1$^{-/-}$) and behaviorally assessed at 8 months of age, corresponding to the age of J20 mice after VX-765 T3. Similar to 5 month old J20 mice, 8 month old J20 showed normal locomotor activity and a lack of anxiety (FIG. 17a & b), were hyperactive (FIG. 17c), and had a strong NOR deficit (FIG. 17d). The J20/Casp1$^{-/-}$ mice retained their hyperactivity (FIG. 17c), but performed normally in NOR (FIG. 17d) and in the Y maze (FIG. 17e). Together, these results indicate that VX-765 reverses episodic and spatial memory deficits by inhibiting Casp1 in J20 mice.

Example 10: VX-765 Reverses Neuroinflammation in J20 Mice

Figure 10D:
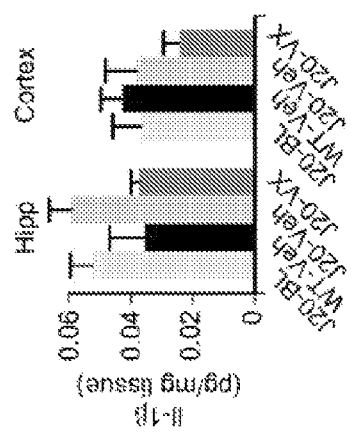
FIG. 10: VX-765 reverses neuroinflammation in J20 mice. (a) Iba-1 positive microglia immunohistographs in the stratum lacunosum molecular area of the hippocampus and S1 of cortex (Scale bar=50 μm). (b) Stereological quantification of Iba-1$^+$ microglia for WT+Vehicle (n=6), J20+Vehicle (n=5), and J20+VX-765 (n=4) in the hippocampus from the pyramidal cell layer to the stratum lacunosum molecular layer ($F(2,11)=58$, $p<0.0001$) and cortex ($F(2,11)=39.95$, $p<0.0001$, ANOVA, Dunnett's post-hoc compared to J20+Vehicle, ***$p<0.001$). (c) Average percentage distribution of morphological microglial subtypes 1 (black (lowermost) bar), 2 (light grey bar), 3 (dark grey bar) and 4 (black (uppermost) bar). (d) Il1-$\beta$ pg/mg levels measured by ELISA in pre-treated J20 at 5 months of age and in treated WT and J20 8 months of age. (e) Astroglial GFAP$^+$ immunohistographs.
Figure 10E:
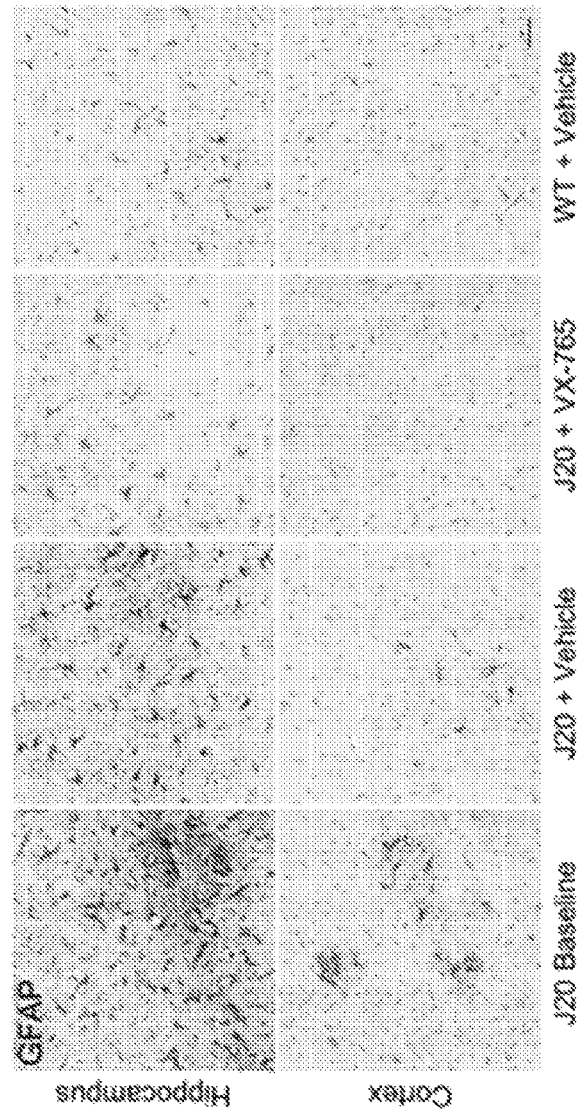
Figure 18:
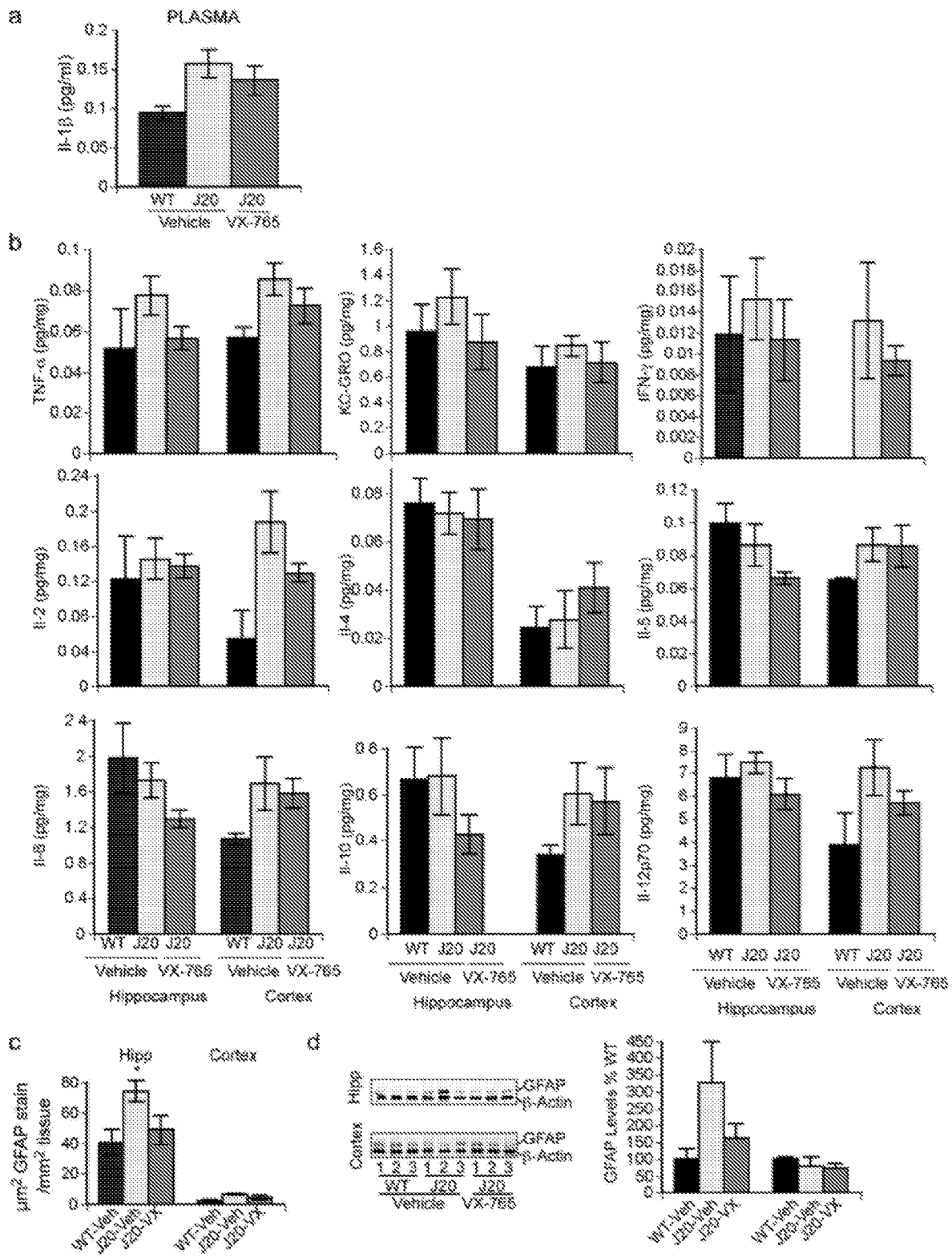
FIG. 18: ELISA measures of cytokines in vehicle-treated WT and J20 mice and VX-765-treated J20 mice. (a) Plasma levels of Il-1β in mice after T3. (b) Cytokine levels in vehicle-treated WT and J20 and in VX-765-treated J20 brain hippocampi and cortex. (c) GFAP immunostaining density in vehicle-treated WT (n=6) and J20 (n=5) and in VX-765-treated J20 (n=4) brain hippocampi (F(2,12)=5.234, p=0.0232, ANOVA, Dunnett's post-hoc compared to WT+Vehicle, *p<0.05) and cortex. (d) Western blots and quantitative analyses of GFAP in vehicle-treated WT and J20 and in VX-765-treated J20 brain hippocampi and cortex.

Increased Iba-1 positive microglia were observed in the hippocampus and cortex of vehicle-treated J20 mice, but were reduced to WT levels in the CA1 stratum radiatum of VX-765-treated J20 hippocampus, (FIG. 10a). Iba1 positive microglia in VX-765-treated hippocampus were lower than those of the pre-treated 5 month old J20 mice brains, indicating a reversal of inflammation by VX-765 treatment in this region (J20 baseline; FIG. 10a). Overall, the number of Iba1+ microglia measured from the pyramidal cell layer to the stratum lacunosum molecular layer of the hippocampus CA1 region returned to normal after the VX-765 treatment (FIG. 10b). However, Iba1 positive microglia were still evident and associated with the remaining Aβ plaques in the CA1 stratum lacunosum molecular and dentate gyrus regions of the hippocampus (FIG. 17f). The reduction in microglial activation via inhibition of Casp1 was confirmed in the J20/Casp1$^{-/-}$ hippocampus (FIG. 17f). However, more activated microglia remained, especially in the stratum lacunosum molecular and dentate gyrus regions of the hippocampus, in the J20/Casp1$^{-/-}$ brains than in the VX-765-treated brains. Microglial activation, measured morphologically[37], indicated more resting, and less activated, microglia in VX-765-treated J20 hippocampus and cortex, than in vehicle-treated J20 (FIG. 10c). Compared to WT, hippocampal Il-1β was increased in J20, and reduced after VX-765 treatment (FIG. 10d). No changes were seen in cortex or plasma Il-1β levels, although the VX-765-treated cortex tended towards a reduction in Il-1β (FIG. 10d & FIG. 18a). No significant difference was observed in other inflammatory protein levels, although TNF-α, KC-GRO, and IFN-γ, were slightly elevated in vehicle-treated J20 and normalized in VX-765-treated J20 (FIG. 18b). It is important to consider that the ELISA assay measures both pro- and mature Il-1β and that Casp1 inhibition hinders the release of mature Il-1β and other cytokines, thereby preventing their rapid turnover[8]. Increased GFAP astrogliosis in the cortex and hippocampus of J20 mice was also almost returned to WT levels with VX-765 treatment (FIG. 10e & FIG. 18c & d). These results indicate that VX-765 treatment has reversed both microglial and astroglial activation in the J20 brains.

Figure 19:
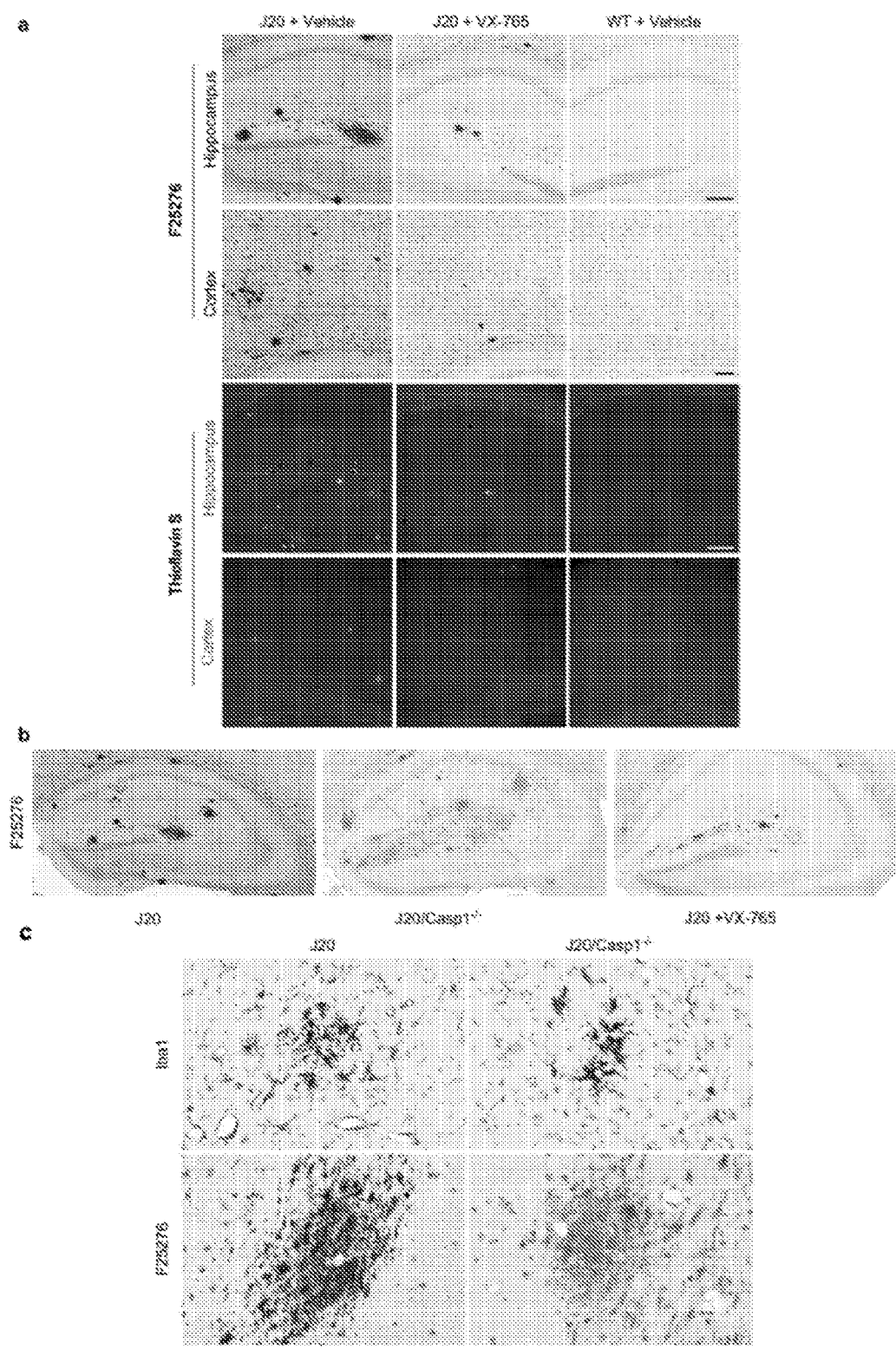
FIG. 19: Aβ stained with Thioflavin S or anti-A$β_{1-40}$ F25276 antiserum in mice hippocampi or cortex. (a) Comparison of anti-Aβ immunostaining and thioflavin S stained Aβ in 8 month old vehicle-treated WT and J20 and in VX-765-treated J20 brain hippocampi and cortex (after T3). (b) Anti-Aβ F25276 immunopositive staining in 8 month old vehicle-treated J20, J20/Casp1−/−, and VX-765-treated (T3) mice hippocampi. (c) Higher magnification of Aβ and Iba1 immunopositive deposits in 8 month old vehicle-treated J20, J20/Casp1$^{-/-}$, and VX-765-treated (T3) mice hippocampi.

Example 11: VX-765 Prevents the Accumulation of Soluble and Deposited Aβ in J20 Mice Brains Increased deposited thioflavin S (FIG. 19a) and immunopositive Aβ levels were substantially reduced in the VX-765 treated hippocampus and cortex compared to vehicle-injected J20 mice brains (FIG. 11a-b). However, Aβ deposits did not completely disappear and were comparable to those observed in pre-treated 5 month old J20 mice brains (FIG. 11a). These remaining Aβ deposits were mainly localized in the stratum lacunosum molecular and dentate gyrus regions of the hippocampus, with rare deposits in cortex (FIG. 19b). Compared to J20/Casp1$^{-/-}$ mice brains where Aβ deposits appear diffuse and cover most of the hippocampus, deposits remaining after VX-765 treatments were more compact and had fewer activated microglia (FIG. 17f, FIG. 19b & c). RIPA-soluble and formic acid soluble Aβ$_{42}$ over total Aβ$_{38+40+42}$ levels were also reduced in the hippocampus and cortex (only for RIPA-soluble) of VX-765-treated mice and comparable to those measured in the 5 month old pre-treated J20 brains (FIG. 11c,e). RIPA soluble total Aβ (FIG. 11d) or Aβ$_{38}$ (FIG. 11g) was higher in the 5 month old hippocampus than in the 8 month old vehicle- or VX-765-treated J20 mice, whereas Aβ$_{40}$ levels were similar in all groups (FIG. 11h). However, Aβ$_{42}$ was reduced in the hippocampus after the VX-765 treatment (FIG. 11i). Formic acid soluble total Aβ was strongly decreased in hippocampus and cortex (FIG. 11f), and all three subtypes of Aβ were less abundant in VX-765 J20 hippocampal and cortical tissues (FIG. 11j-l). The reduction in soluble or deposited Aβ$_{42}$ levels was not due to a decrease in the levels of APP mRNA or protein in J20 mice; in fact, APP levels increased in the VX-765-treated hippocampus and cortex (FIG. 11m). Increased degradation of Aβ is unlikely since no significant change in the levels of insulin degrading enzyme (IDE) or neprilysin mRNA levels was observed (FIG. 11n & o). Together, these results indicate that VX-765 treatment stopped the progressive deposition of Aβ in J20 brains possibly by reducing the ratio of Aβ$_{42}$ relative to total Aβ levels.

Figure 12:
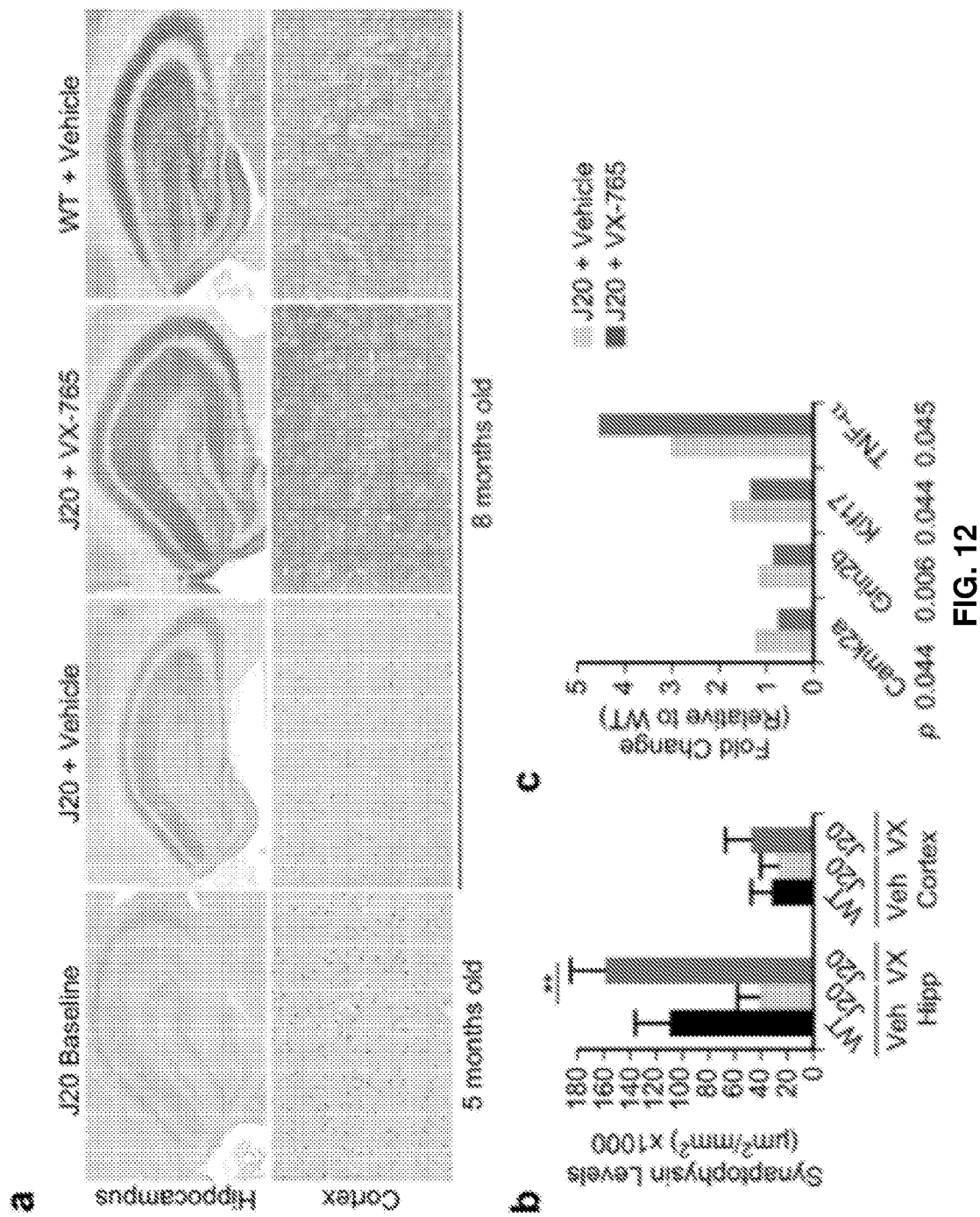
FIG. 12: VX-765 reverses loss of synaptophysin immunohistological staining in J20 mice. (a) Immunohistological micrographs from pre-treated 5 month old J20 and 8 month old vehicle or VX-765 treated WT or J20 mouse hippocampus and cortex. (b) Quantitative analysis comparing synaptophysin immunostaining density between WT+Vehicle (n=4), J20+Vehicle (n=4), and J20+VX-765 (n=4) in the hippocampus (F(2,9)=7.974, p=0.0102, ANOVA, Tukey's post-hoc, * p<0.05) and cortex. (c) Significantly altered synaptic protein mRNA levels in vehicle or VX-765-treated J20 mice hippocampi. Kruskall-Wallis shows a significant difference between WT+Vehicle, J20+Vehicle and J20+VX.

Example 12: VX-765 Normalizes Detection of Synaptophysin by Immunohistochemistry in J20 Mice Brains At 5 months of age, there was a significant decrease in immunopositive synaptophysin levels in the J20 hippocampus (FIG. 12a). Synaptophysin levels remained low in 8 month old vehicle-treated J20 hippocampus but was significantly increased and returned to normal levels in VX-765-treated mice hippocampi (FIG. 12a & b). Measures of 84 different synaptic gene mRNA levels in three vehicle-treated and three VX-765-treated mice hippocampi revealed significant differences in the mRNA levels of four additional genes that are involved in synaptic function: Camk2a, Grin2b, Kif17, and TNF-α (FIG. 12c). TNFα protein levels increased slightly in J20 mice hippocampi and returned to normal with the VX-765 treatment (FIG. 18b). These results indicate a normalizing effect of VX-765 on several synaptic components that may account for the reversal to normal cognition.

Figure 13D:
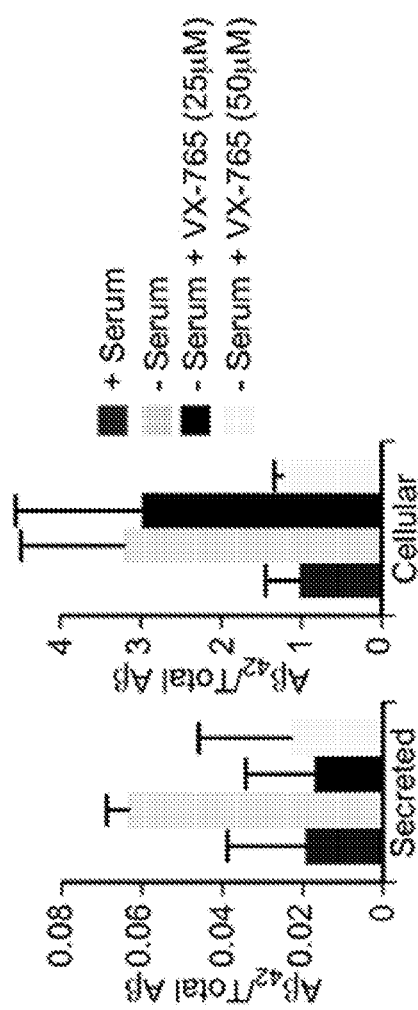
FIG. 13: VX-765 protects CNS primary human neurons (HPN) against APP- or serum deprivation-mediated neuritic beading. (a) MTT assay with increasing dose of VX-765. (b) Fluorescent micrographs showing homogeneous distribution of EGFP in normal neurons and neuritic beading in APP-transfected neurons. (c) Percentage beading in APP-transfected or serum-deprived neurons treated 1 h before and continuously with stressor (Pre-treatment) or 48 h after stressor (post-beading treatment) with 25 or 50 µM VX-765 or with 5 µM Z-YVAD-fmk Casp1 peptide inhibitor. Pre-treatment showed main effects after APP$^{WT}$-transfection (Treatment main effect F(4,10)=10.17, p=0.0015; Time main effect F(2,20)=93.32, p<0.0001; Treatment×Time interaction F(8,20)=6.736, p=0.0003, two-way repeated measures ANOVA, Dunnett's post hoc compared to APP$^{WT}$+DMSO) and serum deprivation (Treatment main effect F(4,10)=10.2, p=0.0015; Time main effect F(2,20)=37.65, p<0.0001, two-way repeated measures ANOVA, Dunnett's post-hoc compared to Serum−+DMSO). Post-beading treatment showed main effects after APP$^{WT}$-transfection (Time main effect F(4,40)=102.7, p<0.0001, two-way repeated measures ANOVA, Dunnett's post-hoc compared to APP$^{WT}$+DMSO) and serum deprivation (Treatment main effect F(4,23)=14.12, p<0.0001; Time main effect F(4,23)=24.35, p<0.0001, two-way ANOVA, Dunnett's post-hoc compared to Serum−+DMSO) * p<0.05,  p<0.01, * p<0.001, **** p<0.0001. (d-e) HPN secreted or cellular A$β_{42}$/total A$β_{38+40+42}$ (d) (F(3,4)=12.73, p=0.0163, ANOVA, Dunnett's post-hoc compared to Serum+DMSO, *p<0.05), and (e) levels of secreted Il-1β, IFN-γ, TNF-α, and Il-6 from untreated (+S), serum deprived (−S), or serum-deprived human neurons treated with 25 or 50 µM VX-765.
Figure 13E:
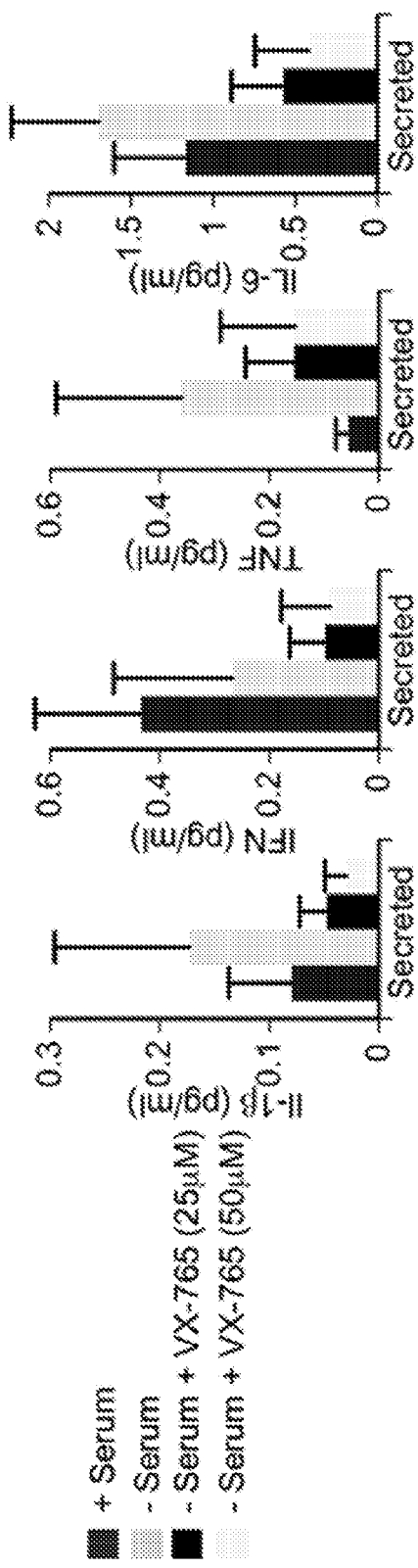

Example 13: VX-765 Prevents Axonal Degeneration in Human Cultures of CNS Neurons To determine if VX-765 can protect human neurons against neurodegeneration, VX-765 was assessed in primary human fetal CNS neuron cultures. Treatment of HPN with 25, 50, 100, or 200 μM VX-765 for 72 hours was not toxic (FIG. 13a). EGFP was homogeneously distributed within the cell body and neurites of CNS human primary neurons (HPN), whereas co-expression of APP$^{WT}$ resulted in EGFP positive beading indicative of neurodegeneration (FIG. 13b). HPN were pre-treated with VX-765 for 1 h before APP transfection and treatment continued thereafter. VX-765 treatment at 25 and 50 μM concentration prevented neuritic beading in APP$^{WT}$-transfected neurons at 48 and 72 h post transfection, similar to the Casp1 Z-YVAD-fmk peptide inhibitor (FIG. 13c). Similarly, VX-765 protected against, albeit less strongly, serum-deprivation induced neuritic beading. To assess if neuritic beading was reversible, VX-765 was administered 48 hours after APP$^{WT}$ transfection or serum deprivation. VX-765 treatment did not reverse but prevented further neuritic beading in APP-transfected neurons. In contrast, YVAD-fmk was unable to reverse or prevent neuritic beading at any time-point. As observed in vivo, 50 μM VX-765 reduced secreted and cellular Aβ$_{42}$/total Aβ levels. The 25 μM concentration reduced secreted, but not cellular, Aβ$_{42}$/total Aβ levels. Levels of Il-1β, IFN-γ, TNF-α, and Il-6 were also reduced at both concentrations of VX-765, although variability amongst the different neuronal preparations resulted in a trend rather than a statistically significant result. These results indicate that VX-765 can prevent human neuronal degeneration.

The results of the studies described herein show that the effect of VX-765 is exquisitely rapid against episodic and spatial memory impairment, which are normalized after only 1 (3 injections) or 3 (9 injections) weeks of treatment, respectively. Reversal of cognitive impairment is accompanied by a normalization of microglial and astroglial reactivity and synaptophysin immunohistochemical staining, a normalization of gene expression of four different synaptic components, and the prevention of progressive amyloid pathology in the brain.

Figure 20:
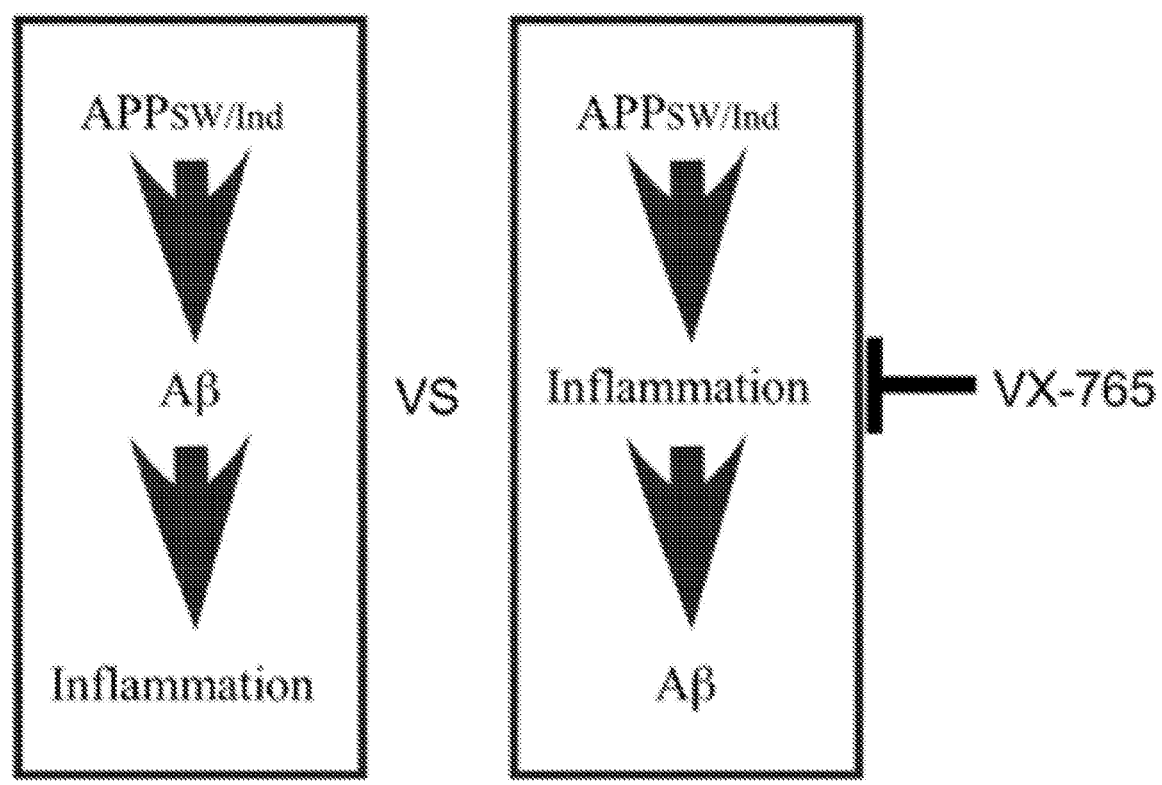
FIG. 20: Schematic diagram to illustrate pathway inhibited by VX-765. The APP$^{Sw/Ind}$ transgene is thought to increase Aβ levels, which then generate inflammation through the activation of the microglia (Left panel). Without being bound to a particular theory, the results described herein are consistent with a model where the APP$^{Sw/Ind}$ transgene first induces inflammation, and then leads to an increase of Aβ (Right panel). By inhibiting Casp1, VX-765 blocks inflammation and subsequent Aβ accumulation.

The reduction of Aβ levels in VX-765-treated mice was unexpected. After only 12 treatments over 3 months' time, the levels of RIPA soluble, immunostained, and thioflavin S positive Aβ were considerably lower than in vehicle-treated J20 mice, and remained similar to levels in pre-treated 5 months old J20. These results indicate that VX-765 stops the progressive accumulation and deposition of Aβ. Since VX-765 inhibits inflammatory Casp1, the results indicate that in the J20 mouse model, inflammation is driving Aβ accumulation and contrast with the more popular view that Aβ drives inflammation (FIG. 20).

Whereas the J20 is a familial AD mouse model, the presence of the Nlrp1-Casp1-Casp6 pathway in mild cognitively impaired and in the early and late stages of sporadic human AD suggest that the treatment described herein will also work in sporadic AD.

It is possible that an efficient treatment against AD will entail early treatment to prevent neuronal degeneration. With this in mind, we chose to treat the mice only 1 month after the onset of cognitive decline. The outcome was unexpectedly positive and indicates that VX-765 may be used for treatment of mild cognitively impaired individuals or at the very early onset of clinically diagnosed AD.

Figure 22:
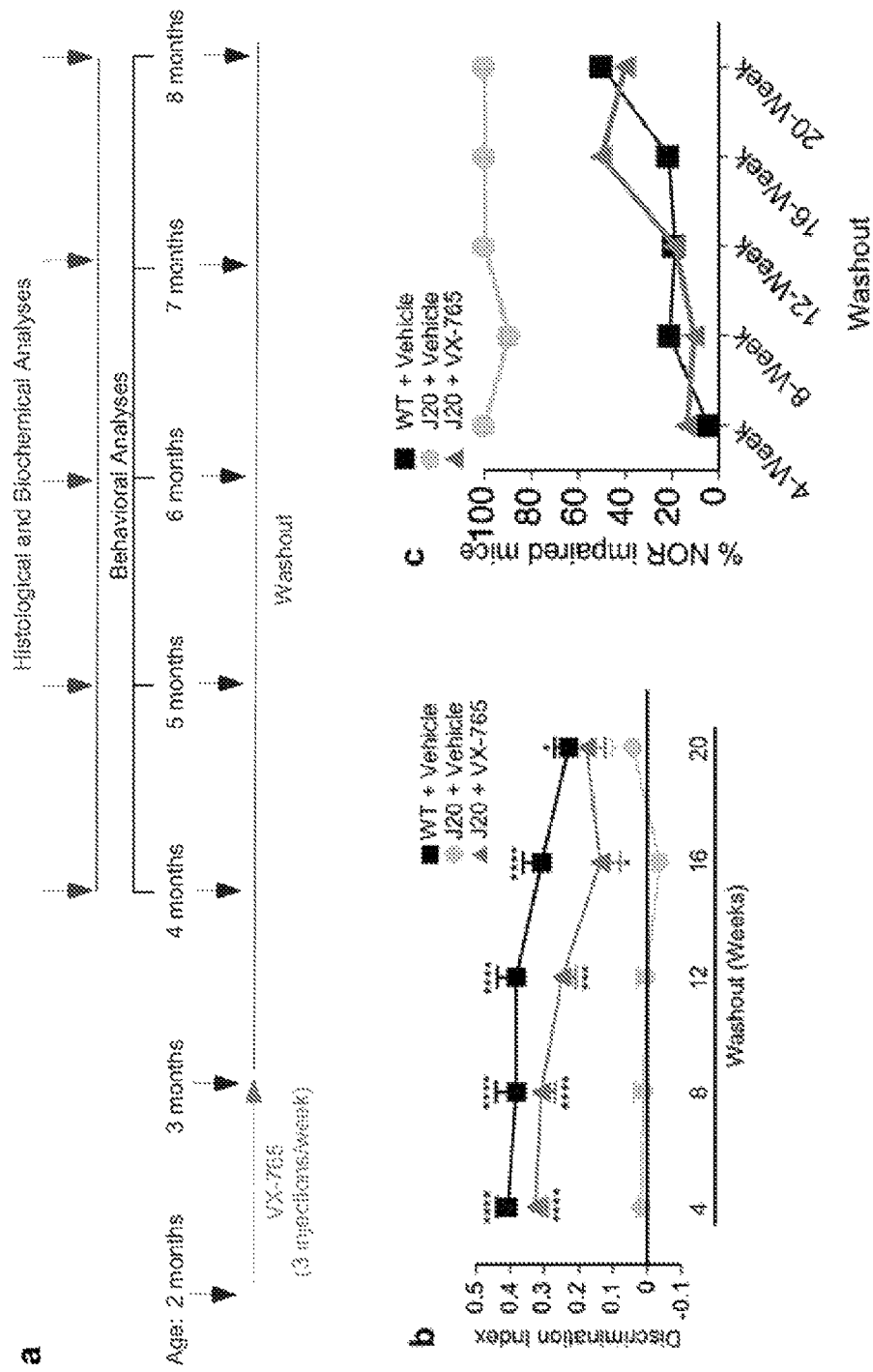
FIG. 22: Novel object recognition behavioral assay to assess episodic memory in J20 mice. Mice were treated with vehicle (WT and J20) or 50 mg/kg VX-765 (J20) at 2 months of age for 1 month (3 injections per week×4 weeks=12 injections). (a) Schematic representation of the manner in which the studies were carried out. (b) Discrimination index indicates the number of touches of the novel object minus the number of touches of the familiar object divided by the number of total touches for both objects. Two-way ANOVA (F(2,240)=75.62, p<0.0001) with Dunnett's compared to the J20+vehicle. * p<0.05, **** p<0.0001 (c) % mice impaired in NOR in each group of mice tested at the different time points.

Example 14: VX-765 is Capable of Preventing Alzheimer Disease (AD)-Related Behavioral and Memory Deficits and Pathologies in the J20 Amyloid Precursor Protein Swedish/Indiana AD Mouse Model We directly tested whether pre-symptomatic inhibition of inflammation in a mouse genetic model of Alzheimer disease can stem the progression of memory and behavioral deficits, and Alzheimer disease-like pathology. The J20 amyloid precursor protein Swedish/Indiana mutant mouse was treated at 2 months of age for a one month period with 50 mg/Kg Caspase-1 inhibitor VX-765 (FIG. 22a). The drug was stopped and animals behaviorally assessed at 4 months of age (1 month wash-out), the age at which mice exhibit NOR deficits, and every month thereafter until the mice reached 8 months of age.

Figure 21:
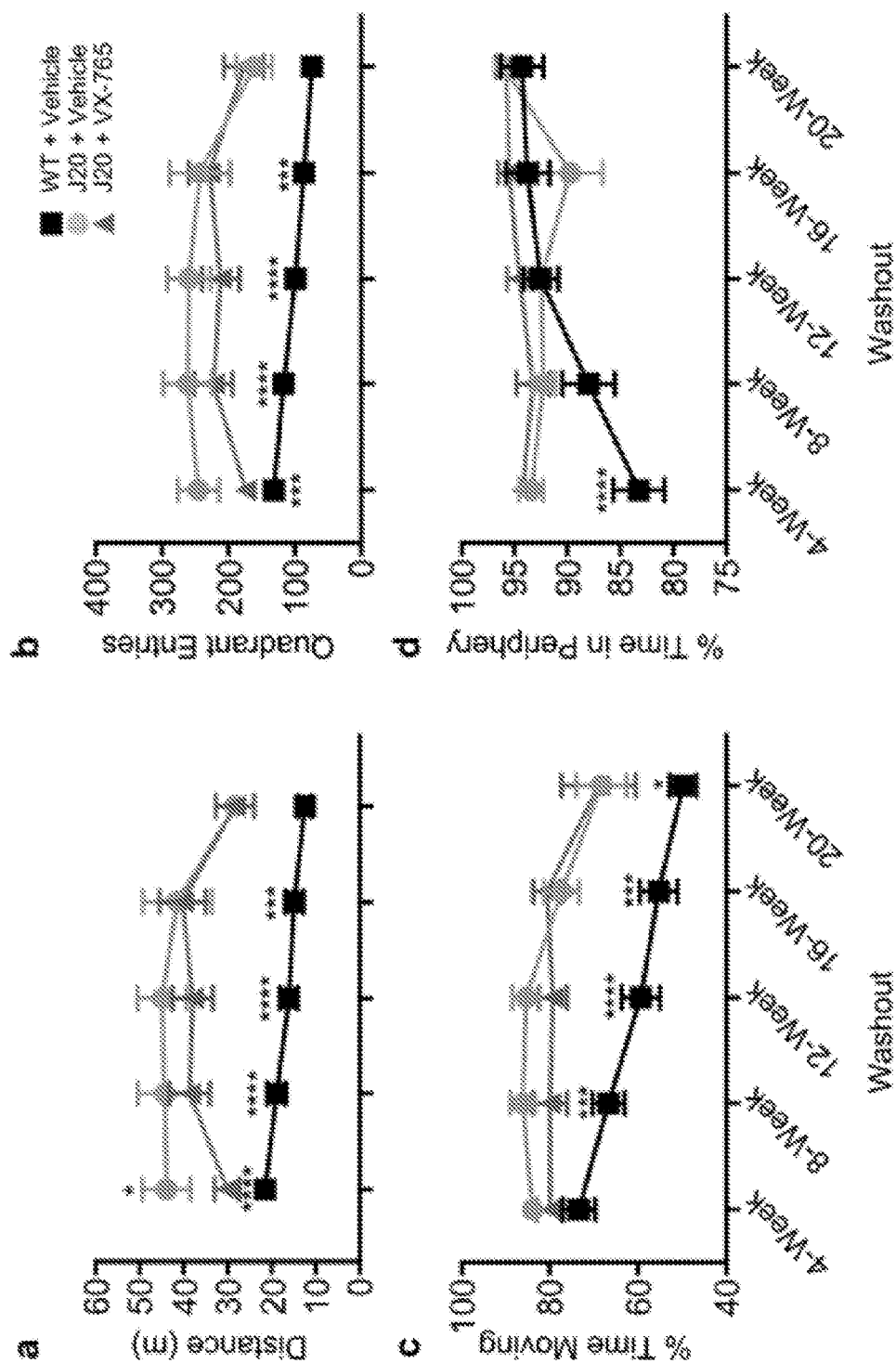
FIG. 21: Open-field assessment to assess hyperactivity in J20 mice. Mice were treated with vehicle (WT and J20) or 50 mg/kg VX-765 (J20) at 2 months of age for 1 month (3 injections per week×4 weeks=12 injections). Hyperactivity was assessed by measuring the distance travelled (a), the number of quadrant entries (b), and the % time moving (c), while anxiety was assessed by the % time spent in periphery (d).

J20 hyperactivity was assessed with open field. At 4 months of age (4 week washout), vehicle-treated J20 mice have a significant increase in distance travelled (FIG. 21a) and number of quadrant entries (FIG. 21b) than vehicle-treated wild-type (WT) mice. In contrast, the VX-765-treated J20 mice behave as the vehicle-treated WT mice. However, the beneficial effect of VX-765 preventative treatment on hyperactivity is lost at the 8 week washout assessment and thereafter. Furthermore, VX-765 did not alter the higher % time of movement in J20 during the assay from the 8 week to 20 week washout period (FIG. 21c). Anxiety measured by thigmotaxis was observed at the 4 week washout in both J20 groups due to a lower amount of time by the WT mice in the periphery (FIG. 21d). Thereafter, all groups showed identical amount of time in the periphery. These results indicate that the hyperactivity of the J20 mice can be stemmed for a short period of time but is not sustained. These results are consistent with our previous data where treatment of symptomatic mice required three weeks of VX-765 treatment to eliminate the hyperactivity.

Figure 28A:
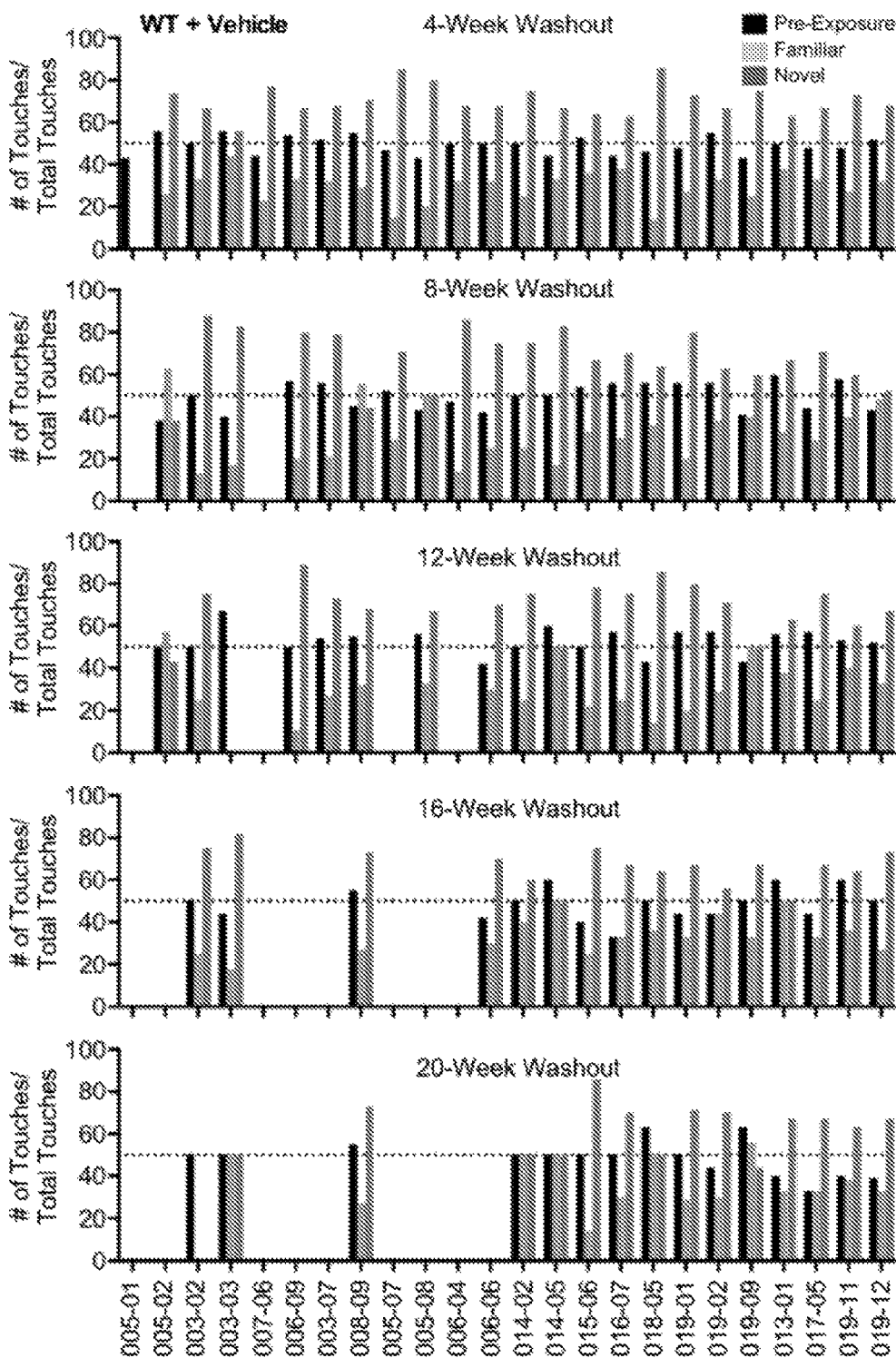
FIG. 28a-c: Preventative treatment of J20 mice with VX-765 (see Example 14). Data shows NOR performance of individual mice within each group.
Figure 28B:
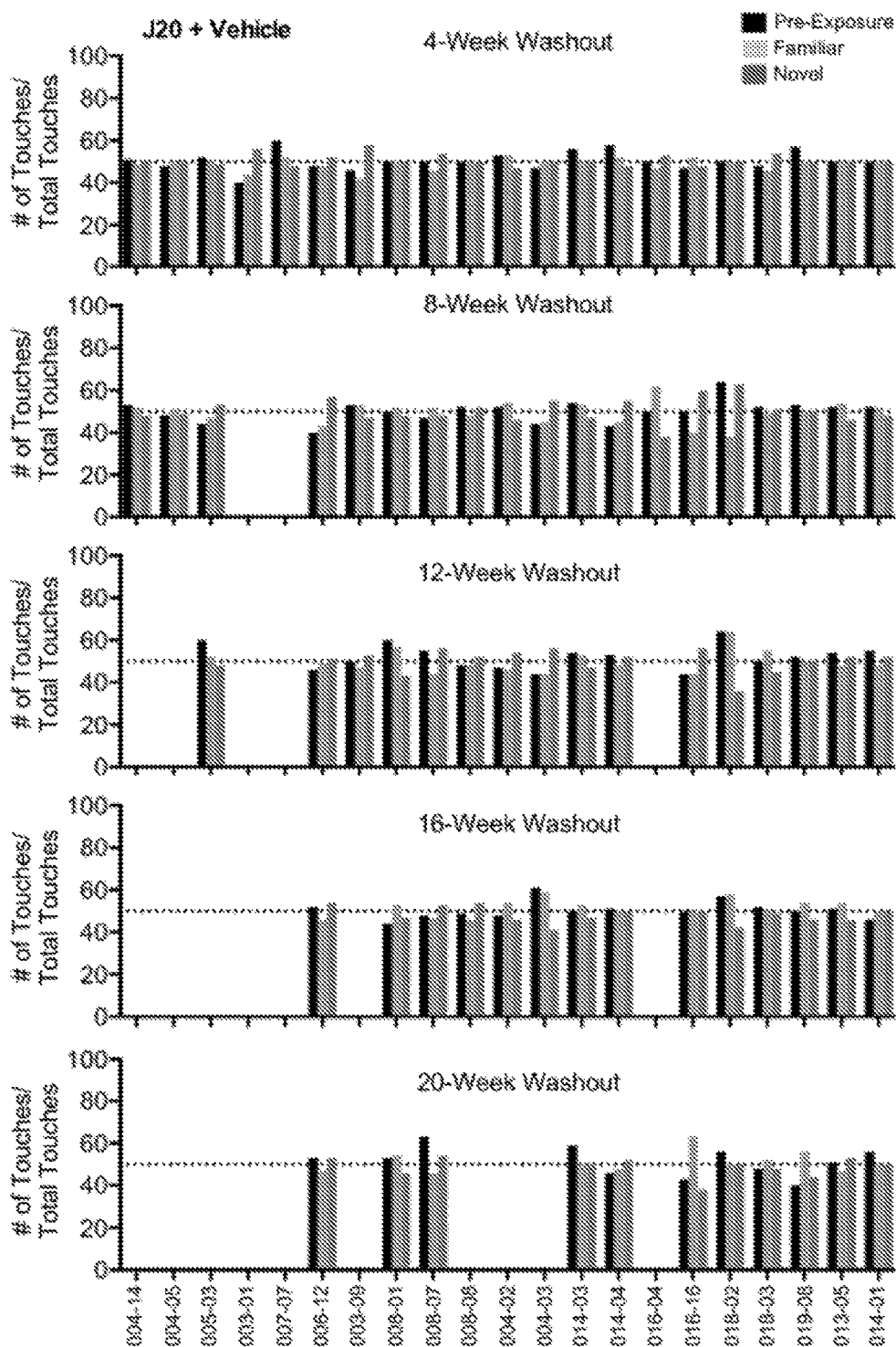
Figure 28C:
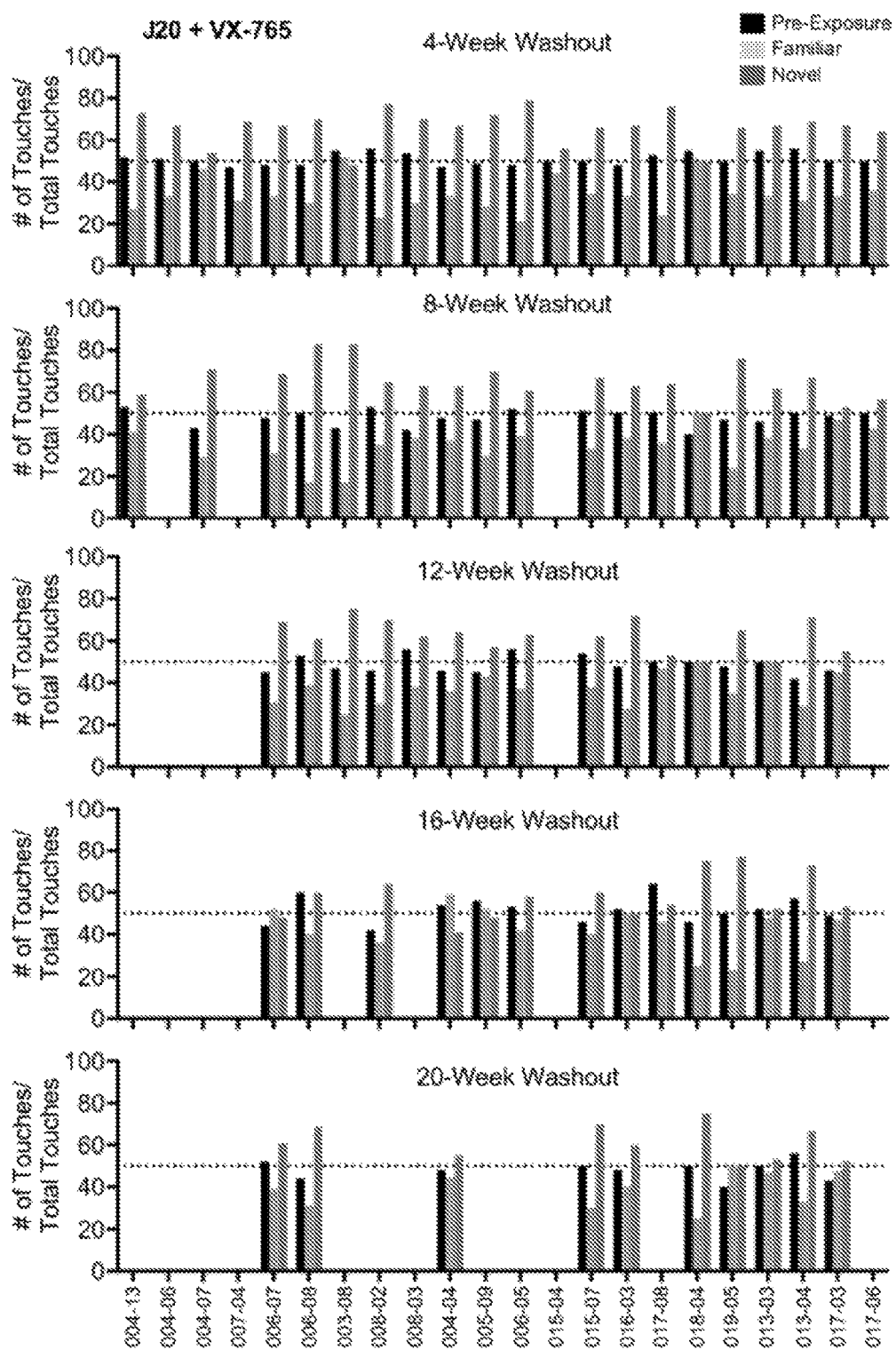

Episodic memory was assessed with the novel object recognition (NOR) assay and results expressed as discrimination index. The vehicle-treated J20 are strongly impaired in NOR at each of the evaluation time points (FIG. 22b). In contrast, the vehicle-treated WT mice perform very well at each time point although there is a decrease in discrimination index at the 20 week washout time point, possibly due to habituation to the test. On average, the VX-765-treated J20 mice perform like the WT mice at each washout time points. After 16 and 20 week washout, the VX-765-treated J20 exhibit a lower performance although they are still performing better than vehicle-treated J20 mice. When looking at individual mice, all groups contain a few mice that are impaired in NOR (FIG. 28a-c). However, the percentage of impaired VX-765-treated mice does not differ significantly from vehicle-treated WT mice (FIG. 22c), suggesting that the increased NOR impairment in these two groups could be due to mice habituation with the assay. These results indicate that the VX-765 preventive treatment is highly efficient in delaying the onset of episodic memory deficits in the J20 mice.

Figure 23:
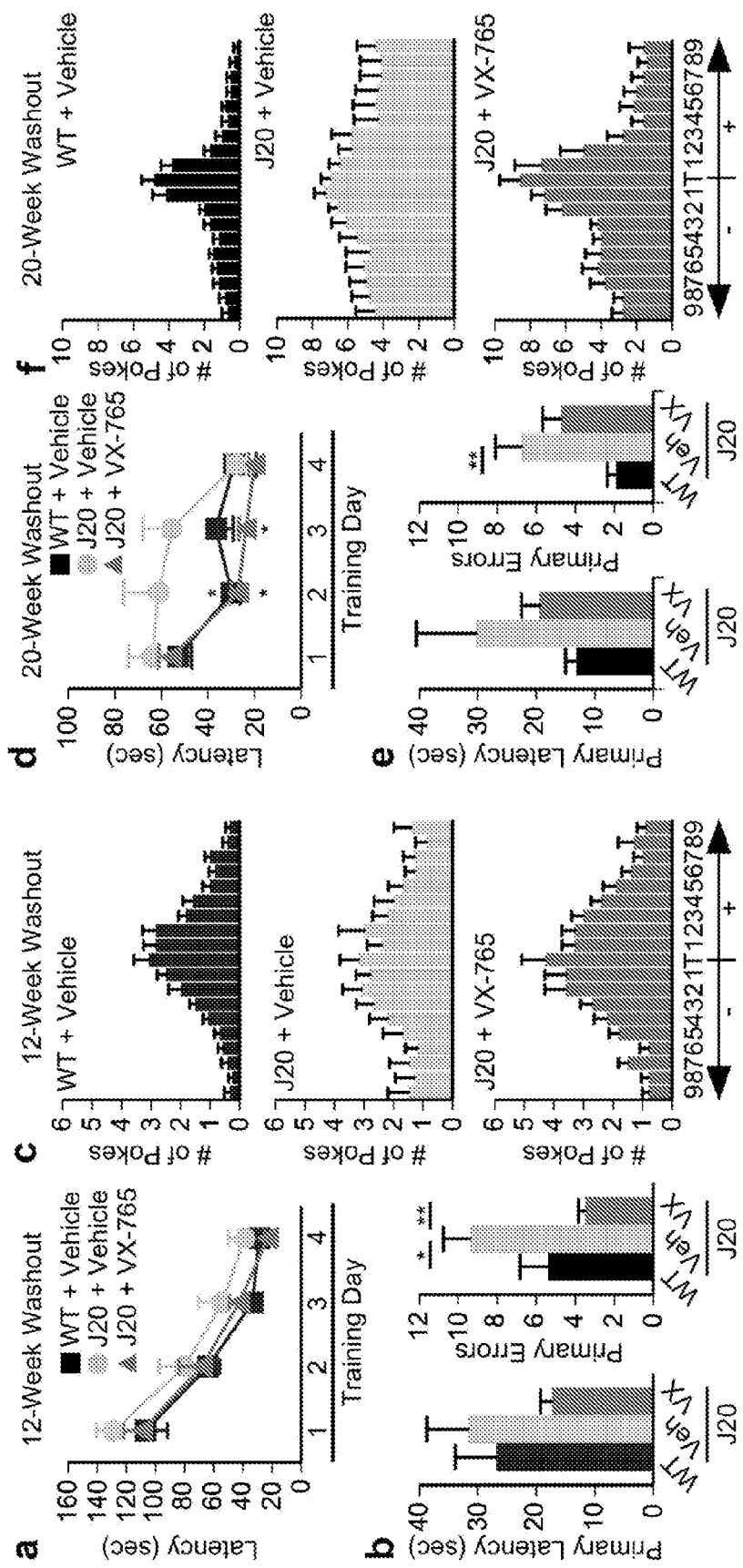
FIG. 23: Barnes maze to assess spatial memory in J20 mice. Barnes maze tested at washout at (a-c) 12 week (6 months of age) and (d-f) 20 week (8 months of age). (a,d) Learning to find the escape hatch over 4 days in seconds. (b,e) Primary latency to reach the escape hatch and primary errors to find the hatch. In (b) One-way ANOVA (F(2,29)=5.948, p=0.0068), in (e) One-way ANOVA (F(2,22)=7.2545, p=0.0038) followed by Dunnett's pot-hoc *p<0.05, ** p<0.01. (c,f) Probe test: number of pokes for each of the 20 holes of the Barnes maze when hatch hole is blocked. T indicates target hole where hatch was accessible during training.

Spatial memory was assessed with the Barnes maze on mice at 6 months of age (12-week washout time point), the age at which J20 acquire spatial memory deficits. All three groups of mice were efficient in learning the task by the 4$^{th}$ day of training (FIG. 23a). On the probe day, primary latency to reach the target did not differ significantly between groups but the VX-765-treated J20 mice tended towards a better performance (FIG. 23b). However, primary errors in reaching the target were significantly increased in vehicle-treated J20 mice compared to vehicle-treated mice. VX-765 preventive treatment corrected this deficit. Furthermore, VX-765-treated J20 mice showed a better ability to distinguish the target area compared to vehicle-treated J20 mice (FIG. 23c). A second Barnes maze was run at the 20-week washout time point. The VX-765-treated mice performed normally in the learning phase, but the vehicle-treated J20 mice showed a delay in learning (FIG. 23d). However, while there were trends towards an improvement in primary latency and primary errors in VX-765-treated mice, these did not reach statistical significance (FIG. 23e). Nevertheless, the VX-765-treated mice performed better than the Vehicle-treated J20 mice in identifying the target area in the probe test (FIG. 23f). Together, these results indicate that pre-treatment with VX-765 can significantly delay the onset of episodic and spatial memory deficits, but not hyperactivity symptoms, up to 5 months after the treatment.

Figure 24C:
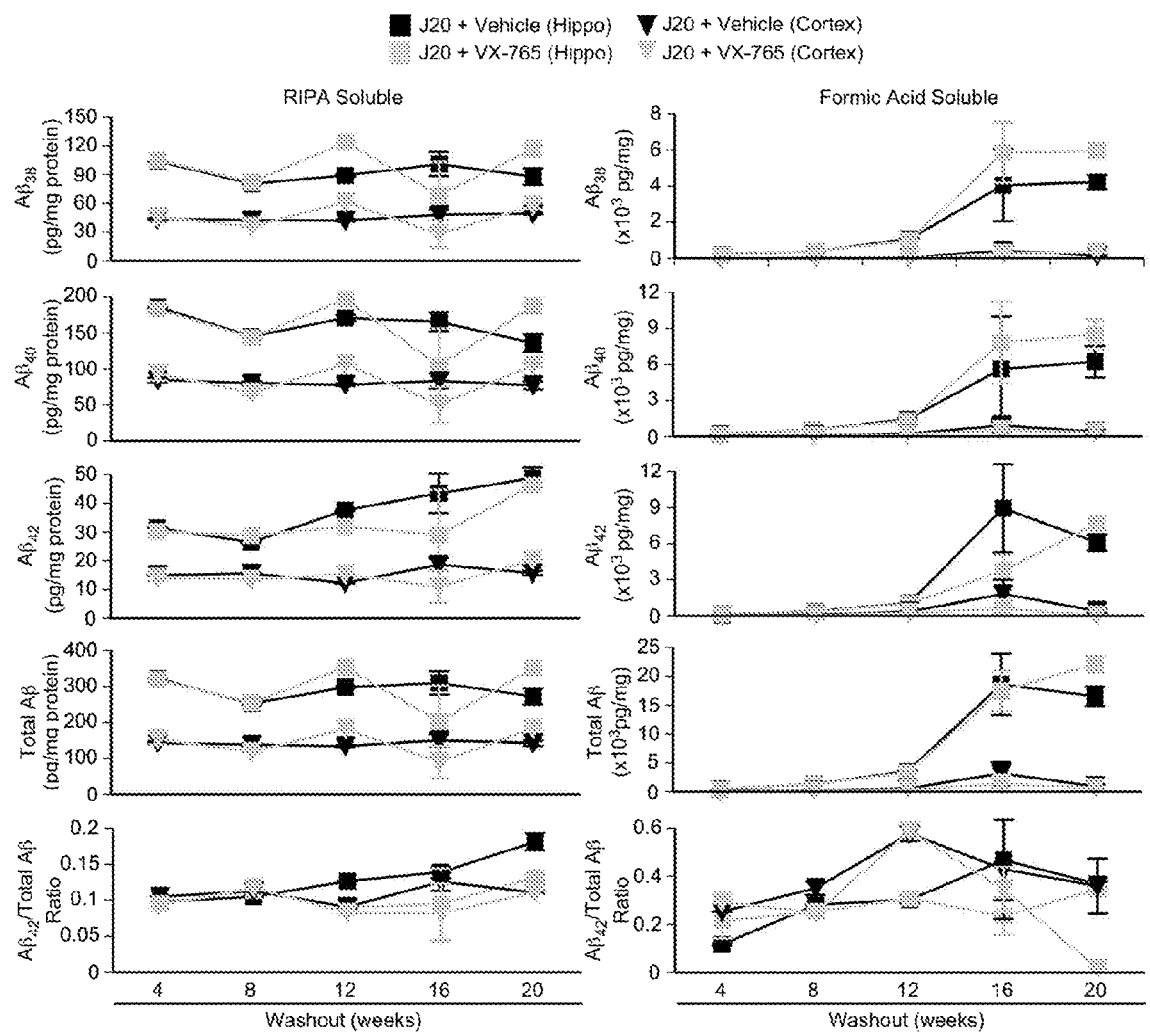
FIG. 24: Immunostaining of mice brains at 8 months of age (20 week washout) with anti-amyloid beta peptide 1-40 antiserum (a). All sections were immunostained together and automatically with Dako immunostainer, immunoreactivity was revealed with anti-rabbit HRP and diamino benzidine. (b) Quantitation of the immunopositive density of amyloid staining at 4, 8, 12, 16, and 20 weeks washout of VX-765 when mice are 4, 5, 6, 7, and 8 months respectively. (c) ELISA analyses of RIPA-soluble and formic-acid soluble hippocampal and cortical tissue protein extracts.

After behavioral analyses, we sacrificed the mice and performed immunohistological staining on the tissue sections. The hippocampus of vehicle-treated J20 mice brains shows ample immunostaining against amyloid in neurites and plaque-like deposits (FIG. 24a). Surprisingly, a few hippocampi of VX-765-treated mice brains had almost no immunopositive reactivity to the anti-amyloid antiserum. There are fewer compact plaques and amyloid deposits, mostly restricted to the area of the stratum lacunosum molecular of the hippocampus. However, in other VX-765-treated J20 mice brains, the levels of amyloid do not decrease significantly. Quantitation of the immunopositive density of amyloid staining of all mice studied indicates slightly less amyloid in the VX-765-treated mice hippocampi and cortex at the 16 and 20 week washout time point (FIG. 24b). ELISA analyses of hippocampal tissue protein extracts do not detect major differences in RIPA-soluble $A\beta_{38}$, $A\beta_{40}$, and $A\beta_{42}$, total $A\beta$, and $A\beta_{42}$/total $A\beta$ although there is a trend towards lower levels of these $A\beta$ at the 16 week washout time point (FIG. 24c). $A\beta_{42}$/total $A\beta$ levels are slightly decreased relative to the vehicle-treated J20 hippocampus at the 20 week washout time point ($p \leq 0.070$). There is no effect of VX-765 treatment on any measures of amyloid levels in cortical tissue RIPA-soluble protein extracts. Formic acid soluble amyloid is generally higher in the hippocampus than in the cortex at the 16 week and 20 week washout time points. $A\beta_{42}$/total $A\beta$ levels are lower at the 20 week washout time point in VX-765-treated J20 hippocampi ($p \geq 0.05$). Formic acid soluble cortical levels of any of the $A\beta$ measures are not reduced with VX-765 treatment. These results indicate that the pre-symptomatic one month treatment with VX-765 slightly reduces the accumulation of RIPA-soluble and formic acid soluble aggregated $A\beta_{42}$. Because cognition remained intact in the VX-765-treated mice, these results indicate that the amyloid is unlikely responsible for impaired cognition in the J20 mice.

Figure 25A:
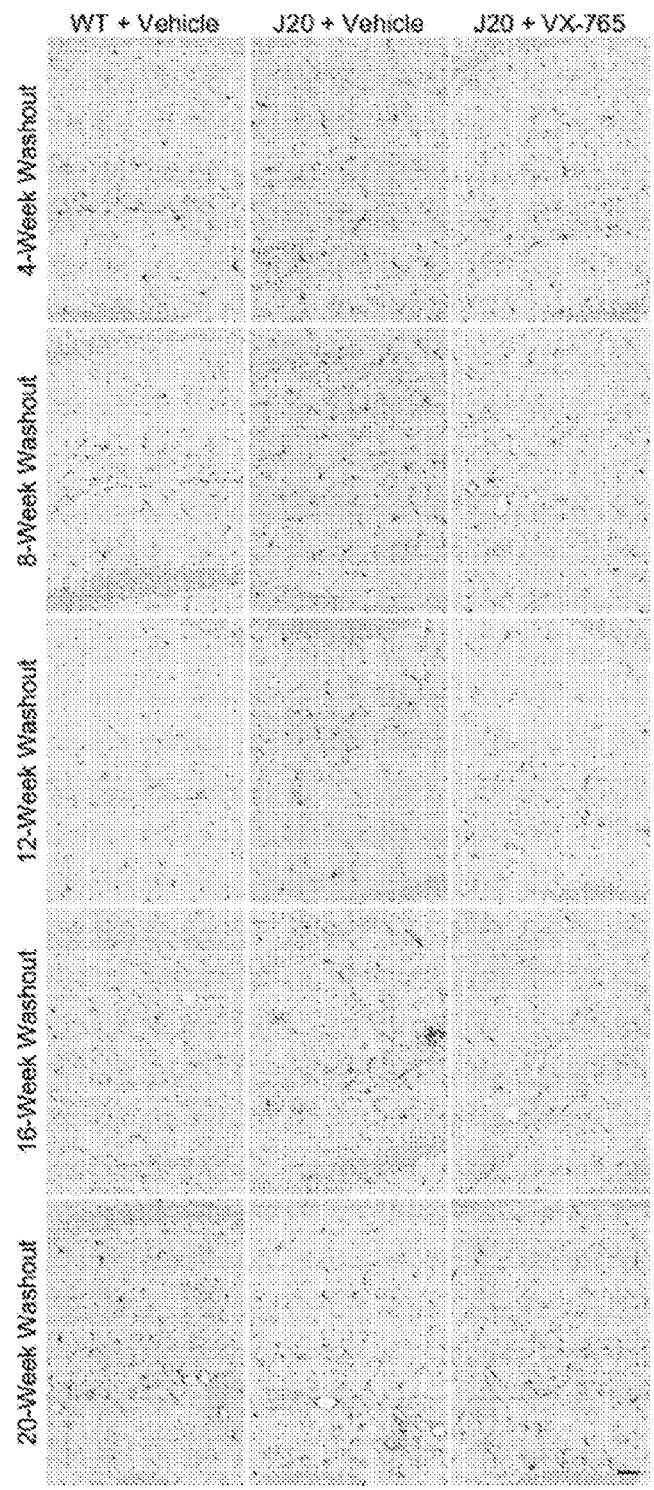
FIG. 25: Iba1 immunopositive staining in the mice brain hippocampus at different times of washout (a,b). All sections were immunostained together and automatically with Dako immunostainer and the number of Iba1-immunopositive neurons counted stereologically. Statistics done as described in FIG. 10b. (c) Analyses of subtypes of Iba1-immunopositive microglia as described in FIG. 10c.
Figure 25B:
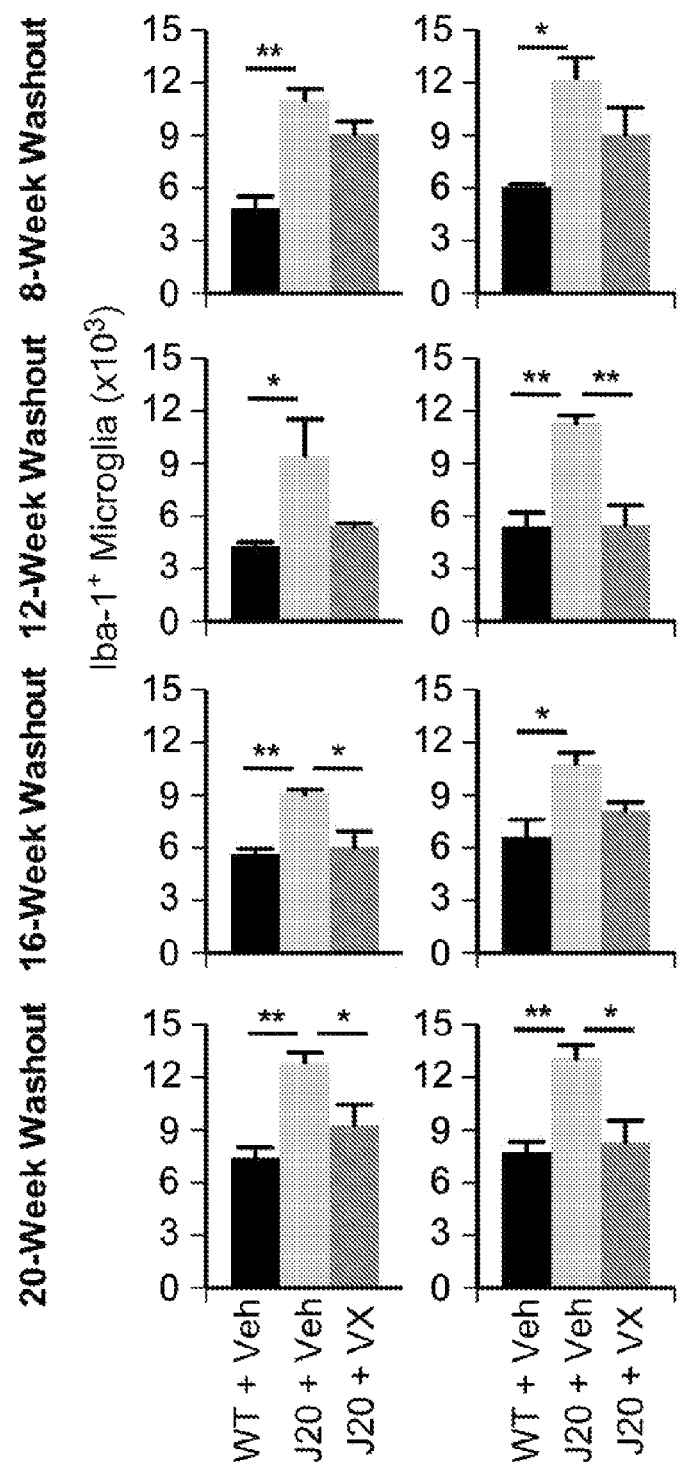
Figure 25C:
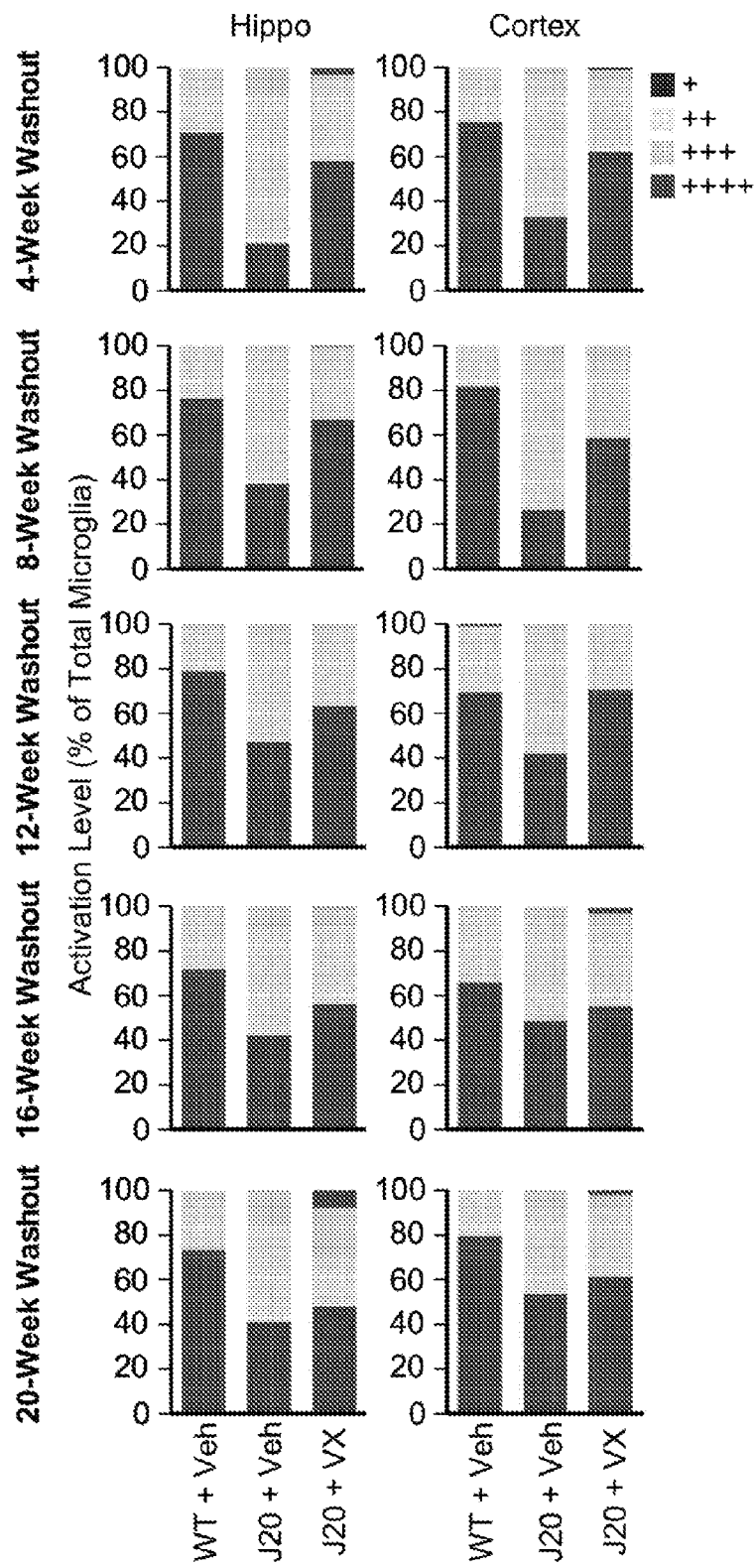
Figure 26A:
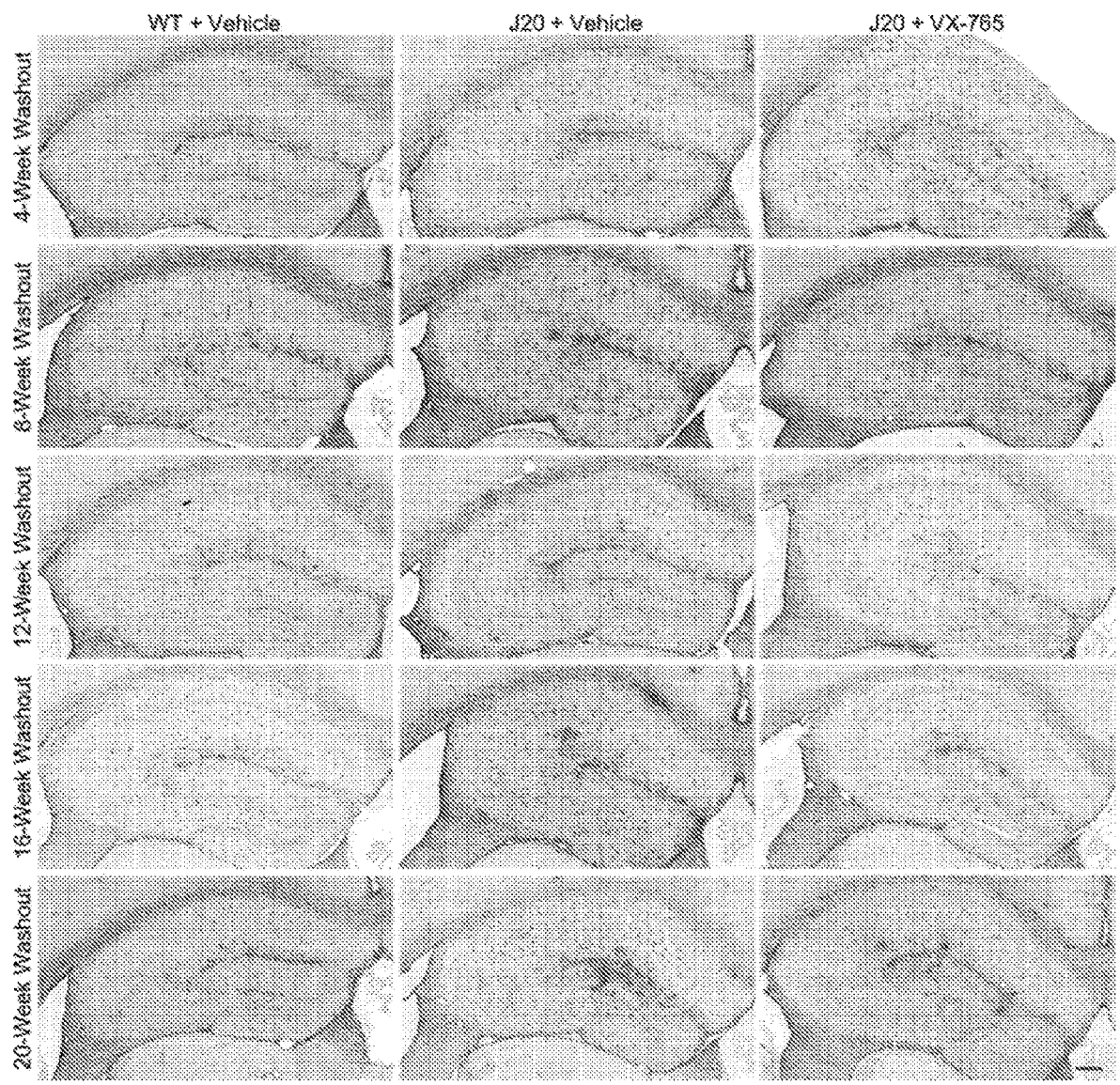
FIG. 26: GFAP immunopositive staining in the hippocampus of mice brains at different times of washout (a,b). All sections were immunostained together and automatically with Dako immunostainer. Quantitation of GFAP-immunopositive astrocytes was done as described above.
Figure 26B:
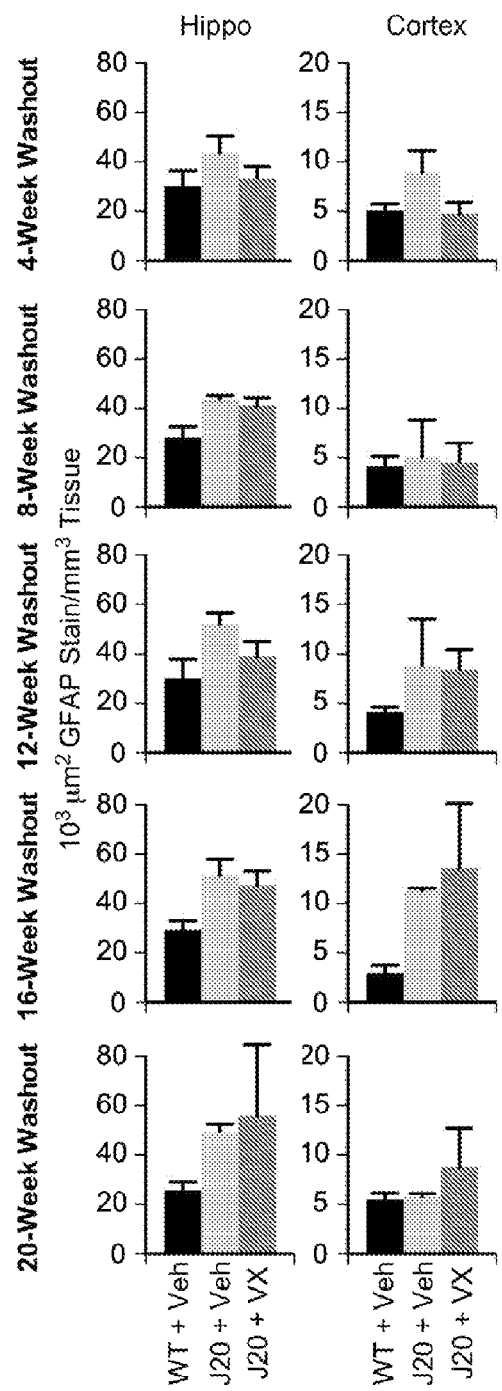

Iba1 positive immunostaining to reveal activated microglia shows that the VX-765 pre-symptomatic treatment has also strongly decreased microglial inflammation in the hippocampus and cortex of the J20 brains (FIG. 25a&b). Analyses of the subtype of microglia indicates that VX-765 restores resting microglia numbers (+) and decreases more activated microglia (++, +++) up to the 12 week washout time point in both the hippocampus and the cortex (FIG. 25c). Thereafter, there is not much difference between vehicle-treated and VX-765-treated J20 mice brains, except that an increase in (++++) phagocytic microglia is noted with VX-765 treatment. The effect is maintained after 20 weeks of washout of the drug. Similar results were obtained for astrocytic GFAP immunostaining, although the difference is not as pronounced as for Iba1 and does not reach statistical significance (FIG. 26a&b).

Figure 27:
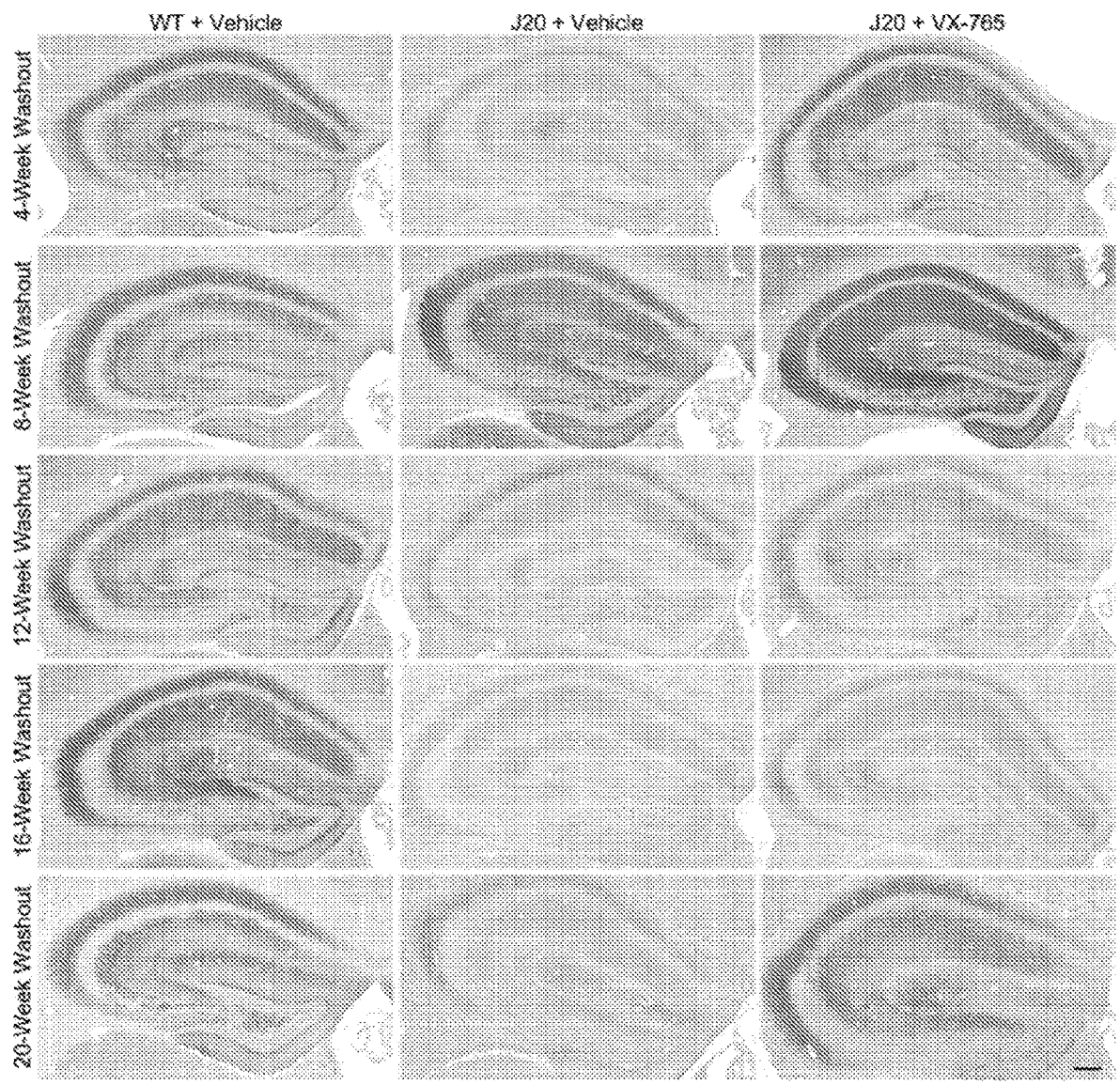
FIG. 27: Synaptophysin immunopositive staining in the hippocampus of mice brains at different times of washout. All sections were immunostained together and automatically with Dako immunostainer.

Synaptophysin immunostaining is severely depressed in the vehicle-treated J20 mice hippocampus (FIG. 27). Synaptophysin immunostaining is partly re-established in the VX-765-treated hippocampus.

Together, these results indicate that Alzheimer disease memory and behavioral deficits and Alzheimer disease-like pathology can be strongly reduced for 6 months by a preventative treatment of one month with 50 mg/kg VX-765, before mice show symptoms.

The preclinical results indicate that periodic treatment with VX-765 could prevent cognitive deficits and progressive AD pathology in humans. Conversion of mice age and time of treatment to human age indicates that a 3-4 year pre-symptomatic treatment in humans could prevent the progression of the disease for approximately 10-15 years. VX-765 could thus be used to treat pre-symptomatic aged individuals as a preventative treatment.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Wannamaker, W., et al. (S)-1-((S)-2-{[1-(4-amino-3-chloro-phenyl)-methanoyl]-amino}-3,3-dimethyl-butanoy l)-pyrrolidine-2-carboxylic acid ((2R,3S)-2-ethoxy-5-oxo-tetrahydro-furan-3-yl)-amide (VX-765), an orally available selective interleukin (IL)-converting enzyme/caspase-1 inhibitor, exhibits potent anti-inflammatory activities by inhibiting the release of IL-1 beta and IL-18. *J Pharmacol Exp Ther* 321, 509-516 (2007).
2. Dudchenko, P. A., Talpos, J., Young, J. & Baxter, M. G. Animal models of working memory: a review of tasks that might be used in screening drug treatments for the memory impairments found in schizophrenia. *Neuroscience and biobehavioral reviews* 37, 2111-2124 (2013).
3. Grayson, B., et al. Assessment of disease-related cognitive impairments using the novel object recognition (NOR) task in rodents. *Behav Brain Res* 285, 176-193 (2015).
4. Paylor, R., Spencer, C. M., Yuva-Paylor, L. A. & Pieke-Dahl, S. The use of behavioral test batteries, II: effect of test interval. *Physiol Behav* 87, 95-102 (2006).
5. Albrecht, S., Bogdanovic, N., Ghetti, B., Winblad, B. & LeBlanc, A. C. Caspase-6 activation in familial Alzheimer disease brains carrying amyloid precursor protein or presenilin I or presenilin II mutations. *J Neuropathol Exp Neurol* 68, 1282-1293 (2009).
6. Albrecht, S., et al. Activation of caspase-6 in aging and mild cognitive impairment. *Am J Pathol* 170, 1200-1209 (2007).
7. Kaushal, V., et al. Neuronal NLRP1 inflammasome activation of Caspase-1 coordinately regulates inflammatory interleukin-1-beta production and axonal degeneration-associated Caspase-6 activation. *Cell Death Differ* 22, 1676-1686 (2015).
8. Keller, M., Ruegg, A., Werner, S. & Beer, H. D. Active caspase-1 is a regulator of unconventional protein secretion. *Cell* 132, 818-831 (2008).

What is claimed is:

1. A method of reversing the progression of cognitive impairment in a subject, said method comprising administering a caspase-1 inhibitor to the subject, wherein the cognitive impairment comprises a memory deficit, wherein the memory deficit comprises a deficit in one or more of episodic memory, spatial memory and working memory, wherein the caspase-1 inhibitor is a compound having Formula I:

wherein $R^1$ is

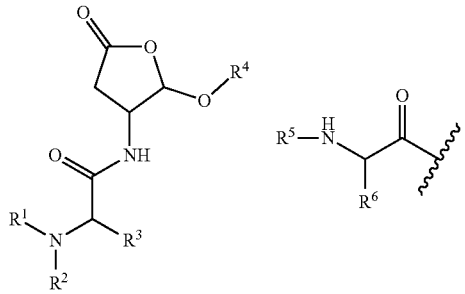

$R^2$ and $R^3$ taken together form a ring, wherein said ring is:

wherein, in each ring, any hydrogen atom is optionally and independently replaced by $R^7$ and any set of two hydrogen atoms bound to the same atom is optionally and independently replaced by carbonyl;

when the ring formed by $R^2$ and $R^3$ is then $R^5$ is $R^8C(O)-$, and $R^8$ is phenyl, thiophene, or pyridine, wherein each ring is optionally substituted with up to 5 groups independently selected from $R^9$, and wherein at least one position on the phenyl, thiophene, or pyridine is substituted by $R^{10}$;

when the ring formed by $R^2$ and $R^3$ is

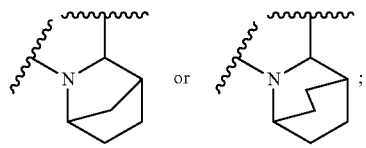 [SMILES: *C1C2CCC(C2)N1* ; *C1C2CCC(CC2)N1*]

then $R^5$ is $R^8C(O)-$, $HC(O)$, $R^8SO_2-$, $R^8OC(O)$, $(R^8)_2NC(O)$, $(R^8)(H)NC(O)$, $R^8C(O)C(O)-$, $R^8-$, $(R^8)_2NC(O)C(O)$, $(R^8)(H)NC(O)C(O)$, or $R^8OC(O)C(O)-$; and $R^8$ is $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic$)-(C_{1-12}$aliphatic$)-$, $(C_{6-10}$aryl$)-(C_{1-12}$aliphatic$)-$, (5-10 membered heterocyclyl)-$(C_{1-12}$aliphatic$)-$, or (5-10 membered heteroaryl)-$(C_{1-12}$aliphatic$)-$; or two $R^8$ groups bound to the same atom form together with that atom a 3-10 membered aromatic or nonaromatic ring; wherein any ring is optionally fused to an $C_{6-10}$aryl, 5-10 membered heteroaryl, $C_{3-10}$cycloalkyl, or 5-10 membered heterocyclyl; wherein up to 3 aliphatic carbon atoms may be replaced by a group selected from O, N, $NR^{11}$, S, SO, and $SO_2$, wherein $R^8$ is substituted with up to 6 substituents independently selected from $R^{12}$;

$R^4$ is H, $C_{1-12}$aliphatic, $C_{3-10}$cycloaliphatic, $C_{6-10}$aryl, 5-10 membered heterocyclyl, 5-10 membered heteroaryl, $(C_{3-10}$cycloalkyl$)-(C_{1-12}$aliphatic$)-$, cycloalkenyl-$(C_{1-12}$aliphatic$)-$, $(C_{6-10}$aryl$)-(C_{1-12}$aliphatic$)-$, (5-10 membered heterocyclyl)-$(C_{1-12}$aliphatic$)-$, or (5-10 membered heteroaryl)-$(C_{1-12}$aliphatic$)-$, wherein any hydrogen atom is optionally and independently replaced by $R^{12}$ and any set of two hydrogen atoms bound to the same atom is optionally and independently replaced by carbonyl;

$R^6$ is $-C(R^{13})(R^{14})(R^{15})$, $C_{6-10}$aryl, 5-10 membered heteroaryl, or $C_{3-7}$cycloalkyl;

$R^7$ is halogen, $-OR^{11}$, $-NO_2-CN-CF_3$, $-OCF_1$, $-R^{11}$, 1,2-methylenedioxy, 1,2ethylenedioxy, $-N(R^{11})_2$, $-SR^{11}$, $-SOR^{11}$, $-SO_2R^{11}-SO_2N(R^{11})_2$, $-SO_3R^{11}$, $-C(O)R^{11}$, $-C(O)C(O)R^{11}$, $-C(O)C(O)OR^{11}$, $-C(O)C(O)N(R^{11})_2$, $-C(O)CH_2C(O)R^{11}$, $-C(S)R^{11}$, $-C(S)OR^{11}$, $-C(O)OR^{11}$, $-OC(O)R^{11}$, $-C(O)N(R^{11})_2$, $-OC(O)N(R^{11})_2$, $-C(S)N(R^{11})_2$, $-(CH_2)_{0-2}NHC(O)R^{11}$, $-N(R^{11})N(R^{11})COR^{11}$, $-N(R^{11})N(R^{11})C(O)OR^{11}$, $-N(R^{11})N(R^{11})CON(R^{11})_2$, $-N(R^{11})SO_2R^{11}$, $-N(R^{11})SO_2N(R^{11})_2$, $-N(R^{11})C(O)OR^{11}$, $-N(R^{11})C(O)R^{11}$, $-N(R^{11})C(S)R^{11}$, $-N(R^{11})C(O)N(R^{11})_2$, $-N(R^{11})C(S)N(R^{11})_2-N(COR^{11})COR^{11}$, $-N(OR^{11})R^{11}$, $-C(=NH)N(R^{11})_2$, $-C(O)N(OR^{11})R^{11}$, $-C(=NOR^{11})R^{11}$, $-OP(O)(OR^{11})_2$, $-P(O)(R^{11})_2$, $-P(O)(OR^{11})_2$, or $-P(O)(H)(OR^{11})$;

$R^9$ and $R^{12}$ are each independently halogen, $-OR^{11}$, $-NO_2$, $-CN$, $-CF_3$, $-OCF_3$, $-R^{11}$, 1,2-methylenedioxy, 1,2-ethylenedioxy, $-N(R^{11})_2$, $-SR^{11}$, $-SOR^{11}$, $-SO_2R^{11}$, $-SO_2N(R^{11})_2-SO_3R^{11}$, $-C(O)R^{11}$, $-C(O)C(O)R^{11}$, $-C(O)C(O)OR^{11}$, $-C(O)C(O)N(R^{11})_2$, $-C(O)CH_2C(O)R^{11}$, $-C(S)R^{11}$, $-C(S)OR^{11}$, $-C(O)OR^{11}$, $-OC(O)R^{11}$, $-C(O)N(R^{11})_2$, $-OC(O)N(R^{11})_2$, $-C(S)N(R^{11})_2$, $-(CH_2)_{0-2}NHC(O)R^{11}$, $-N(R^{11})N(R^{11})COR^{11}$, $-N(R^{11})N(R^{11})C(O)OR^{11}$, $-N(R^{11})N(R^{11})CON(R^{11})_2$, $-N(R^{11})SO_2R^{11}$, $N(R^{11})SO_2N(R^{11})_2$, $-N(R^{11})C(O)OR^{11}$, $-N(R^{11})C(O)R^{11}$, $-N(R^{11})C(S)R^{11}$, $-N(R^{11})C(O)N(R^{11})_2$, $-N(R^{11})C(S)N(R^{11})_2$, $-N(COR^{11})COR^{11}$, $-N(OR^{11})R^{11}$, $-C(=NH)N(R^{11})_2$, $-C(O)N(OR^{11})R^{11}$, $-C(=NOR^{11})R^{11}$, $-OP(O)(OR^{11})_2$, $-P(O)(R^{11})_2$, $-P(O)(OR^{11})_2$, or $-P(O)(H)(OR^{11})$;

$R^{10}$ is halogen, $-OR^{17}$, $-NO_2-CN-CF_3-OCF_3$, $-R^{17}$, or $-SR^{11}$, wherein $R^{10}$ has no more than 5 straight-chained atoms;

$R^{11}$ is hydrogen, $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic$)-(C_{1-12}$aliphatic$)-$, $(C_{6-10}$aryl$)-(C_{1-12}$aliphatic$)-$, (5-10 membered heterocyclyl)-$(C_{1-12}$aliphatic$)-$, or heteroaryl-$(C_{1-12}$aliphatic$)-$; wherein any hydrogen atom is optionally and independently replaced by $R^{18}$ and any set of two hydrogen atoms bound to the same atom is optionally and independently replaced by carbonyl;

$R^{13}$ is H or a $C_{1-6}$ straight-chained or branched alkyl;

$R^{14}$ is H or a $C_{1-6}$ straight-chained or branched alkyl;

$R^{15}$ is $-CF_3$, $-C_{3-7}$cycloalkyl, $C_{6-10}$aryl, 5-10 membered heteroaryl, heterocycle, or a $C_{1-6}$ straight-chained or branched alkyl, wherein each carbon atom of the alkyl is optionally and independently substituted with $R^{16}$;

or $R^{13}$ and $R^{15}$ taken together with the carbon atom to which they are attached form a 3-10 membered cycloaliphatic;

$R^{16}$ is halogen, $-OR^{17}$, $-NO_2$, $-CN$, $-CF_3-OCF_3$, $-R^{17}$, or $-SR^{17}$; wherein $R^{17}$ is $C_{1-4}$-aliphatic-;

$R^{17}$ is $C_{1-4}$-aliphatic-; and $R^{18}$ is $-OR^{17}$, $-NO_2$, $-CN$, $-CF_3$, $-OCF_3$, $-R^{17}$, 1,2-methylenedioxy, 1,2-ethylenedioxy, $-N(R^{17})_2$, $-SR^{17}$, $-SOR^{17}$, $-SO_2R^{17}-SO_2N(R^{17})_2-SO_3R^{17}$, $-C(O)R^{17}$, $-C(O)C(O)R^{17}$, $-C(O)C(O)OR^{17}$, $-C(O)C(O)N(R^{17})_2$, $-C(O)CH_2C(O)R^{17}-C(S)R^{17}$, $-C(S)OR^{17}$, $-C(O)OR^{17}$, $-OC(O)R^{17}$, $-C(O)N(R^{17})_2$, $-OC(O)N(R^{17})_2$, $-C(S)N(R^{17})_2$, $-(CH_2)_{0-2}NHC(O)R^{17}$, $-N(R^{17})N(R^{17})COR^{17}$, $-N(R^{17})N(R^{17})C(O)OR^{17}$, $-N(R^{17})N(R^{17})CON(R^{17})_2$, $-N(R^{17})SO_2R^{17}$, $-N(R^{17})SO_2N(R^{17})_2$, $-N(R^{17})C(O)OR^{17}$, $-N(R^{17})C(O)R^{17}$, $-N(R^{17})C(S)R^{17}$, $-N(R^{17})C(O)N(R^{17})_2$, $-N(R^{17})C(S)N(R^{17})_2$, $-N(COR^{17})COR^{17}$, $-N(OR^{17})R^{17}$, $-C(=NH)N(R^{17})_2$, $-C(O)N(OR^{17})R^{17}$, $-C(=NOR^{17})R^{17}$, $-OP(O)(OR^{17})_2$, $-P(O)(R^{17})_2$, $-P(O)(OR^{17})_2$, or $-P(O)(H)(OR^{17})$; $R^{17}$ is hydrogen, $C_{1-12}$aliphatic, $C_{3-10}$cycloaliphatic, $C_{6-10}$aryl, 5-10 membered heterocyclyl, 5-10 membered heteroaryl, $(C_{3-10}$cycloaliphatic$)-(C_{1-12}$aliphatic$)$, $(C_{6-10}$aryl$)-(C_{1-12}$aliphatic$)-$, (5-10 membered heterocyclyl)-$(C_{1-12}$aliphatic$)-$, or heteroaryl-$(C_{1-12}$aliphatic$)-$; or a single stereoisomer, mixture of stereoisomers, or a pharmaceutically acceptable salt thereof.

2. The method of claim 1, wherein the caspase-1 inhibitor is a compound having Formula II:

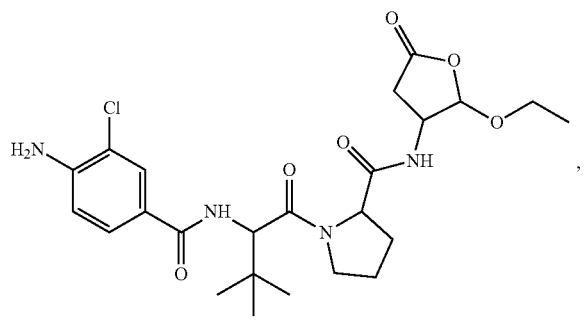

or a single stereoisomer, mixture of stereoisomers, or a pharmaceutically acceptable salt thereof.

3. The method of claim 1, wherein the caspase-1 inhibitor is VX-765 or a pharmaceutically acceptable salt thereof.

4. The method of claim 1, wherein the cognitive impairment is mild cognitive impairment.

5. The method of claim 1, wherein the cognitive impairment is subjective cognitive impairment.

6. The method of claim 1, wherein the cognitive impairment is age-dependent cognitive impairment.

7. The method of claim 1, wherein the subject has a neuropsychological profile indicative of age-dependent cognitive impairment.

8. The method of claim 1, wherein the subject suffers from neuroinflammation in the brain associated with cognitive impairment.

9. The method of claim 1, wherein said subject is a human.

10. The method of claim 1, wherein the method comprises administering a composition comprising the caspase-1 inhibitor and a pharmaceutically acceptable carrier, to the subject.

11. The method of claim 2, wherein the cognitive impairment is mild cognitive impairment.

12. The method of claim 2, wherein the cognitive impairment is subjective cognitive impairment.

13. The method of claim 2, wherein the cognitive impairment is age-dependent cognitive impairment.

* * * * *

UNITED STATES PATENT AND TRADEMARK OFFICE
CERTIFICATE OF CORRECTION

PATENT NO. : 11,160,788 B2  
APPLICATION NO. : 16/471047  
DATED : November 2, 2021  
INVENTOR(S) : Andrea Leblanc Page 1 of 1

It is certified that error appears in the above-identified patent and that said Letters Patent is hereby corrected as shown below:

In the Claims

At Column 34, Lines 4-17, in Claim 1, replace

" 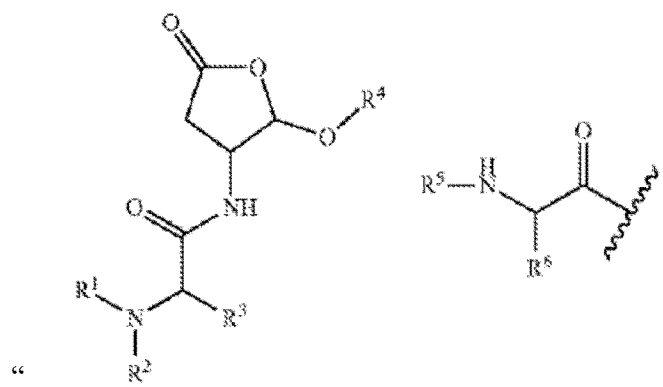 " with -- 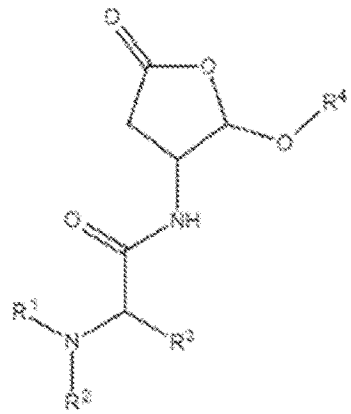

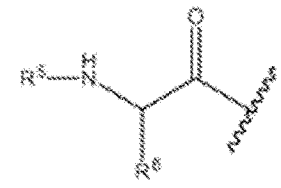 --

Signed and Sealed this  
Fifth Day of September, 2023

Katherine Kelly Vidal  
*Director of the United States Patent and Trademark Office*